United States Patent
Liu et al.

(10) Patent No.: US 12,073,920 B2
(45) Date of Patent: Aug. 27, 2024

(54) DYNAMICALLY SELECTING SEQUENCING SUBREGIONS FOR CANCER CLASSIFICATION

(71) Applicant: Grail, LLC, Menlo Park, CA (US)

(72) Inventors: Qinwen Liu, Fremont, CA (US); Frank Chu, San Jose, CA (US)

(73) Assignee: GRAIL, LLC, Menlo Park, CA (US)

( * ) Notice: Subject to any disclaimer, the term of this patent is extended or adjusted under 35 U.S.C. 154(b) by 0 days.

(21) Appl. No.: 18/354,355

(22) Filed: Jul. 18, 2023

(65) Prior Publication Data
US 2024/0021267 A1    Jan. 18, 2024

Related U.S. Application Data
(60) Provisional application No. 63/390,258, filed on Jul. 18, 2022.

(51) Int. Cl.
| | | |
|---|---|---|
| *G16H 50/20* | (2018.01) | |
| *G16B 20/00* | (2019.01) | |
| *G16B 30/10* | (2019.01) | |
| *G16B 40/20* | (2019.01) | |

(52) U.S. Cl.
CPC ............ *G16B 20/00* (2019.02); *G16B 30/10* (2019.02); *G16B 40/20* (2019.02); *G16H 50/20* (2018.01)

(58) Field of Classification Search
CPC ........ G16B 20/00; G16B 30/10; G16B 40/20; G16H 50/20
See application file for complete search history.

(56) References Cited

U.S. PATENT DOCUMENTS

| | | | | |
|---|---|---|---|---|
| 2016/0210403 | A1* | 7/2016 | Zhang | G16B 40/30 |
| 2019/0287652 | A1* | 9/2019 | Gross | G16H 50/20 |
| 2020/0005899 | A1* | 1/2020 | Nicula | G16B 25/10 |
| 2020/0105374 | A1* | 4/2020 | Hubbell | G16B 30/10 |
| 2020/0365229 | A1* | 11/2020 | Fields | G16B 40/20 |

(Continued)

FOREIGN PATENT DOCUMENTS

WO    WO 2019/084559 A1    5/2019

OTHER PUBLICATIONS

PCT International Search Report and Written Opinion, PCT Application No. PCT/US2023/028037, Oct. 19, 2023, eight pages.

*Primary Examiner* — Jay M. Patel
(74) *Attorney, Agent, or Firm* — Fenwick & West LLP

(57) ABSTRACT

Methods and systems for segmenting sequencing regions obtained from a sample interval are disclosed. sample contamination detection are disclosed. In particular, an analytics system accesses test sequences from a sample. The test sequences each include a sequencing region which, in aggregate, form an aggregate sequencing region. The analytics system segments sequencing regions from the aggregate sequencing region into sequencing subregions. Several methods of segmenting sequencing regions into sequencing subregions are disclosed: (1) maximizing cancer vs. non-cancer methylation beta differences, (2) minimizing cancer vs. non-cancer methylation beta differences, (3) segmentation based on CpG density in regions, (4) dynamic generation of sequencing subregions based on mutual information scores and cancer classification propensity. The analytics system applies selects sequencing subregions and applies a cancer classifier to those subregions to identify cancer presence in the sample.

42 Claims, 23 Drawing Sheets

(56) References Cited

U.S. PATENT DOCUMENTS

| | | | |
|---|---|---|---|
| 2021/0043275 A1* | 2/2021 | Landau | G16B 20/00 |
| 2021/0104297 A1* | 4/2021 | Venn | G06N 20/00 |
| 2021/0319907 A1* | 10/2021 | Harley | G16H 50/70 |
| 2021/0358626 A1* | 11/2021 | Nicula | G16B 20/00 |

* cited by examiner

Training of Cancer Classifier
500

Obtain a plurality of training samples of varying cancer types, each training sample comprising a set of anomalous fragments and a label of cancer type
510

For each training sample, determine a feature vector based on the filtered set of anomalous fragments of the training sample
520

For each CpG site in the feature vectors, compute an information gain based on the feature vectors of the training samples
530

Select a set of CpG sites to consider based on the computed information gain
540

Modify feature vectors based on the selected set of CpG sites
550

Train the Cancer Classifier to distinguish between cancer and non-cancer based on the feature vectors of the training samples
560

Train the Cancer Classifier to distinguish between each cancer type based on the feature vectors of the training samples
570

FIG. 5A

DYNAMICALLY SELECTING SEQUENCING SUBREGIONS FOR CANCER CLASSIFICATION

CROSS REFERENCE TO RELATED APPLICATIONS

This application is claims benefit to U.S. Provisional Application No. 63/390,258, filed Jul. 18, 2022, which is incorporated by reference in its entirety.

TECHNICAL FIELD

The described subject matter generally relates to selecting genomic regions for cancer detection, and more specifically identifying genomic regions that are indicative or non-indicative of cancer and selecting some portion of those genomic regions for analysis for determining whether a test sample includes cancer presence or cancer non-presence.

BACKGROUND

Field of Art

Deoxyribonucleic acid (DNA) methylation plays an important role in regulating gene expression. Aberrant DNA methylation has been implicated in many disease processes, including cancer. DNA methylation profiling using methylation sequencing (e.g., whole genome bisulfite sequencing (WGBS)) is increasingly recognized as a valuable diagnostic tool for detection, diagnosis, and/or monitoring of cancer. For example, specific patterns of differentially methylated regions and/or allele specific methylation patterns may be useful as molecular markers for non-invasive diagnostics using circulating cell-free (cf) DNA. As part of cancer classification, there remains a need to efficiently select sequencing regions including methylation for cancer classification given the enormous amount of sequencing data is available from a sequencing a genome.

The present disclosure is directed to addressing the above-referenced challenge. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

Early detection of a disease state (such as cancer) in subjects is important as it allows for earlier treatment and therefore a greater chance for survival. Sequencing of DNA fragments in cell-free (cf) DNA sample can be used to identify features that can be used for disease classification. For example, in cancer assessment, cell-free DNA based features (such as presence or absence of a somatic variant, methylation status, or other genetic aberrations) from a blood sample can provide insight into whether a subject may have cancer, and further insight on what type of cancer the subject may have. Towards that end, this description includes systems and methods for contamination detection of nucleic acid samples for the purpose of analyzing the sequencing data for cancer assessment.

A method for classifying a variant in a cell free nucleic acid sample is described herein. The method includes accessing a plurality of test sequences from a test sample with each test sequence of the plurality of test sequences including one or more sequencing regions of a plurality of sequencing regions, the plurality of sequencing regions, in aggregate, forming an aggregate sequencing region. The method selects one or more indicative regions from the aggregate sequencing region to generate a sample population, the selected one or more indicative regions corresponding to a cancer presence in the test sample. The method applies a machine-learned model to the generated sample population to identify the cancer presence in the test sample. The machine-learned model identifies a candidate variant in an indicative region of the one or more selected indicative regions for the sample population, compares a test feature set of the candidate variant to a cohort feature set of a matching sequencing subregion from a cohort population, and determines the candidate variant is indicative of the cancer based on the compared test feature set and cohort feature set.

There are several methods for selecting, selecting the one or more indicative regions from the aggregate sequencing region for the sample population. In a first example, the method may calculate a first methylation beta series for a sequencing region in the aggregate sequencing region. The method calculates a second methylation beta series for a matching sequencing region from the cohort population, the matching sequencing region at a same genomic location as the sequencing region in the aggregate sequencing region. The method, for the sequencing region in the aggregate sequencing region, calculates a set of sequence changepoints in the sequencing region based on a difference between the first methylation beta series and the second methylation beta series. In some configurations, the set of sequence changepoints identify positions in the sequencing region for segmenting the sequencing region into a plurality of sequencing subregions, segmenting the sequencing region into the plurality of sequencing subregions at the identified positions of the set of sequence changepoints, and selecting one or more of the sequencing subregions of the plurality of sequencing subregions for the sample population. In some configurations, in aggregate across the plurality of sequencing subregions, the set of sequence changepoints maximizes a difference between the first methylation beta series for the sequencing region and the second methylation beta series for the matching sequencing region.

In another example of selecting the one or more indicative regions from the aggregate sequencing region for the sample population, the method calculates a methylation beta series for a matching sequencing region from the cohort population. The methylation beta series quantifies changes in methylation levels within sequencing regions, and the matching sequencing region is at a same location as a sequencing region from the aggregate sequencing region. The method, for the sequencing region in the aggregate sequencing region, calculates a set of sequence changepoints in the matching sequencing region based on the methylation beta series. The set of sequence changepoints identify positions in the matching sequencing region for segmenting the sequencing region into sequencing subregions. The method segments the sequencing region into a plurality of sequencing subregions at the identified positions of the set of sequence changepoints in the matching sequencing region, and selects one or more of the sequencing subregions of the plurality of sequencing subregions for the sample population.

In some configurations, in aggregate across the sequencing subregions, the set of sequence changepoints minimizes the methylation beta series for the cohort population.

In another example of selecting the one or more indicative regions from the aggregate sequencing region for the sample population the method identifies a plurality of CpGs in the aggregate sequencing region, each of the CpGs having a genomic length of a plurality of genomic lengths. The method segments the aggregate sequencing region into a plurality of sequencing subregions. Each of the sequencing subregions includes a subset of CpGs from the plurality of CpGs having substantially similar genomic lengths; and selecting one or more of the plurality of sequencing subregions for the sample population.

In another example of selecting the one or more indicative regions from the aggregate sequencing region for the sample population the method identifies a plurality of CpGs in the aggregate sequencing region; segmenting the aggregate sequencing region into a plurality of sequencing subregions. Each sequencing subregion of the plurality includes a number of CpGs less than a threshold number of CpGs; and selecting one or more of the plurality of sequencing subregions for the sample population.

In another example of selecting the one or more indicative regions from the aggregate sequencing region for the sample population the method identifies a plurality of CpGs in the aggregate sequencing region; identifying a plurality of CpG clusters using the identified plurality of CpG's, each CpG cluster including two or more CpGs less than a threshold genomic distance away from other CpGs in the cluster. The method segments the aggregate sequencing region into a plurality of sequencing subregions, wherein each of the sequencing subregion of the plurality includes a CpG cluster of the plurality of CpG clusters, and selects one or more of the plurality of sequencing subregions for the sample population. In some configurations, the sample population includes identifying CpG clusters having genomic locations overlapping with genomic locations of test sequences generated by a sequencing panel for the sample.

In another example of selecting the one or more indicative regions from the aggregate sequencing region for the sample population the method calculates a genomic length for each of the plurality of sequencing regions. The method, for each of the plurality of sequencing regions whose genomic length is greater than a threshold genomic length, segments the sequencing region into a plurality of sequencing subregions such that each of the plurality of sequencing subregions has a genomic length less than the threshold genomic length. The method selects, for the sample population, at least one the plurality of sequencing regions and at least one of the plurality of sequencing subregions.

In another example of selecting the one or more indicative regions from the aggregate sequencing region for the sample population the method identifies a number of CpGs in each sequencing region of the plurality of sequencing regions. The method, for each of the plurality of sequencing regions having a number of CpGs higher than a threshold number of CpGs, segments the sequencing region into a plurality of sequencing subregions such that each of the plurality of sequencing subregions includes less than the threshold number of CpGs. The method selects, for the sample population, at least one of the plurality of sequencing regions and at least one of the plurality of sequencing subregions.

In another example of selecting the one or more indicative regions from the aggregate sequencing region for the sample population the method generates a plurality of paired sequencing windows for the aggregate sequencing region. Each paired sequencing window including a sequencing region of the plurality of sequencing regions. A plurality of sequencing subregions generated from the sequencing region for each of the paired sequencing windows of the plurality identifying feature values for the sequencing region. The method identifies feature values for each of the plurality of sequencing subregions, and calculates, using the identified feature values, mutual information scores for each of the plurality of sequencing subregions and the sequencing region. The method selects, based on the mutual information scores, at least one of the plurality of sequencing subregions or the sequencing region for the sample population.

In another example of selecting the one or more indicative regions from the aggregate sequencing region for the sample population the method generates a plurality of paired sequencing windows for the aggregate sequencing region. Each paired sequencing window including a sequencing region of the plurality of sequencing regions and a plurality of sequence subregions generated from the sequencing region. The method generates an ensemble including a plurality of feature value sets. Each feature value set in the ensemble includes at least one feature value different from feature values of other feature value sets in the ensemble. The method, for each of the paired sequencing windows of the plurality, calculates, for each feature value set in the ensemble, mutual information scores for the sequencing region and each of the plurality of sequencing subregions, and selects, based on the mutual information scores, at least one of the plurality of sequencing subregions or the sequencing region for the sample population.

In some configurations selecting sequencing subregions and sequencing regions for the sample population is further based on a cancer classification metric across a classification matrix including a plurality of elements. The plurality of elements in the classification matrix may represent each possible combination of feature value sets from the ensemble, sequencing regions of the plurality, and sequencing subregions generated from sequencing regions.

Any of the steps in the preceding method may be implemented by one or more processors executing computer program code for executing those steps stored on a non-transitory computer-readable storage medium. The non-transitory computer-readable medium may be standalone or part of a system including the one or more processors responsible for executing that computer program code.

BRIEF DESCRIPTION OF DRAWINGS

FIG. 5A is an exemplary flowchart describing a process of training a cancer classifier, according to an example embodiment.

DETAILED DESCRIPTION

I. Overview

Figure 1A:
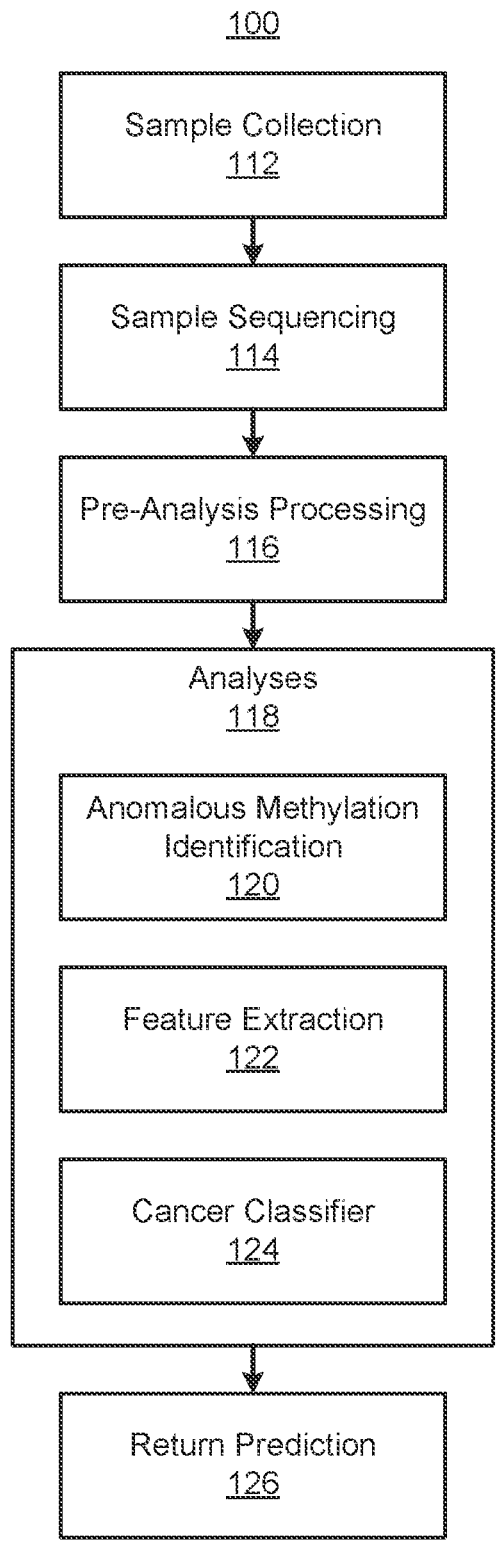
FIG. 1A is an exemplary flowchart describing an overall workflow of cancer classification of a sample, according to an example embodiment.

Early detection and classification of cancer is an important technology. Being able to detect cancer before it becomes symptomatic is beneficial to all parties involved, including patients, doctors, and loved ones. For patients, early cancer detection allows them a greater chance of a beneficial outcome; for doctors, early cancer detection allows more pathways of treatment that may lead to beneficial outcome; for loved ones, early cancer detection increases the likelihood of not losing their friends and family to the disease.

Recently, early cancer detection technology has progressed towards analyzing genetic fragments (e.g., DNA) in a person's, for example, blood to determine if any of those genetic fragments originate from cancer cells. These new techniques allow doctors to identify a cancer presence in a patient that may not be detectable otherwise. For instance, consider the example of a person at high risk for breast cancer. Traditionally, this person will regularly visit their doctor for a mammogram, which creates an image of their breast tissue (e.g., taking x-ray images) that a doctor uses to identify cancerous tissue. Unfortunately, with even the highest resolution mammograms, doctors are only able to identify tumors once they are approximately a millimeter in size. This means that the cancer has been present for some time in the person. This type of visual determination is typical for most cancers—that is, only being identifiable once it has grown to a sufficient size and identifiable with some sort of imaging technology.

Cancer detection using analysis of DNA fragment in a patient's, for example, blood alleviates this issue. To illustrate, cancer cells will start sloughing DNA fragments into a person's bloodstream as soon as they form. This occurs when there are very few of the cancer cells, and before they would be visible with imaging techniques. With the appropriate methods, therefore, a system that analyzes DNA fragments in the bloodstream could identify cancer presence in a person before it would be identifiable with more traditional cancer detection techniques.

Cancer detection based on the analysis of DNA fragments is enabled by next-generation sequencing ("NGS") techniques. NGS, broadly, is group of technologies that allows for high throughput sequencing of genetic material. As discussed in greater detail herein, NGS largely consists of sample preparation, DNA sequencing, and data analysis. Sample preparation is the laboratory methods necessary to prepare DNA fragments for sequencing, sequencing is the process of reading the ordered nucleotides in the samples, and data analysis is processing and analyzing the genetic information in the sequencing data to identify cancer presence.

While these steps of NGS may help enable early cancer detection, they also introduce their own complex, detrimental problems to cancer detection and, therefore, any improvements to sample preparation, DNA sequencing, and/or data analysis results in an improvement to cancer detection technologies.

To illustrate, as an example, problems introduced in sample preparation include DNA sample quality, sample contamination, fragmentation bias, and accurate indexing, and remedying those problems would yield better genetic data for cancer detection. Similarly, problems introduced in sequencing include, for example, errors in accurate transcribing of fragments (e.g., reading an "A" instead of a "C", etc.), incorrect or difficult fragment assembly and overlap, disparate coverage uniformity, sequencing depth vs. cost vs. specificity, and insufficient sequencing length. Again, remedying any of these problems would yield improved genetic data for cancer detection.

The problems in data analysis are possibly the most daunting and complex. The introduced challenges stem from the vast amounts of data created by NGS sequencing techniques. The created genetic datasets are typically on the order of terabytes, and effectively analyzing that amount of data is both procedurally and computationally demanding. For instance, analyzing NGS sequencing involves several baseline processing steps such as, e.g., aligning reads to one another, aligning and mapping reads to a reference genome, identifying and calling variant genes, identifying and calling abnormally methylated genes, generating functional annotations, etc. Performing any of these processes on terabytes of genetic data is computationally expensive for even the most powerful of computer architectures, and completely impossible for a normal human mind. Additionally, with the genetic sequencing data derived from the error-prone processes of sample preparation and sequence reading, large portions of the resulting genetic data may be low-quality or unusable for cancer identification. For example, large amounts of the genetic data may include contaminated samples, transcription errors, mismatched regions, overrepresented regions, etc. and may be unsuitable for high accuracy cancer detection. Identifying and accounting for low quality genetic data across the vast amount of genetic data obtained from NGS sequencing is also procedurally and computationally rigorous to accomplish and is also not practically performable by a human mind. Overall, any process created that leads to more efficient processing of large array sequencing data would be an improvement to cancer detection using NGS sequencing.

Finally, and perhaps most importantly, accurate identification of anomalous DNA from NGS data to identify a cancer presence is also difficult. The algorithms need to compensate for, e.g., errors generated by sample preparation and sequencing, and must overcome the large-scale data analysis problems accompanying NGS techniques. That is, designing a machine learning model or models that enable early cancer detection based on next generation sequencing techniques must be configured to account for the problems that those techniques create. Some of those techniques and models are discussed hereinbelow.

One of the problems in creating and appropriately applying a cancer detection model is, as described above, the vast amount of sequencing data to which the model may be applied. For instance, consider a machine-learned model that is configured to identify cancer based on the methylation state of DNA at various genomic locations. The model, for instance, identifies cancer because abnormal methylation at a first genomic site indicates cancer, abnormal methylation at a second genomic site indicates cancer, abnormal methylation at a third genomic site does not indicate cancer, etc. Given the traditional sample size of fragment-based cancer detection, this generally leads to tens of thousands of genomic sites indicative of cancer. For the machine learned model to process that amount of data is computationally expensive.

One method to alleviate this complexity and corresponding computational expense is to select genomic sites for processing by the model that are "strongly" associated with cancer. For instance, consider again the example machine-learned model trained to identify cancer based on methylation described above. In this instance, however, each indicative genomic site is also associated with a "strength" of cancer indication for that site. That is, abnormal methylation at the first site may strongly indicate cancer, while abnormal methylation at a second site may less strongly, or weakly, indicate cancer, etc. In this case, having the machine-learned model process genomic sites that are merely "weakly" indicative of cancer introduces computational expense without providing a corresponding benefit to the accuracy or specificity in cancer determination.

To provide a quantitative example, applying the machine-learned model to 100 weakly indicative sites may not provide as much benefit as applying the machine-learned model to 1 strongly indicative site. As such, selecting the appropriate "windows" of genomic areas for processing by a machine-learned model to identify cancer presence (e.g., selecting genomic regions that are indicative or not indicative of cancer, selecting genomic regions that show a correlation to cancer presence or cancer non-presence, etc.) greatly reduces processing cost without greatly reducing the accuracy or specificity of the model. In effect, it may lessen the analytical load from, e.g., millions of genomic sites to tens of thousands of genomic sites without sacrificing model accuracy. More succinctly, reducing the analytical load from millions of genomic sites to tens of thousands of sites, reduces the processing load and processing time by several orders of magnitude. This reduction reduced the monetary cost of such systems, enabling faster cancer detections and more importantly, freeing up computer resources for other models and classifications, improving the performance of the computer implementing the model, and improving the fields of public health, medicine, diagnostics, treatment, etc. by detecting cancer earlier than even possible by conventional methods.

Another problem associated with the vast amounts of data generated by NGS sequencing is appropriately training a machine-learned model to identify cancer within the large amount of data. For instance, a machine-learned model may be trained to identify cancer by comparing a feature vector to genomic data. The "features" in the feature vector, as set forth below, may be any genomic site with a sufficient depth of abnormally methylated genomic locations that correspond to cancer presence. When building feature vectors across an entire genome, this can lead to, typically, tens of thousands of features, and, as laid out above, some of those features may be more indicative of cancer presence than others. With this context, selecting which features and corresponding genomic data to use in training a machine learned model is difficult. The machine-learned model should be trained and configured to accurately identify cancer presence, but the resulting model should not be overly expensive computationally. In other words, appropriately selecting data and features for training a machine-learned model improves early cancer-detection.

I.A. Overview of Cancer Classification Workflow

FIG. 1 is an exemplary flowchart describing an overall workflow 100 of cancer classification of a sample, according to an example embodiment. The workflow 100 is by one or more entities, e.g., including a healthcare provider, a sequencing device, an analytics system 130, etc. Objectives of the workflow include detecting and/or monitoring cancer in individuals. From a healthcare standpoint, the workflow 100 can serve to supplement other existing cancer diagnostic tools. The workflow 100 may serve to provide early cancer detection and/or routine cancer monitoring to better inform treatment plans for individuals diagnosed with cancer. The overall workflow 100 may include additional/fewer steps than those shown in FIG. 1.

A healthcare provider performs sample collection 112. An individual to undergo cancer classification visits their healthcare provider. The healthcare provider collects the sample for performing cancer classification. Examples of biological samples include, but are not limited to, tissue biopsy, blood, whole blood, plasma, serum, urine, cerebrospinal fluid, fecal, saliva, sweat, tears, pleural fluid, pericardial fluid, or peritoneal fluid of the subject. The sample includes genetic material belonging to the individual, which may be extracted and sequenced for cancer classification. Once the sample is collected, the sample can be provided to a sequencing device. Along with the sample, the healthcare provider may collect other information relating to the individual, e.g., biological sex, age, ethnicity, smoking status, any prior diagnoses, etc.

A sequencing device performs sample sequencing 114. A lab clinician may perform one or more processing steps to the sample in preparation of sequencing. Once prepared, the clinician loads the sample in the sequencing device. An example of devices utilizes in sequencing is further described in conjunction with FIGS. 1B & 1C. The sequencing device generally extracts and isolates fragments of nucleic acid that are sequenced to determine a sequence of nucleobases corresponding to the fragments. Sample sequencing can include sample treatment in preparation for sequencing of the fragments in the sample. Sample treatment may include one or more ligation steps, and amplification of the nucleic acid material. In one or more embodiments, the sample treatment includes ligation of a sample barcode and unique molecule identifiers that may be utilized in contamination detection. The sample barcode can be a polynucleotide sequence that is substantially unique to each sample. The sample barcode can be ligated onto each fragment in a sample prior to indexing and sequencing. The unique molecule identifiers can also be polynucleotide sequences that are ligated onto each fragment originating in the sample, e.g., prior to amplification. The unique molecule identifiers may be utilized in de-duping sequence reads to identify unique fragments originating in the sample. Further description of sample sequencing 114 is described in FIGS. 2-5.

Different sequencing processes can include Sanger sequencing, fragment analysis, and next-generation sequencing. Sequencing may be whole-genome sequencing or targeted sequencing with a target panel. In context of DNA methylation, bisulfite sequencing (e.g., further described in FIGS. 2 & 7) can determine methylations status through bisulfite conversion of unmethylated cytosines at CpG sites. Sample sequencing 114 yields sequences for a plurality of nucleic acid fragments in the sample. In one or more embodiments, the sequences may include methylation state vectors, wherein each methylation state vector describes the methylation statuses for CpG sites on a fragment.

An analytics system 130 performs pre-analysis processing 116. An example analytics system 130 is described in FIG. 1C. Pre-analysis processing 116 may include, but not limited to, demultiplexing, de-duplication of sequence reads, determining metrics relating to coverage, identification of contamination events, determining whether the sample is contaminated, remedial measures to contamination events, calling sequencing error, performing remedial measures, etc. As a result of the pre-analysis processing 116, the analytics system 130 collects a set of sequence reads pertaining to the sample usable for the analyses 118.

The analytics system 130 performs one or more analyses 118. The analyses can be statistical analyses or application of one or more trained models to predict at least a cancer status of the individual from whom the sample is derived. Different genetic features may be evaluated and considered, such as methylation of CpG sites, single nucleotide polymorphisms (SNPs), insertions or deletions (indels), other types of genetic mutation, etc. In context of methylation, analyses 118 may include anomalous methylation identification 120 (e.g., further described in FIGS. 4A & 4B), feature extraction 122 (e.g., further described in FIGS. 5A and 5B), and applying a cancer classifier 146 to determine a cancer prediction (e.g., further described in FIGS. 5A & 5B). In one or more embodiments of feature extraction, the analytics system 130 may utilize one or more age covariate prediction models to generate one or more age covariate residuals as features to cancer classification. The cancer classifier 146 inputs the extracted features to determine a cancer prediction. The cancer prediction may be a label or a value. The label may indicate a particular cancer state, e.g., binary labels can indicate presence or absence of cancer, multiclass labels can indicate one or more cancer types from a plurality of cancer types that are screened for. The value may indicate a likelihood of a particular cancer state, e.g., a likelihood of cancer, and/or a likelihood of a particular cancer type.

The analytics system 130 returns the prediction 126 to the healthcare provider. The healthcare provider may establish or adjust a treatment plan based on the cancer prediction.

I.B. Overview of Methylation

In accordance with the present description, cfDNA fragments from an individual are treated, for example by converting unmethylated cytosines to uracils, sequenced and the sequence reads compared to a reference genome to identify the methylation states at specific CpG sites within the DNA fragments. Each CpG site may be methylated or unmethylated. Identification of anomalously methylated fragments, in comparison to healthy individuals, may provide insight into a subject's cancer status. DNA methylation anomalies (compared to healthy controls) can cause different effects, which may contribute to cancer. Various challenges arise in the identification of anomalously methylated cfDNA fragments. First off, determining a DNA fragment to be anomalously methylated can hold weight in comparison with a group of control individuals, such that if the control group is small in number, the determination loses confidence due to statistical variability within the smaller size of the control group. Additionally, among a group of control individuals, methylation status can vary which can be difficult to account for when determining a subject's DNA fragments to be anomalously methylated. On another note, methylation of a cytosine at a CpG site can causally influence methylation at a subsequent CpG site. To encapsulate this dependency can be another challenge in itself.

Methylation can typically occur in deoxyribonucleic acid (DNA) when a hydrogen atom on the pyrimidine ring of a cytosine base is converted to a methyl group, forming 5-methylcytosine. In particular, methylation can occur at dinucleotides of cytosine and guanine referred to herein as "CpG sites". In other instances, methylation may occur at a cytosine not part of a CpG site or at another nucleotide that is not cytosine; however, these are rarer occurrences. In this present disclosure, methylation is discussed in reference to CpG sites for the sake of clarity. Anomalous DNA methylation can be identified as hypermethylation or hypomethylation, both of which may be indicative of cancer status. Throughout this disclosure, hypermethylation and hypomethylation can be characterized for a DNA fragment, if the DNA fragment comprises more than a threshold number of CpG sites with more than a threshold percentage of those CpG sites being methylated or unmethylated.

The principles described herein can be equally applicable for the detection of methylation in a non-CpG context, including non-cytosine methylation. In such embodiments, the wet laboratory assay used to detect methylation may vary from those described herein. Further, the methylation state vectors discussed herein may contain elements that are generally sites where methylation has or has not occurred (even if those sites are not CpG sites specifically). With that substitution, the remainder of the processes described herein can be the same, and consequently the inventive concepts described herein can be applicable to those other forms of methylation.

I.C. Definitions

The term "cell free nucleic acid" or "cfNA" refers to nucleic acid fragments that circulate in an individual's body (e.g., blood) and originate from one or more healthy cells and/or from one or more unhealthy cells (e.g., cancer cells). The term "cell free DNA," or "cfDNA" refers to deoxyribonucleic acid fragments that circulate in an individual's body (e.g., blood). Additionally, cfNAs or cfDNA in an individual's body may come from other non-human sources.

The term "genomic nucleic acid," "genomic DNA," or "gDNA" refers to nucleic acid molecules or deoxyribonucleic acid molecules obtained from one or more cells. In various embodiments, gDNA can be extracted from healthy cells (e.g., non-tumor cells) or from tumor cells (e.g., a biopsy sample). In some embodiments, gDNA can be extracted from a cell derived from a blood cell lineage, such as a white blood cell.

The term "circulating tumor DNA" or "ctDNA" refers to nucleic acid fragments that originate from tumor cells or other types of cancer cells, and which may be released into a bodily fluid of an individual (e.g., blood, sweat, urine, or saliva) as result of biological processes such as apoptosis or necrosis of dying cells or actively released by viable tumor cells.

The term "DNA fragment," "fragment," or "DNA molecule" may generally refer to any deoxyribonucleic acid fragments, i.e., cfDNA, gDNA, ctDNA, etc.

The term "NA fragment," or "NA molecule" may generally refer to any nucleic acid molecule, including DNA molecules and ribonucleic acid (RNA) molecules.

The term "anomalous fragment," "anomalously methylated fragment," or "fragment with an anomalous methylation pattern" refers to a fragment that has anomalous methylation of CpG sites. Anomalous methylation of a fragment may be determined using probabilistic models to identify unexpectedness of observing a fragment's methylation pattern in a control group.

The term "unusual fragment with extreme methylation" or "UFXM" refers to a hypomethylated fragment or a hypermethylated fragment. A hypomethylated fragment and a hypermethylated fragment refers to a fragment with at least some number of CpG sites (e.g., 5) that have over some threshold percentage (e.g., 90%) of methylation or unmethylation, respectively.

The term "anomaly score" refers to a score for a CpG site based on a number of anomalous fragments (or, in some embodiments, UFXMs) from a sample overlaps that CpG site. The anomaly score is used in context of featurization of a sample for classification.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. The term "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

As used herein, the term "biological sample," "patient sample," or "sample" refers to any sample taken from a subject, which can reflect a biological state associated with the subject, and that includes cell-free DNA. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. A biological sample can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map nucleic acid fragment sequences obtained from sequencing a sample from the subject. A reference genome can refer to a haploid or diploid genome to which nucleic acid fragment sequences from the biological sample and a constitutional sample can be aligned and compared. An example of a constitutional sample can be DNA of white blood cells obtained from the subject. For a haploid genome, there can be one nucleotide at each locus. For a diploid genome, heterozygous loci can be identified; each heterozygous locus can have two alleles, where either allele can allow a match for alignment to the locus.

As used herein, the term "cancer" or "tumor" refers to an abnormal mass of tissue in which the growth of the mass surpasses and is not coordinated with the growth of normal tissue.

As used herein, the phrase "healthy," refers to a subject possessing good health. A healthy subject can demonstrate an absence of any malignant or non-malignant disease. A "healthy individual" can have other diseases or conditions, unrelated to the condition being assayed, which can normally not be considered "healthy."

As used herein, the term "variant" or "true variant" refers to a mutated nucleotide base at a position in the genome. Such a variant can lead to the development and/or progression of cancer in an individual.

As used herein, the term "candidate variant," "called variant," "putative variant," or refers to one or more detected nucleotide variants of a nucleotide sequence, for example, at a position in the genome that is determined to be mutated. Generally, a nucleotide base is deemed a called variant based on the presence of an alternative allele on sequence reads obtained from a sample, where the sequence reads each cross over the position in the genome. The source of a candidate variant can initially be unknown or uncertain. During processing, candidate variants can be associated with an expected source such as gDNA (e.g., blood-derived) or cells impacted by cancer (e.g., tumor-derived). Additionally, candidate variants can be called as true positives.

The term "non-edge variant" refers to a candidate variant that is not determined to be resulting from an artifact process, e.g., using an edge variant filtering method described herein. In some scenarios, a non-edge variant may not be a true variant (e.g., mutation in the genome) as the non-edge variant could arise due to a different reason as opposed to one or more artifact processes.

As used herein, the term "methylation" refers to a modification of deoxyribonucleic acid (DNA) where a hydrogen atom on the pyrimidine ring of a cytosine base is converted to a methyl group, forming 5-methylcytosine. In particular, methylation tends to occur at dinucleotides of cytosine and guanine referred to herein as "CpG sites." In other instances, methylation may occur at a cytosine not part of a CpG site or at another nucleotide that's not cytosine; however, these are rarer occurrences. Anomalous cfDNA methylation can be identified as hypermethylation or hypomethylation, both of which may be indicative of cancer status. DNA methylation anomalies (compared to healthy controls) can cause different effects, which may contribute to cancer. The principles described herein are equally applicable for the detection of methylation in a CpG context and non-CpG context, including non-cytosine methylation. Further, the methylation state vectors may contain elements that are generally vectors of sites where methylation has or has not occurred (even if those sites are not CpG sites specifically).

As used interchangeably herein, the term "methylation fragment" or "nucleic acid methylation fragment" refers to a sequence of methylation states for each CpG site in a plurality of CpG sites, determined by a methylation sequencing of nucleic acids (e.g., a nucleic acid molecule and/or a nucleic acid fragment). In a methylation fragment, a location and methylation state for each CpG site in the nucleic acid fragment is determined based on the alignment of the sequence reads (e.g., obtained from sequencing of the nucleic acids) to a reference genome. A nucleic acid methylation fragment comprises a methylation state of each CpG site in a plurality of CpG sites (e.g., a methylation state vector), which specifies the location of the nucleic acid fragment in a reference genome (e.g., as specified by the position of the first CpG site in the nucleic acid fragment using a CpG index, or another similar metric) and the number of CpG sites in the nucleic acid fragment. Alignment of a sequence read to a reference genome, based on a methylation sequencing of a nucleic acid molecule, can be performed using a CpG index. As used herein, the term "CpG index" refers to a list of each CpG site in the plurality of CpG sites (e.g., CpG 1, CpG 2, CpG 3, etc.) in a reference genome, such as a human reference genome, which can be in electronic format. The CpG index further comprises a corresponding genomic location, in the corresponding reference genome, for each respective CpG site in the CpG index. Each CpG site in each respective nucleic acid methylation fragment is thus indexed to a specific location in the respective reference genome, which can be determined using the CpG index.

As used herein, the term "true positive" (TP) refers to a subject having a condition. "True positive" can refer to a subject that has a tumor, a cancer, a pre-cancerous condition (e.g., a pre-cancerous lesion), a localized or a metastasized cancer, or a non-malignant disease. "True positive" can refer to a subject having a condition and is identified as having the condition by an assay or method of the present disclosure. As used herein, the term "true negative" (TN) refers to a subject that does not have a condition or does not have a detectable condition. True negative can refer to a subject that does not have a disease or a detectable disease, such as a tumor, a cancer, a pre-cancerous condition (e.g., a pre-cancerous lesion), a localized or a metastasized cancer, a non-malignant disease, or a subject that is otherwise healthy. True negative can refer to a subject that does not have a condition or does not have a detectable condition, or is identified as not having the condition by an assay or method of the present disclosure.

As used herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). In some embodiments, sequence reads (e.g., single-end or paired-end reads) can be generated from one or both strands of a targeted nucleic acid fragment. The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about bp, about 90 bp, about 95 bp, about 100 bp, about 112 bp, about 114 bp, about 116, about 118 bp, about 126 bp, about 200 bp, about 450 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 126) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the terms "sequencing" and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As used herein, the term "sequencing depth," is interchangeably used with the term "coverage" and refers to the number of times a locus is covered by a consensus sequence read corresponding to a unique nucleic acid target molecule aligned to the locus; e.g., the sequencing depth is equal to the number of unique nucleic acid target molecules covering the locus. The locus can be as small as a nucleotide, or as large as a chromosome arm, or as large as an entire genome. Sequencing depth can be expressed as "Yx", e.g., 50×, 100×, etc., where "Y" refers to the number of times a locus is covered with a sequence corresponding to a nucleic acid target; e.g., the number of times independent sequence information is obtained covering the particular locus. In some embodiments, the sequencing depth corresponds to the number of genomes that have been sequenced. Sequencing depth can also be applied to multiple loci, or the whole genome, in which case Y can refer to the mean or average number of times a locus or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

As used herein, the term "sensitivity" or "true positive rate" (TPR) refers to the number of true positives divided by the sum of the number of true positives and false negatives. Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

As used herein, the term "specificity" or "true negative rate" (TNR) refers to the number of true negatives divided by the sum of the number of true negatives and false positives. Specificity can characterize the ability of an assay or method to correctly identify a proportion of the population that truly does not have a condition. For example, specificity can characterize the ability of a method to correctly identify the number of subjects within a population not having cancer. In another example, specificity characterizes the ability of a method to correctly identify one or more markers indicative of cancer.

As used herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale, and shark. In some embodiments, a subject is a male or female of any stage (e.g., a man, a woman or a child). A subject from whom a sample is taken, or is treated by any of the methods or compositions described herein can be of any age and can be an adult, infant or child.

As used herein, the term "tissue" can correspond to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother vs. fetus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

As used herein, the term "genomic" refers to a characteristic of the genome of an organism. Examples of genomic characteristics include, but are not limited to, those relating to the primary nucleic acid sequence of all or a portion of the genome (e.g., the presence or absence of a nucleotide polymorphism, indel, sequence rearrangement, mutational frequency, etc.), the copy number of one or more particular nucleotide sequences within the genome (e.g., copy number, allele frequency fractions, single chromosome or entire genome ploidy, etc.), the epigenetic status of all or a portion of the genome (e.g., covalent nucleic acid modifications such as methylation, histone modifications, nucleosome positioning, etc.), the expression profile of the organism's genome (e.g., gene expression levels, isotype expression levels, gene expression ratios, etc.).

The terminology used herein is for the purpose of describing particular cases only and is not intended to be limiting.

As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

I.D. Example Analytics System

Figure 1B:
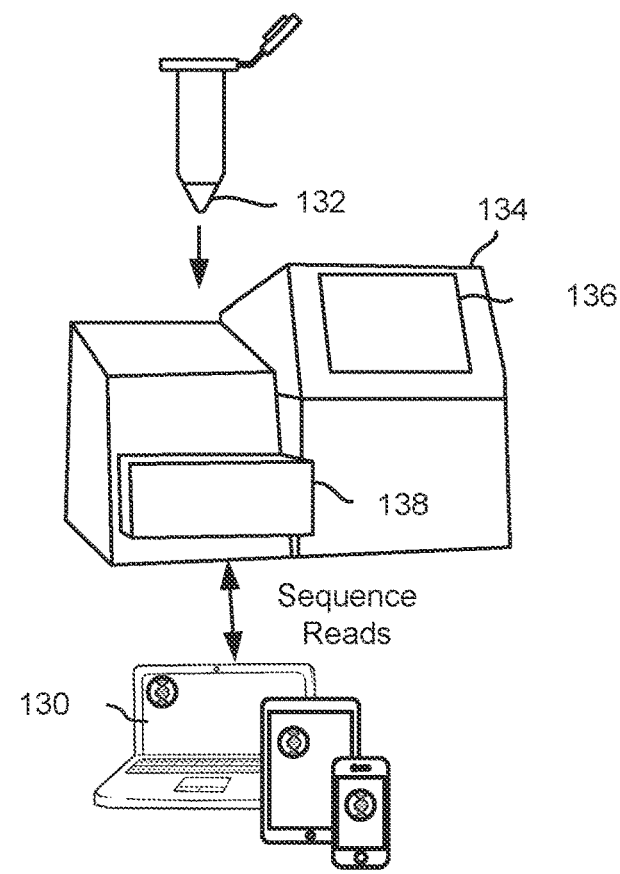
FIG. 1B illustrates an exemplary flowchart of devices for sequencing nucleic acid samples according to an example embodiment.

FIG. 1B is an exemplary flowchart of devices for sequencing nucleic acid samples according to an example embodiment. This illustrative flowchart includes devices such as a sequencer 134 and an analytics system 130. The sequencer 134 and the analytics system 130 may work in tandem to perform one or more steps in the processes 300 of FIG. 3A, 400 of FIG. 4A, 420 of FIG. 4B, and other process described herein.

In various embodiments, the sequencer 134 receives an enriched nucleic acid sample 132. As shown in FIG. 1B, the sequencer 134 can include a graphical user interface 136 that enables user interactions with particular tasks (e.g., initiate sequencing or terminate sequencing) as well as one more loading stations 134 for loading a sequencing cartridge including the enriched fragment samples and/or for loading buffers for performing the sequencing assays. Therefore, once a user of the sequencer 134 has provided the reagents and sequencing cartridge to the loading station 134 of the sequencer 134, the user can initiate sequencing by interacting with the graphical user interface 136 of the sequencer 134. Once initiated, the sequencer 134 performs the sequencing and outputs the sequence reads of the enriched fragments from the nucleic acid sample 132.

In some embodiments, the sequencer 134 is communicatively coupled with the analytics system 130. The analytics system 130 includes some number of computing devices used for processing the sequence reads for various applications such as assessing methylation status at one or more CpG sites, variant calling or quality control. The sequencer 134 may provide the sequence reads in a BAM file format to the analytics system 130. The analytics system 130 can be communicatively coupled to the sequencer 134 through a wireless, wired, or a combination of wireless and wired communication technologies. Generally, the analytics system 130 is configured with a processor and non-transitory computer-readable storage medium storing computer instructions that, when executed by the processor, cause the processor to process the sequence reads or to perform one or more steps of any of the methods or processes disclosed herein.

In some embodiments, the sequence reads may be aligned to a reference genome using known methods in the art to determine alignment position information. Alignment position may generally describe a beginning position and an end position of a region in the reference genome that corresponds to a beginning nucleotide based and an end nucleotide base of a given sequence read. Corresponding to methylation sequencing, the alignment position information may be generalized to indicate a first CpG site and a last CpG site included in the sequence read according to the alignment to the reference genome. The alignment position information may further indicate methylation statuses and locations of all CpG sites in a given sequence read. A region in the reference genome may be associated with a gene or a segment of a gene; as such, the analytics system 130 may label a sequence read with one or more genes that align to the sequence read.

In one embodiment, fragment length (or size) is be determined from the beginning and end positions.

In various embodiments, for example when a paired-end sequencing process is used, a sequence read is comprised of a read pair denoted as R_1 and R_2. For example, the first read R_1 may be sequenced from a first end of a double-stranded DNA (dsDNA) molecule whereas the second read R_2 may be sequenced from the second end of the double-stranded DNA (dsDNA). Therefore, nucleotide base pairs of the first read R_1 and second read R_2 may be aligned consistently (e.g., in opposite orientations) with nucleotide bases of the reference genome. Alignment position information derived from the read pair R_1 and R_2 may include a beginning position in the reference genome that corresponds to an end of a first read (e.g., R_1) and an end position in the reference genome that corresponds to an end of a second read (e.g., R_2). In other words, the beginning position and end position in the reference genome can represent the likely location within the reference genome to which the nucleic acid fragment corresponds. An output file having SAM (sequence alignment map) format or BAM (binary) format may be generated and output for further analysis.

Figure 1C:
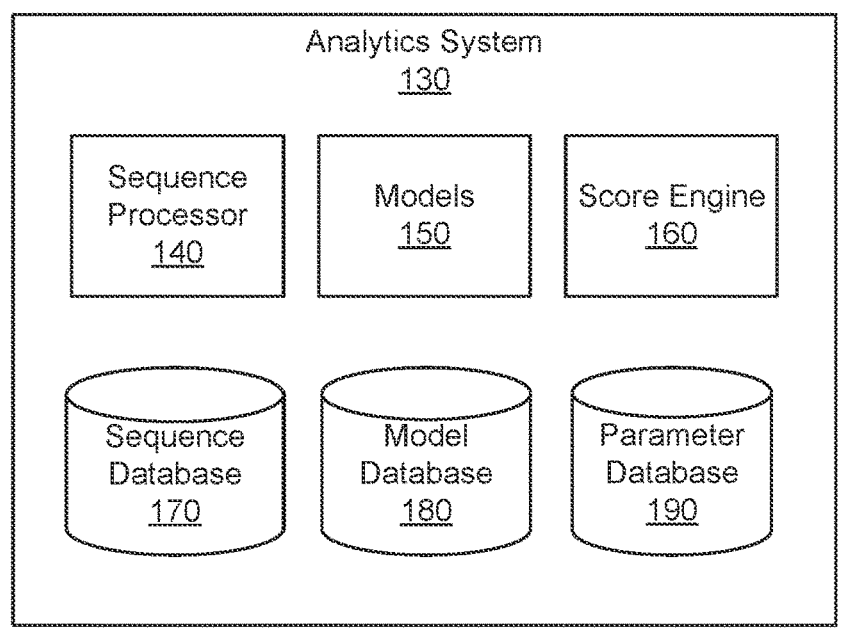
FIG. 1C is an exemplary block diagram of an analytics system 130, according to an example embodiment.

Referring now to FIG. 1C, FIG. 1C is a block diagram of an analytics system 130 for processing DNA samples according to one embodiment. The analytics system 130 implements one or more computing devices for use in analyzing DNA samples. The analytics system 130 includes a sequence processor 1040, sequence database 1045, model database 1055, models 1050, parameter database 1065, and score engine 1060. In some embodiments, the analytics system 130 performs some or all of the processes 300 of FIG. 3A and 400 of FIG. 4A.

The sequence processor 1040 generates methylation state vectors for fragments from a sample. At each CpG site on a fragment, the sequence processor 1040 generates a methylation state vector for each fragment specifying a location of the fragment in the reference genome, a number of CpG sites in the fragment, and the methylation state of each CpG site in the fragment whether methylated, unmethylated, or indeterminate via the process 300 of FIG. 3A. The sequence processor 1040 may store methylation state vectors for fragments in the sequence database 1045. Data in the sequence database 1045 may be organized such that the methylation state vectors from a sample are associated to one another.

Further, multiple different models 1050 may be stored in the model database 1055 or retrieved for use with test samples. In one example, a model is a trained cancer classifier for determining a cancer prediction for a test sample using a feature vector derived from anomalous fragments. The training and use of the cancer classifier will be further discussed in conjunction with Section III. Cancer Classifier for Determining Cancer. The analytics system 130 may train the one or more models 1050 and store various trained parameters in the parameter database 1065. The analytics system 130 stores the models 1050 along with functions in the model database 1055.

During inference, the score engine 1060 uses the one or more models 1050 to return outputs. The score engine 1060 accesses the models 1050 in the model database 1055 along with trained parameters from the parameter database 1065. According to each model, the score engine receives an appropriate input for the model and calculates an output based on the received input, the parameters, and a function of each model relating the input and the output. In some use cases, the score engine 1060 further calculates metrics correlating to a confidence in the calculated outputs from the model. In other use cases, the score engine 1060 calculates other intermediary values for use in the model.

II. Sample Sequencing & Processing

II.A. Generating Methylation State Vectors for DNA Fragments

Figure 2A:
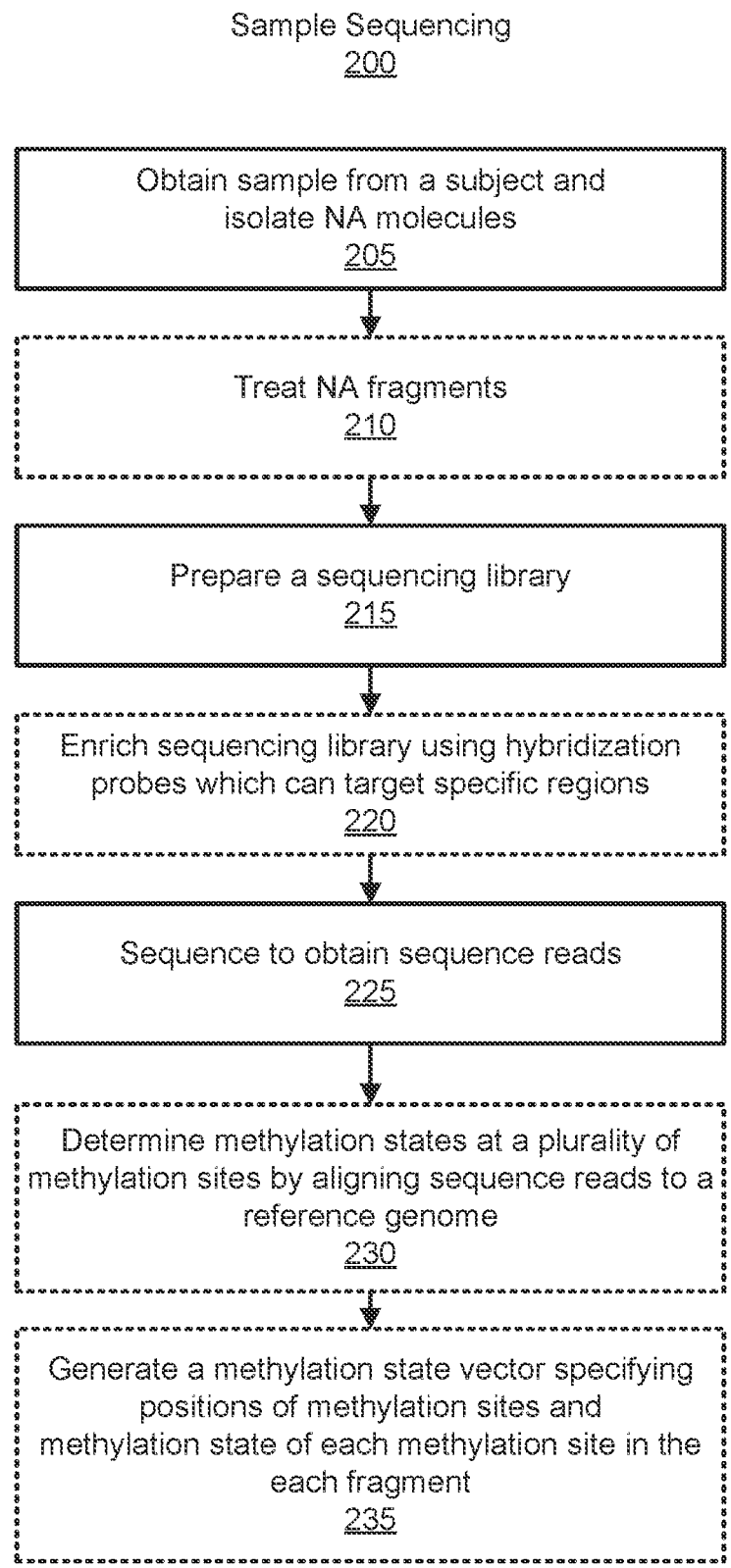
FIG. 2A is an exemplary flowchart describing a process of sequencing a fragment of cell-free (cf) DNA to obtain a methylation state vector, according to an example embodiment.

FIG. 2A is an exemplary flowchart describing a process 200 of sequencing a sample comprising nucleic acid (NA) fragment, according to an example embodiment. In order to analyze NA methylation, an analytics system 130 first obtains 205 a sample from an individual comprising a plurality of NA molecules. The process 200 may be applied to sequence many different types of NA molecules, e.g., DNA molecules, RNA molecules, cell-free DNA molecules, circulating-tumor DNA molecules, tissue DNA molecules, other types of NA molecules, etc. The process 200 is an embodiment of sample sequencing 114 of FIG. 1.

Generally, the sample sequencing process 200 comprises at least three steps. The analytics system 130 obtains 205 a sample from a subject comprising NA molecules and isolates the NA molecules. The sample may be any type of biological sample originating from an individual, which comprises NA molecules. For example, the sample could be a blood sample, a urine sample, a tissue sample, another type of biological sample, etc. The analytics system 130 prepares 215 a sequencing library that prepares the NA molecules for sequencing. Sequencing library preparation may include one or more ligation steps to add additional molecules used in the sequencing of the NA molecules, amplification of the NA molecules to create amplified molecules to ensure capture and sequencing of all NA molecules in the sample, enriching the sample by targeting specific genomic regions with targeting probes, ligation of one or more indices and one or more adaptors onto the NA molecules. Then the analytics system 130 sequences 225 the NA molecules to obtain sequence reads. The sequence reads may include forward reads and reverse reads.

In one or more embodiments of methylation sequencing, the analytics system 130 obtains 205 the sample comprising DNA fragments (e.g., cfDNA) and isolates each DNA fragment. The DNA fragments can be treated 210 prior to the sequencing. to convert unmethylated cytosines to uracils. In one embodiment, the method uses a bisulfite treatment of the DNA which converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, MA).

From the converted DNA fragments, a sequencing library can be prepared 215. During library preparation, unique molecular identifiers (UMI) can be added to the nucleic acid molecules (e.g., DNA molecules) through adapter ligation. The UMIs can be short nucleic acid sequences (e.g., 4-10 base pairs) that are added to ends of DNA fragments (e.g., DNA molecules fragmented by physical shearing, enzymatic digestion, and/or chemical fragmentation) during adapter ligation. UMIs can be degenerate base pairs that serve as a unique tag that can be used to identify sequence reads originating from a specific DNA fragment. During PCR amplification following adapter ligation, the UMIs can be replicated along with the attached DNA fragment. This can provide a way to identify sequence reads that came from the same original fragment in downstream analysis.

Optionally, the sequencing library may be enriched 220 for DNA fragments, or genomic regions, that are informative for cancer status using a plurality of hybridization probes. The hybridization probes are short oligonucleotides capable of hybridizing to particularly specified DNA fragments, or targeted regions, and enriching for those fragments or regions for subsequent sequencing and analysis. Hybridization probes may be used to perform a targeted, high-depth analysis of a set of specified CpG sites of interest to the researcher. Hybridization probes can be tiled across one or more target sequences at a coverage of 1×, 2×, 3×, 4×, 5×, 6×, 7×, 8×, 9×, 10×, or more than 10×. For example, hybridization probes tiled at a coverage of 2× comprises overlapping probes such that each portion of the target sequence is hybridized to 2 independent probes. Hybridization probes can be tiled across one or more target sequences at a coverage of less than 1×.

In one embodiment, the hybridization probes are designed to enrich for DNA molecules that have been treated (e.g., using bisulfite) for conversion of unmethylated cytosines to uracils. During enrichment, hybridization probes (also referred to herein as "probes") can be used to target and pull down nucleic acid fragments informative for the presence or absence of cancer (or disease), cancer status, or a cancer classification (e.g., cancer class or tissue of origin). The probes may be designed to anneal (or hybridize) to a target (complementary) strand of DNA. The target strand may be the "positive" strand (e.g., the strand transcribed into mRNA, and subsequently translated into a protein) or the complementary "negative" strand. The probes may range in length from 10s, 100s, or 1000s of base pairs. The probes can be designed based on a methylation site panel. The probes can be designed based on a panel of targeted genes to analyze particular mutations or target regions of the genome (e.g., of the human or another organism) that are suspected to correspond to certain cancers or other types of diseases. Moreover, the probes may cover overlapping portions of a target region.

Once prepared, the sequencing library or a portion thereof can be sequenced 225 to obtain a plurality of sequence reads. The sequence reads may be in a computer-readable, digital format for processing and interpretation by computer software. The sequence reads may be aligned to a reference genome to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene. A sequence read can be comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome can represent the likely location within the reference genome to which the nucleic acid fragment corresponds. An output file having SAM (sequence alignment map) format or BAM (binary) format may be generated and output for further analysis such as methylation state determination.

From the sequence reads, the analytics system 130 determines 230 a location and methylation state for each CpG site based on alignment to a reference genome. The analytics system 130 generates 235 a methylation state vector for each fragment specifying a location of the fragment in the reference genome (e.g., as specified by the position of the first CpG site in each fragment, or another similar metric), a number of CpG sites in the fragment, and the methylation state of each CpG site in the fragment whether methylated (e.g., denoted as M), unmethylated (e.g., denoted as U), or indeterminate (e.g., denoted as I). Observed states can be states of methylated and unmethylated; whereas, an unobserved state is indeterminate. Indeterminate methylation states may originate from sequencing errors and/or disagreements between methylation states of a DNA fragment's complementary strands. The methylation state vectors may be stored in temporary or persistent computer memory for later use and processing. Further, the analytics system 130 may remove duplicate reads or duplicate methylation state vectors from a single sample. The analytics system 130 may determine that a certain fragment with one or more CpG sites has an indeterminate methylation status over a threshold number or percentage, and may exclude such fragments or selectively include such fragments but build a model accounting for such indeterminate methylation statuses. FIG. 7 further illustrates the process 200 in methylation sequencing embodiments.

II.B. Methylation Sequencing

Figure 2B:
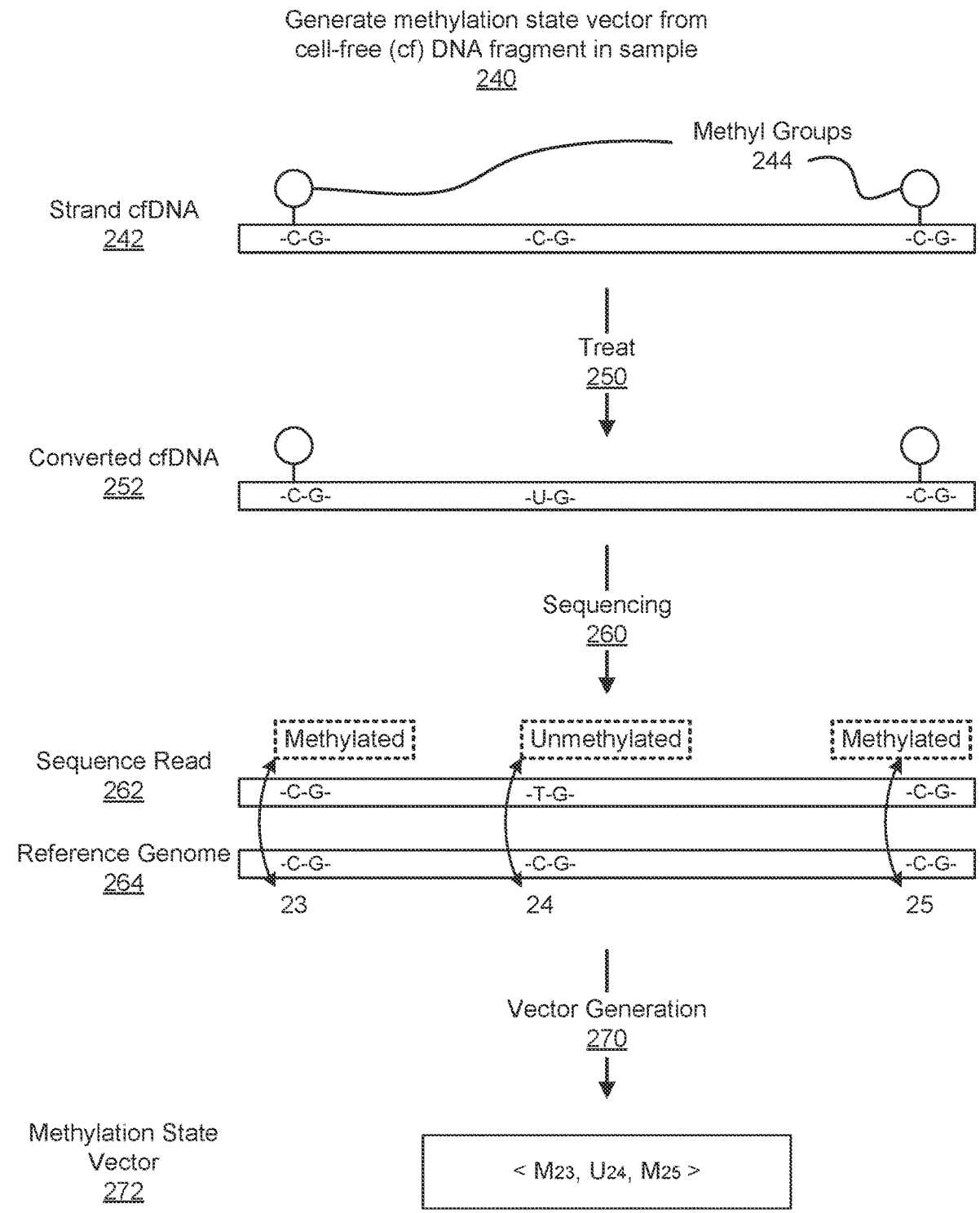
FIG. 2B is an exemplary illustration of the process of FIG. 2A of sequencing a fragment of cell-free (cf) DNA to obtain a methylation state vector, according to an example embodiment.

FIG. 2B is an exemplary illustration of methylation sequencing a cfDNA molecule to obtain a methylation state vector, according to an example embodiment. As an example, the analytics system 130 receives a cfDNA molecule 242 that, in this example, contains three CpG sites. As shown, the first and third CpG sites of the cfDNA molecule 242 are methylated 244. During the treatment step 250, the cfDNA molecule 242 is converted to generate a converted cfDNA molecule 252. During the treatment 250, the second CpG site which was unmethylated has its cytosine converted to uracil. However, the first and third CpG sites were not converted.

After conversion, a sequencing library is prepared and the molecule sequenced 260 to generate a sequence read 262. The analytics system 130 aligns the sequence read 262 to a reference genome 264. The reference genome 264 provides the context as to what position in a human genome the fragment cfDNA originates from. In this simplified example, the analytics system 130 aligns 270 the sequence read 262 such that the three CpG sites correlate to CpG sites 23, 24, and 25 (arbitrary reference identifiers used for convenience of description). The analytics system 130 can thus generate information both on methylation status of all CpG sites on the cfDNA molecule 242 and the position in the human genome that the CpG sites map to. As shown, the CpG sites on sequence read 262 which are methylated are read as cytosines. In this example, the cytosines appear in the sequence read 262 in the first and third CpG site which allows one to infer that the first and third CpG sites in the original cfDNA molecule are methylated. Whereas, the second CpG site can be read as a thymine (U is converted to T during the sequencing process), and thus, one can infer that the second CpG site is unmethylated in the original cfDNA molecule. With these two pieces of information, the methylation status and location, the analytics system 130 generates 270 a methylation state vector 272 for the fragment cfDNA 242. In this example, the resulting methylation state vector 272 is $<M_{23}, U_{24}, M_{25}>$, wherein M corresponds to a methylated CpG site, U corresponds to an unmethylated CpG site, and the subscript number corresponds to a position of each CpG site in the reference genome.

One or more alternative sequencing methods can be used for obtaining sequence reads from nucleic acids in a biological sample. The one or more sequencing methods can comprise any form of sequencing that can be used to obtain a number of sequence reads measured from nucleic acids (e.g., cell-free nucleic acids), including, but not limited to, high-throughput sequencing systems such as the Roche 454 platform, the Applied Biosystems SOLID platform, the Helicos True Single Molecule DNA sequencing technology, the sequencing-by-hybridization platform from Affymetrix Inc., the single-molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and Nanopore sequencing can also be used to obtain sequence reads from the nucleic acids (e.g., cell-free nucleic acids) in the biological sample. Sequencing-by-synthesis and reversible terminator-based sequencing (e.g., Illumina's Genome Analyzer; Genome Analyzer II; HISEQ 2000; HISEQ 4500 (Illumina, San Diego Calif)) can be used to obtain sequence reads from the cell-free nucleic acid obtained from a biological sample of a training subject in order to form the genotypic dataset. Millions of cell-free nucleic acid (e.g., DNA) fragments can be sequenced in parallel. In one example of this type of sequencing technology, a flow cell is used that contains an optically transparent slide with eight individual lanes on the surfaces of which are bound oligonucleotide anchors (e.g., adaptor primers). A cell-free nucleic acid sample can include a signal or tag that facilitates detection. The acquisition of sequence reads from the cell-free nucleic acid obtained from the biological sample can include obtaining quantification information of the signal or tag via a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

The one or more sequencing methods can comprise a whole-genome sequencing assay. A whole-genome sequencing assay can comprise a physical assay that generates sequence reads for a whole genome or a substantial portion of the whole genome which can be used to determine large variations such as copy number variations or copy number aberrations. Such a physical assay may employ whole-genome sequencing techniques or whole-exome sequencing techniques. A whole-genome sequencing assay can have an average sequencing depth of at least 1×, 2×, 3×, 4×, 5×, 6×, 7×, 8×, 9×, 10×, at least 20×, at least 30×, or at least 40× across the genome of the test subject. In some embodiments, the sequencing depth is about 30,000×. The one or more sequencing methods can comprise a targeted panel sequencing assay. A targeted panel sequencing assay can have an average sequencing depth of at least 50,000×, at least 55,000×, at least 60,000×, or at least 70,000× sequencing depth for the targeted panel of genes. The targeted panel of genes can comprise between 450 and 500 genes. The targeted panel of genes can comprise a range of 500±5 genes, a range of 500±10 genes, or a range of 500±25 genes.

The one or more sequencing methods can comprise paired-end sequencing. The one or more sequencing methods can generate a plurality of sequence reads. The plurality of sequence reads can have an average length ranging between 10 and 700, between 50 and 400, or between 100 and 300. The one or more sequencing methods can comprise a methylation sequencing assay. The methylation sequencing can be i) whole-genome methylation sequencing or ii) targeted DNA methylation sequencing using a plurality of nucleic acid probes. For example, the methylation sequencing is whole-genome bisulfite sequencing (e.g., WGBS). The methylation sequencing can be a targeted DNA methylation sequencing using a plurality of nucleic acid probes targeting the most informative regions of the methylome, a unique methylation database and prior prototype whole-genome and targeted sequencing assays.

The methylation sequencing can detect one or more 5-methylcytosine (5 mC) and/or 5-hydroxymethylcytosine (5 hmC) in respective nucleic acid methylation fragments. The methylation sequencing can comprise conversion of one or more unmethylated cytosines or one or more methylated cytosines, in respective nucleic acid methylation fragments, to a corresponding one or more uracils. The one or more uracils can be detected during the methylation sequencing as one or more corresponding thymines. The conversion of one or more unmethylated cytosines or one or more methylated cytosines can comprise a chemical conversion, an enzymatic conversion, or combinations thereof.

For example, bisulfite conversion involves converting cytosine to uracil while leaving methylated cytosines (e.g., 5-methylcytosine or 5-mC) intact. In some DNA, about 95% of cytosines may not methylated in the DNA, and the resulting DNA fragments may include many uracils which are represented by thymines. Enzymatic conversion processes may be used to treat the nucleic acids prior to sequencing, which can be performed in various ways. One example of a bisulfite-free conversion comprises a bisulfite-free and base-resolution sequencing method, TET-assisted pyridine borane sequencing (TAPS), for non-destructive and direct detection of 5-methylcytosine and 5-hydroxymethylcytosine without affecting unmodified cytosines. The methylation state of a CpG site in the corresponding plurality of CpG sites in the respective nucleic acid methylation fragment can be methylated when the CpG site is determined by the methylation sequencing to be methylated, and unmethylated when the CpG site is determined by the methylation sequencing to not be methylated.

A methylation sequencing assay (e.g., WGBS and/or targeted methylation sequencing) can have an average sequencing depth including but not limited to up to about 1,000×, 2,000×, 3,000×, 5,000×, 10,000×, 15,000×, 20,000×, or 30,000×. The methylation sequencing can have a sequencing depth that is greater than 30,000×, e.g., at least 40,000× or A whole-genome bisulfite sequencing method can have an average sequencing depth of between 20× and 50×, and a targeted methylation sequencing method has an average effective depth of between 100× and 1000×, where effective depth can be the equivalent whole-genome bisulfite sequencing coverage for obtaining the same number of sequence reads obtained by targeted methylation sequencing.

For further details regarding methylation sequencing (e.g., WGBS and/or targeted methylation sequencing), see, e.g., U.S. patent application Ser. No. 16/352,602, entitled "Methylation Fragment Anomaly Detection," filed Mar. 13, 2019, and U.S. patent application Ser. No. 16/719,902, entitled "Systems and Methods for Estimating Cell Source Fractions Using Methylation Information," filed Dec. 18, 2019, each of which is hereby incorporated by reference. Other methods for methylation sequencing, including those disclosed herein and/or any modifications, substitutions, or combinations thereof, can be used to obtain fragment methylation patterns. A methylation sequencing can be used to identify one or more methylation state vectors, as described, for example, in U.S. patent application Ser. No. 16/352,602, entitled "Anomalous Fragment Detection and Classification," filed Mar. 13, 2019, or in accordance with any of the techniques disclosed in U.S. patent application Ser. No. 15/931,022, entitled "Model-Based Featurization and Classification," filed May 13, 2020, each of which is hereby incorporated by reference.

The methylation sequencing of nucleic acids and the resulting one or more methylation state vectors can be used to obtain a plurality of nucleic acid methylation fragments. Each corresponding plurality of nucleic acid methylation fragments (e.g., for each respective genotypic dataset) can comprise more than 100 nucleic acid methylation fragments. An average number of nucleic acid methylation fragments across each corresponding plurality of nucleic acid methylation fragments can comprise 1000 or more nucleic acid methylation fragments, 5000 or more nucleic acid methylation fragments, 10,000 or more nucleic acid methylation fragments, 20,000 or more nucleic acid methylation fragments, or 30,000 or more nucleic acid methylation fragments. An average number of nucleic acid methylation fragments across each corresponding plurality of nucleic acid methylation fragments can be between 10,000 nucleic acid methylation fragments and 50,000 nucleic acid methylation fragments. The corresponding plurality of nucleic acid methylation fragments can comprise one thousand or more, ten thousand or more, 100 thousand or more, one million or more, ten million or more, 100 million or more, 500 million or more, one billion or more, two billion or more, three billion or more, four billion or more, five billion or more, six billion or more, seven billion or more, eight billion or more, nine billion or more, or 10 billion or more nucleic acid methylation fragments. An average length of a corresponding plurality of nucleic acid methylation fragments can be between 118 and 480 nucleotides.

Further details regarding methods for sequencing nucleic acids and methylation sequencing data are disclosed in U.S. patent application Ser. No. 17/191,914, titled "Systems and Methods for Cancer Condition Determination Using Autoencoders," filed Mar. 4, 2021, which is hereby incorporated herein by reference in its entirety.

III. Cancer Classifier for Determining Cancer

Cancer classification involves extraction genetic features and applying one or more models to the extracted features to determine a cancer prediction. The extracted features a feature vector for a test sample and determines a cancer prediction based on the input feature vector. The cancer prediction may comprise a label and/or a value. The label may be binary, indicating a presence or absence of cancer in the test subject, and/or multiclass, indicating one or more particular cancer types from a plurality of screened cancer types. In particular, a cancer classifier may be a machine-learned model comprising a plurality of classification parameters and a function representing a relation between the feature vector as input and the cancer prediction as output. Inputting the feature vector into the function with the classification parameters yields the cancer prediction. In one or more embodiments, an age covariate prediction model is used to predict an age of the test sample based on methylation features. A residual of the predicted age and a reported age of the test subject may be utilized as a feature in the cancer classifier. In one or more embodiments, the feature vectors input into the cancer classifier are based on set of anomalous fragments (also referred to as "anomalously methylated" or "unusual fragments of extreme methylation" (UFXM)) determined from the test sample. Prior to deployment of the cancer classifier, the analytics system 130 trains the cancer classifier.

III.A. Identifying Anomalous Fragments

The analytics system 130 can determine anomalous fragments for a sample using the sample's methylation state vectors. For each fragment in a sample, the analytics system 130 can determine whether the fragment is an anomalous fragment using the methylation state vector corresponding to the fragment. In some embodiments, the analytics system 130 calculates a p-value score for each methylation state vector describing a probability of observing that methylation state vector or other methylation state vectors even less probable in the healthy control group. The process for calculating a p-value score is further discussed below in Section III.D.i. P-Value Filtering. The analytics system 130 may determine fragments with a methylation state vector having below a threshold p-value score as anomalous fragments. In some embodiments, the analytics system 130 further labels fragments with at least some number of CpG sites that have over some threshold percentage of methylation or unmethylation as hypermethylated and hypomethylated fragments, respectively. A hypermethylated fragment or a hypomethylated fragment may also be referred to as an unusual fragment with extreme methylation (UFXM). In other embodiments, the analytics system 130 may implement various other probabilistic models for determining anomalous fragments. Examples of other probabilistic models include a mixture model, a deep probabilistic model, etc. In some embodiments, the analytics system 130 may use any combination of the processes described below for identifying anomalous fragments. With the identified anomalous fragments, the analytics system 130 may filter the set of methylation state vectors for a sample for use in other processes, e.g., for use in training and deploying a cancer classifier.

III.A.I P-Value Filtering

Figure 3A:
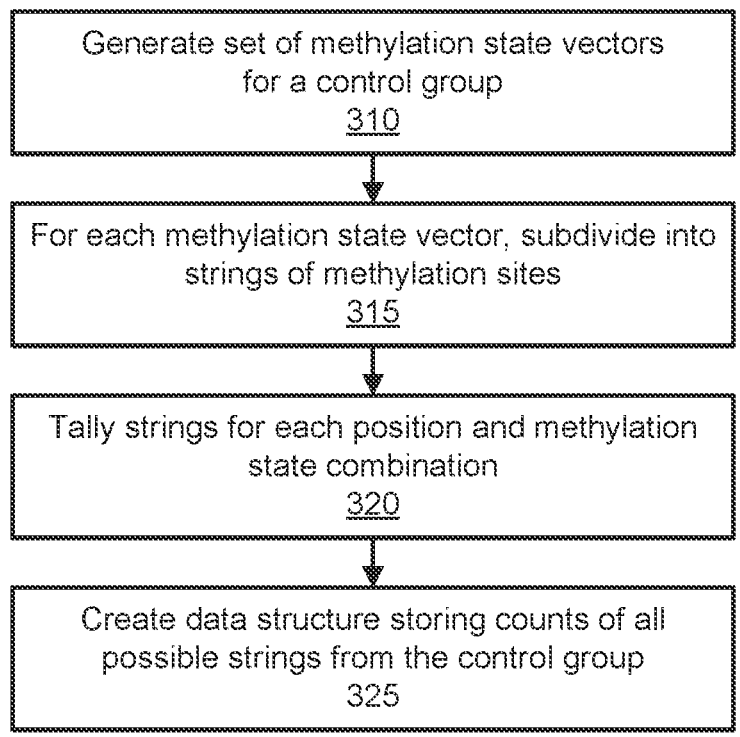
FIG. 3A is a flowchart describing a process 300A of generating a data structure for a healthy control group, according to an embodiment.
Figure 3B:
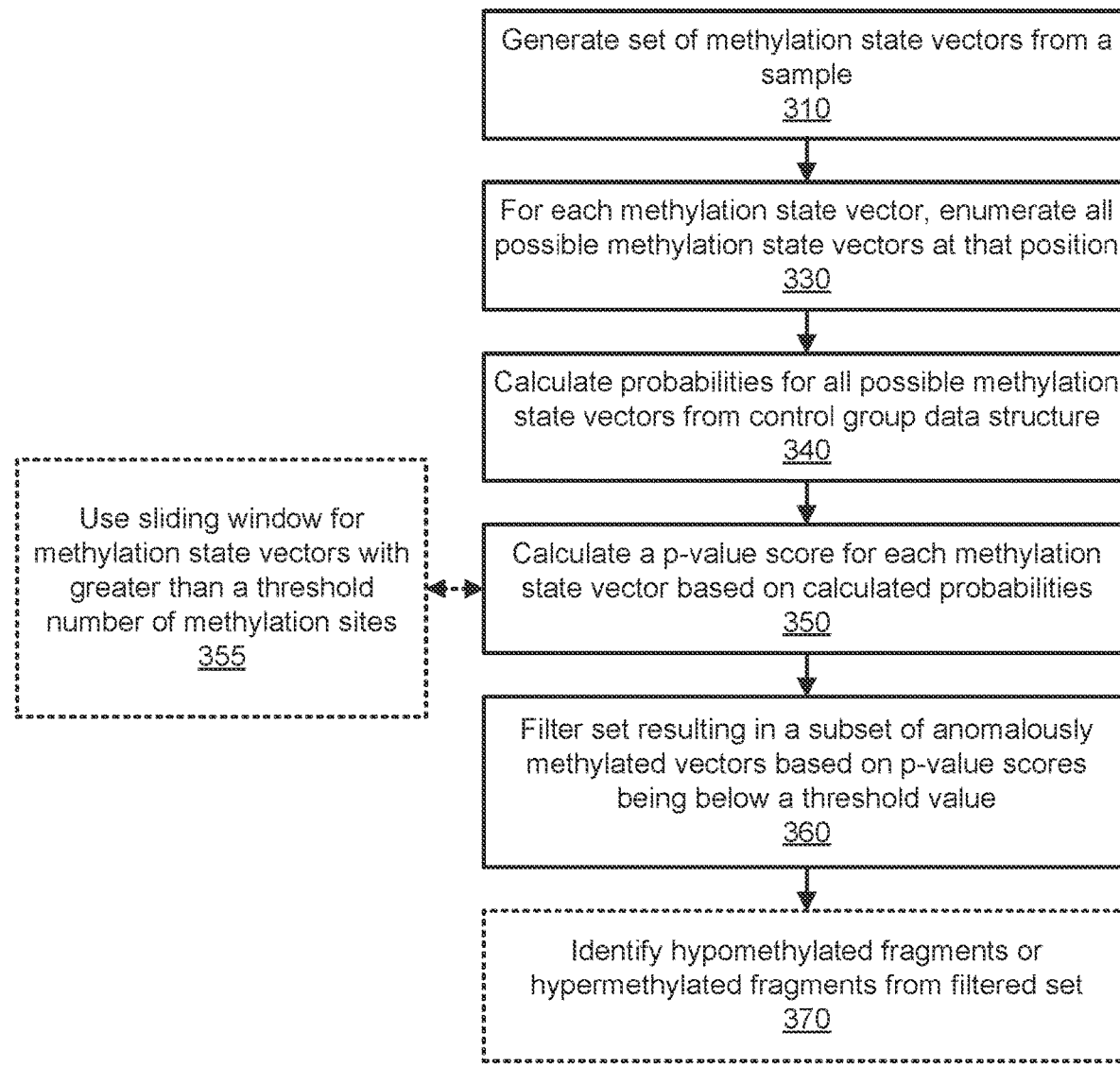
FIG. 3B is a flowchart describing a process 300B for identifying anomalously methylated fragments from an individual, according to an embodiment.

In some embodiments, the analytics system 130 calculates a p-value score for each methylation state vector compared to methylation state vectors from fragments in a healthy control group. The p-value score can describe a probability of observing the methylation status matching that methylation state vector or other methylation state vectors even less probable in the healthy control group. In order to determine a DNA fragment to be anomalously methylated, the analytics system 130 can use a healthy control group with a majority of fragments that are normally methylated. When conducting this probabilistic analysis for determining anomalous fragments, the determination can hold weight in comparison with the group of control subjects that make up the healthy control group. To ensure robustness in the healthy control group, the analytics system 130 may select some threshold number of healthy individuals to source samples including DNA fragments. FIG. 3A below describes the method of generating a data structure for a healthy control group with which the analytics system 130 may calculate p-value scores. FIG. 3B describes the method of calculating a p-value score with the generated data structure.

FIG. 3A is a flowchart describing a process 300A of generating a data structure for a healthy control group, according to an embodiment. To create a healthy control group data structure, the analytics system 130 can receive a plurality of DNA fragments (e.g., cfDNA) from a plurality of healthy individuals. The analytics system 130 identifies and generates 310 one or more methylation state vectors each fragment, for example via the process 200.

With each fragment's methylation state vector, the analytics system 130 can subdivide 315 the methylation state vector into strings of CpG sites (e.g., in the manner similar to step 205 of FIG. 2). In some embodiments, the analytics system 130 subdivides 205 the methylation state vector such that the resulting strings are all less than a given length. For example, a methylation state vector of length 11 may be subdivided into strings of length less than or equal to 3 would result in 9 strings of length 3, 10 strings of length 2, and 11 strings of length 1. In another example, a methylation state vector of length 7 being subdivided into strings of length less than or equal to x4 can result in x4 strings of length x4, 5 strings of length 3, 6 strings of length 2, and 7 strings of length 1. If a methylation state vector is shorter than or the same length as the specified string length, then the methylation state vector may be converted into a single string containing all of the CpG sites of the vector.

The analytics system 130 tallies 320 the strings by counting, for each possible CpG site and possibility of methylation states in the vector, the number of strings present in the control group having the specified CpG site as the first CpG site in the string and having that possibility of methylation states. For example, at a given CpG site and considering string lengths of 3, there are 2^3 or 8 possible string configurations. At that given CpG site, for each of the 8 possible string configurations, the analytics system 130 tallies 320 how many occurrences of each methylation state vector possibility come up in the control group. Continuing this example, this may involve tallying the following quantities: $<M_x, M_{x+1}, M_{x+2}>$, $<M_x, M_{x+1}, U_{x+2}>$, $<U_x, U_{x+1}, U_{x+2}>$ for each starting CpG site x in the reference genome. The analytics system 130 creates 325 the data structure storing the tallied counts for each starting CpG site and string possibility.

There are several benefits to setting an upper limit on string length. First, depending on the maximum length for a string, the size of the data structure created by the analytics system 130 can dramatically increase in size. For instance, maximum string length of x4 means that every CpG site has at the very least 2^4 numbers to tally for strings of length x4. Increasing the maximum string length to 5 means that every CpG site has an additional 2^4 or 16 numbers to tally, doubling the numbers to tally (and computer memory utilized) compared to the prior string length. Reducing string size can help keep the data structure creation and performance (e.g., use for later accessing as described below), in terms of computational and storage, reasonable. Second, a statistical consideration to limiting the maximum string length can be to avoid overfitting downstream models that use the string counts. If long strings of CpG sites do not, biologically, have a strong effect on the outcome (e.g., predictions of anomalousness that predictive of the presence of cancer), calculating probabilities based on large strings of CpG sites can be problematic as it uses a significant amount of data that may not be available, and thus can be too sparse for a model to perform appropriately. For example, calculating a probability of anomalousness/cancer conditioned on the prior 100 CpG sites can use counts of strings in the data structure of length 100, ideally some matching exactly the prior 100 methylation states. If sparse counts of strings of length 100 are available, there can be insufficient data to determine whether a given string of length of 100 in a test sample is anomalous or not.

FIG. 3B is a flowchart describing a process 300B for identifying anomalously methylated fragments from an individual, according to an embodiment. In process 300B, the analytics system 130 generates 310 methylation state vectors from cfDNA fragments of the subject, for example, in a manner similar to process 200. The analytics system 130 can handle each methylation state vector as follows.

For a given methylation state vector, the analytics system 130 enumerates 830 all possibilities of methylation state vectors having the same starting CpG site and same length (i.e., set of CpG sites) in the methylation state vector. As each methylation state is generally either methylated or unmethylated there can be effectively two possible states at each CpG site, and thus the count of distinct possibilities of methylation state vectors can depend on a power of 2, such that a methylation state vector of length n would be associated with $2^n$ possibilities of methylation state vectors. With methylation state vectors inclusive of indeterminate states for one or more CpG sites, the analytics system 130 may enumerate 330 possibilities of methylation state vectors considering CpG sites that have observed states.

The analytics system 130 calculates 340 the probability of observing each possibility of methylation state vector for the identified starting CpG site and methylation state vector length by accessing the healthy control group data structure. In some embodiments, calculating the probability of observing a given possibility uses a Markov chain probability to model the joint probability calculation. The Markov model can be trained, at least in part, based upon evaluation of a methylation state of each CpG site in the corresponding plurality of CpG sites of the respective fragment (e.g., nucleic acid methylation fragment) across those nucleic acid methylation fragments in a healthy noncancer cohort dataset that have the corresponding plurality of CpG sites. For example, a Markov model (e.g., a Hidden Markov Model or HMM) is used to determine the probability that a sequence of methylation states (comprising, e.g., "M" or "U") can be observed for a nucleic acid methylation fragment in a plurality of nucleic acid methylation fragments, given a set of probabilities that determine, for each state in the sequence, the likelihood of observing the next state in the sequence. The set of probabilities can be obtained by training the HMM. Such training can involve computing statistical parameters (e.g., the probability that a first state can transition to a second state (the transition probability) and/or the probability that a given methylation state can be observed for a respective CpG site (the emission probability)), given an initial training dataset of observed methylation state sequences (e.g., methylation patterns). HMIs can be trained using supervised training (e.g., using samples where the underlying sequence as well as the observed states are known) and/or unsupervised training (e.g., Viterbi learning, maximum likelihood estimation, expectation-maximization training, and/or Baum-Welch training). In other embodiments, calculation methods other than Markov chain probabilities are used to determine the probability of observing each possibility of methylation state vector. For example, such calculation method can include a learned representation. The p-value threshold can be between 0.01 and 0.10, or between 0.03 and 0.06. The p-value threshold can be 0.05. The p-value threshold can be less than 0.01, less than 0.001, or less than 0.0001.

The analytics system 130 calculates 350 a p-value score for the methylation state vector using the calculated probabilities for each possibility. In some emboidments, this includes identifying the calculated probability corresponding to the possibility that matches the methylation state vector in question. Specifically, this can be the possibility having the same set of CpG sites, or similarly the same starting CpG site and length as the methylation state vector. The analytics system 130 can sum the calculated probabilities of any possibilities having probabilities less than or equal to the identified probability to generate the p-value score.

This p-value can represent the probability of observing the methylation state vector of the fragment or other methylation state vectors even less probable in the healthy control group. A low p-value score can, thereby, generally correspond to a methylation state vector which is rare in a healthy individual, and which causes the fragment to be labeled anomalously methylated, relative to the healthy control group. A high p-value score can generally relate to a methylation state vector which is expected to be present, in a relative sense, in a healthy individual. If the healthy control group is a non-cancerous group, for example, a low p-value can indicate that the fragment is anomalous methylated relative to the non-cancer group, and therefore possibly indicative of the presence of cancer in the test subject.

As above, the analytics system 130 can calculate p-value scores for each of a plurality of methylation state vectors, each representing a cfDNA fragment in the test sample. To identify which of the fragments are anomalously methylated, the analytics system 130 may filter 360 the set of methylation state vectors based on their p-value scores. In some embodiments, filtering is performed by comparing the p-values scores against a threshold and keeping those fragments below the threshold. This threshold p-value score can be on the order of 0.1, 0.01, 0.001, 0.0001, or similar.

According to example results from the process 300A, the analytics system 130 can yield a median (range) of 2,800 (1,500-12,000) fragments with anomalous methylation patterns for participants without cancer in training, and a median (range) of 3,000 (1,200-420,000) fragments with anomalous methylation patterns for participants with cancer in training. These filtered sets of fragments with anomalous methylation patterns may be used for the downstream analyses as described below in Section III. For example, the analytics system 130 may identify 370 hypomethylated fragments or hypermethylated fragments from filtered set.

In some embodiments, the analytics system 130 uses 355 a sliding window to determine possibilities of methylation state vectors and calculate p-values. Rather than enumerating possibilities and calculating p-values for entire methylation state vectors, the analytics system 130 can enumerate possibilities and calculates p-values for a window of sequential CpG sites, where the window is shorter in length (of CpG sites) than at least some fragments (otherwise, the window would serve no purpose). The window length may be static, user determined, dynamic, or otherwise selected.

In calculating p-values for a methylation state vector larger than the window, the window can identify the sequential set of CpG sites from the vector within the window starting from the first CpG site in the vector. The analytic system can calculate a p-value score for the window including the first CpG site. The analytics system 130 can then "slide" the window to the second CpG site in the vector, and calculates another p-value score for the second window. Thus, for a window size/and methylation vector length m, each methylation state vector can generate m−l+1 p-value scores. After completing the p-value calculations for each portion of the vector, the lowest p-value score from all sliding windows can be taken as the overall p-value score for the methylation state vector. In other embodiments, the analytics system 130 aggregates the p-value scores for the methylation state vectors to generate an overall p-value score.

Using the sliding window can help to reduce the number of enumerated possibilities of methylation state vectors and their corresponding probability calculations that would otherwise be performed. To give a realistic example, it can be for fragments to have upwards of 54 CpG sites. Instead of computing probabilities for $2^{\wedge}4$ (~$1.8\times10^{\wedge}16$) possibilities to generate a single p-score, the analytics system 130 can instead use a window of size 5 (for example) which results in 50 p-value calculations for each of the 50 windows of the methylation state vector for that fragment. Each of the 50 calculations can enumerate $2^{\wedge}5$ (32) possibilities of methylation state vectors, which total results in $50\times2^{\wedge}5$ ($1.6\times10^{\wedge}3$) probability calculations. This can result in a vast reduction of calculations to be performed, with no meaningful hit to the accurate identification of anomalous fragments.

In embodiments with indeterminate states, the analytics system 130 may calculate a p-value score summing out CpG sites with indeterminates states in a fragment's methylation state vector. The analytics system 130 can identify all possibilities that have consensus with the all methylation states of the methylation state vector excluding the indeterminate states. The analytics system 130 may assign the probability to the methylation state vector as a sum of the probabilities of the identified possibilities. As an example, the analytics system 130 can calculate a probability of a methylation state vector of $<M_1, I_2, U_3>$ as a sum of the probabilities for the possibilities of methylation state vectors of $<M_1, M_2, U_3>$ and $<M_1, U_2, U_3>$ since methylation states for CpG sites 1 and 3 are observed and in consensus with the fragment's methylation states at CpG sites 1 and 3. This method of summing out CpG sites with indeterminate states can use calculations of probabilities of possibilities up to $2^{\wedge}i$, wherein i denotes the number of indeterminate states in the methylation state vector. In additional embodiments, a dynamic programming algorithm may be implemented to calculate the probability of a methylation state vector with one or more indeterminate states. Advantageously, the dynamic programming algorithm operates in linear computational time.

In some embodiments, the computational burden of calculating probabilities and/or p-value scores may be further reduced by caching at least some calculations. For example, the analytic system may cache in transitory or persistent memory calculations of probabilities for possibilities of methylation state vectors (or windows thereof). If other fragments have the same CpG sites, caching the possibility probabilities can allow for efficient calculation of p-score values without re-calculating the underlying possibility probabilities. Equivalently, the analytics system 130 may calculate p-value scores for each of the possibilities of methylation state vectors associated with a set of CpG sites from vector (or window thereof). The analytics system 130 may cache the p-value scores for use in determining the p-value scores of other fragments including the same CpG sites. Generally, the p-value scores of possibilities of methylation state vectors having the same CpG sites may be used to determine the p-value score of a different one of the possibilities from the same set of CpG sites.

One or more nucleic acid methylation fragments can be filtered prior to training region models or cancer classifier. Filtering nucleic acid methylation fragments can comprise removing, from the corresponding plurality of nucleic acid methylation fragments, each respective nucleic acid methylation fragment that fails to satisfy one or more selection criteria (e.g., below or above one selection criteria). The one or more selection criteria can comprise a p-value threshold. The output p-value of the respective nucleic acid methylation fragment can be determined, at least in part, based upon a comparison of the corresponding methylation pattern of the respective nucleic acid methylation fragment to a corresponding distribution of methylation patterns of those nucleic acid methylation fragments in a healthy noncancer cohort dataset that have the corresponding plurality of CpG sites of the respective nucleic acid methylation fragment.

Filtering a plurality of nucleic acid methylation fragments can comprise removing each respective nucleic acid methylation fragment that fails to satisfy a p-value threshold. The filter can be applied to the methylation pattern of each respective nucleic acid methylation fragment using the methylation patterns observed across the first plurality of nucleic acid methylation fragments. Each respective methylation pattern of each respective nucleic acid methylation fragment (e.g., Fragment One, . . . , Fragment N) can comprise a corresponding one or more methylation sites (e.g., CpG sites) identified with a methylation site identifier and a corresponding methylation pattern, represented as a sequence of 1's and 0's, where each "1" represents a methylated CpG site in the one or more CpG sites and each "0" represents an unmethylated CpG site in the one or more CpG sites. The methylation patterns observed across the first plurality of nucleic acid methylation fragments can be used to build a methylation state distribution for the CpG site states collectively represented by the first plurality of nucleic acid methylation fragments (e.g., CpG site A, CpG site B, CpG site ZZZ). Further details regarding processing of nucleic acid methylation fragments are disclosed in U.S. Provisional patent application Ser. No. 17/191,914, titled "Systems and Methods for Cancer Condition Determination Using Autoencoders," filed Mar. 4, 2021, which is hereby incorporated herein by reference in its entirety.

The respective nucleic acid methylation fragment may fail to satisfy a selection criterion in the one or more selection criteria when the respective nucleic acid methylation fragment has an anomalous methylation score that is less than an anomalous methylation score threshold. In this situation, the anomalous methylation score can be determined by a mixture model. For example, a mixture model can detect an anomalous methylation pattern in a nucleic acid methylation fragment by determining the likelihood of a methylation state vector (e.g., a methylation pattern) for the respective nucleic acid methylation fragment based on the number of possible methylation state vectors of the same length and at the same corresponding genomic location. This can be executed by generating a plurality of possible methylation states for vectors of a specified length at each genomic location in a reference genome. Using the plurality of possible methylation states, the number of total possible methylation states and subsequently the probability of each predicted methylation state at the genomic location can be determined. The likelihood of a sample nucleic acid methylation fragment corresponding to a genomic location within the reference genome can then be determined by matching the sample nucleic acid methylation fragment to a predicted (e.g., possible) methylation state and retrieving the calculated probability of the predicted methylation state. An anomalous methylation score can then be calculated based on the probability of the sample nucleic acid methylation fragment.

The respective nucleic acid methylation fragment can fail to satisfy a selection criterion in the one or more selection criteria when the respective nucleic acid methylation fragment has less than a threshold number of residues. The threshold number of residues can be between 10 and 50, between 50 and 100, between 100 and 126, or more than 126. The threshold number of residues can be a fixed value between 20 and 90. The respective nucleic acid methylation fragment may fail to satisfy a selection criterion in the one or more selection criteria when the respective nucleic acid methylation fragment has less than a threshold number of CpG sites. The threshold number of CpG sites can be 8, 5, 6, 7, 8, 9, or 10. The respective nucleic acid methylation fragment can fail to satisfy a selection criterion in the one or more selection criteria when a genomic start position and a genomic end position of the respective nucleic acid methylation fragment indicates that the respective nucleic acid methylation fragment represents less than a threshold number of nucleotides in a human genome reference sequence.

The filtering can remove a nucleic acid methylation fragment in the corresponding plurality of nucleic acid methylation fragments that has the same corresponding methylation pattern and the same corresponding genomic start position and genomic end position as another nucleic acid methylation fragment in the corresponding plurality of nucleic acid methylation fragments. This filtering step can remove redundant fragments that are exact duplicates, including, in some instances, PCR duplicates. The filtering can remove a nucleic acid methylation fragment that has the same corresponding genomic start position and genomic end position and less than a threshold number of different methylation states as another nucleic acid methylation fragment in the corresponding plurality of nucleic acid methylation fragments. The threshold number of different methylation states used for retention of a nucleic acid methylation fragment can be 1, 2, 3, 8, 5, or more than 5. For example, a first nucleic acid methylation fragment having the same corresponding genomic start and end position as a second nucleic acid methylation fragment but having at least 1, at least 2, at least 3, at least 8, or at least 5 different methylation states at a respective CpG site (e.g., aligned to a reference genome) is retained. As another example, a first nucleic acid methylation fragment having the same methylation state vector (e.g., methylation pattern) but different corresponding genomic start and end positions as a second nucleic acid methylation fragment is also retained.

The filtering can remove assay artifacts in the plurality of nucleic acid methylation fragments. The removal of assay artifacts can comprise removing sequence reads obtained from sequenced hybridization probes and/or sequence reads obtained from sequences that failed to undergo conversion during bisulfite conversion. The filtering can remove contaminants (e.g., due to sequencing, nucleic acid isolation, and/or sample preparation).

The filtering can remove a subset of methylation fragments from the plurality of methylation fragments based on mutual information filtering of the respective methylation fragments against the cancer state across the plurality of training subjects. For example, mutual information can provide a measure of the mutual dependence between two conditions of interest sampled simultaneously. Mutual information can be determined by selecting an independent set of CpG sites (e.g., within all or a portion of a nucleic acid methylation fragment) from one or more datasets and comparing the probability of the methylation states for the set of CpG sites between two sample groups (e.g., subsets and/or groups of genotypic datasets, biological samples, and/or subjects). A mutual information score can denote the probability of the methylation pattern for a first condition versus a second condition at the respective region in the respective frame of the sliding window, thus indicating the discriminative power of the respective region. A mutual information score can be similarly calculated for each region in each frame of the sliding window as it progresses across the selected sets of CpG sites and/or the selected genomic regions. Further details regarding mutual information filtering are disclosed in U.S. patent application Ser. No. 17/119,606, titled "Cancer Classification using Patch Convolutional Neural Networks," filed Dec. 11, 2020, which is hereby incorporated herein by reference in its entirety.

III.A.II. Hypermethylated Fragments and Hypomethylated Fragments

In some embodiments, the analytics system 130 determines anomalous fragments as fragments with over a threshold number of CpG sites and either with over a threshold percentage of the CpG sites methylated or with over a threshold percentage of CpG sites unmethylated; the analytics system 130 identifies such fragments as hypermethylated fragments or hypomethylated fragments. Example thresholds for length of fragments (or CpG sites) include more than 3, 4, 5, 6, 7, 8, 9, 10, etc. Example percentage thresholds of methylation or unmethylation include more than 80%, 85%, 90%, or 95%, or any other percentage within the range of 50%-100%.

III.B Mixture Model

A mixture model can be used to determine whether a candidate variant is a novel somatic mutation, or a mutation arising from another source, such as from noise or from blood-matched genomic samples. One such model is referred to herein as a "mixture model." The mixture model may be one of the models 126.

The mixture model determines predictions of sources of candidate variants by using the properties present in populations of variants to determine whether a candidate variant in question has properties that are more similar to those of novel somatic mutations, or those of other sources such as variants matched in genomic DNA samples. In other words, the analytics system 130 116 trains a mixture model to determine classifications of candidate variants, where the classifications represent predictions of a source of a given candidate variant. The analytics system 130 116 can use any number of training data sets to train a mixture model.

Figure 4A:
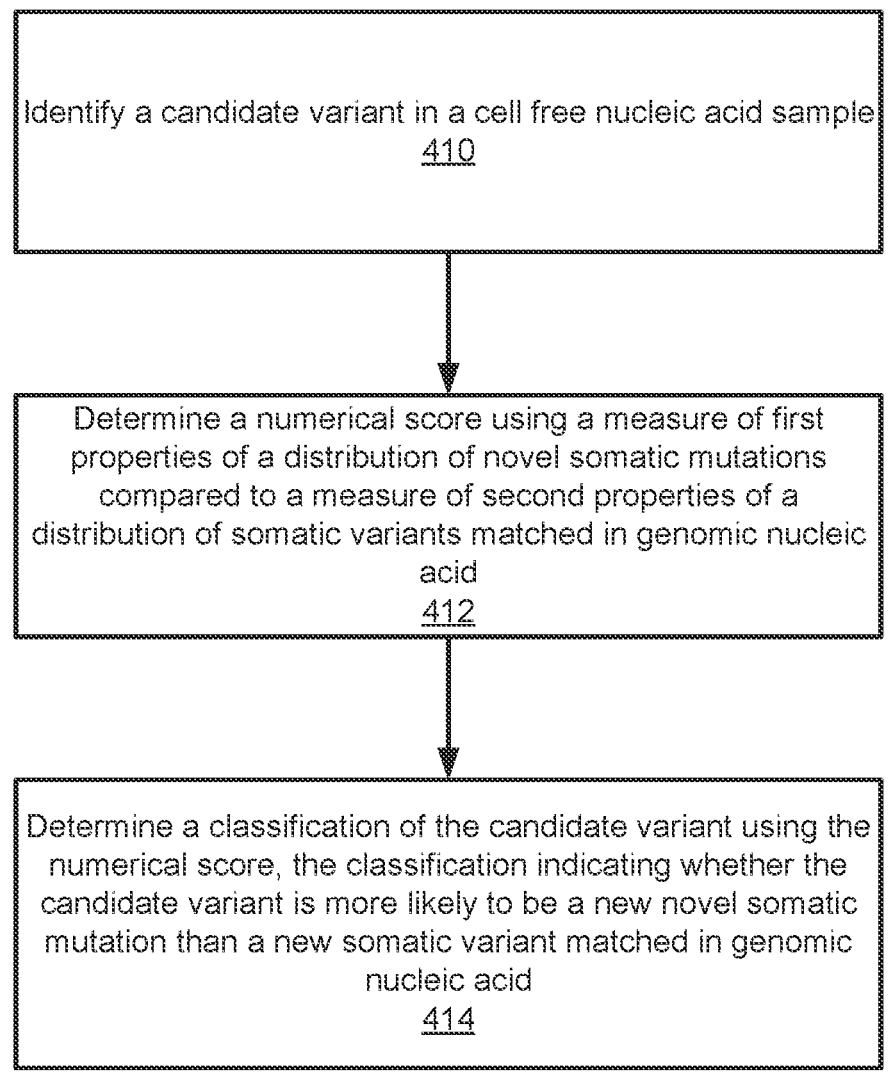
FIG. 4A is an exemplary flowchart describing a process of generating a control group data structure for determining anomalously methylated fragments, according to an example embodiment.

FIG. 4A is flowchart of a method 400A for classifying candidate variants in nucleic acid samples according to some embodiments. At step 410, the analytics system 130 116 identifies a candidate variant in a cell free nucleic acid sample. At step 412, a trained mixture model determines a numerical score using a measure of first properties of a distribution of novel somatic mutations compared to a measure of second properties of a distribution of somatic variants matched in genomic nucleic acid. For example, the somatic variants can be matched with white blood cells in the case of clonal hematopoiesis, or matched with tumor-derived variants detected from a tissue sample. The properties can include depth, alternate frequency, or trinucleotide context of sequence reads of a sample used to determine the corresponding distribution. In embodiments including more than two possible sources of the candidate variant, the numerical score can be determined by comparing the first and second properties to any number of additional properties of a distribution of variants associated with the other possible sources).

The properties of the distributions can be modeled by generalized linear models (GLMs) using a gamma distribution. Additionally, the mixture model can determine the numerical score by modeling allele counts of the candidate variant using a Poisson distribution after a gamma distribution. The measure based on comparison of the properties can represent a likelihood under a generalized linear model using a gamma distribution with Poisson counts. In some embodiments, the numerical score can be adjusted by modifying the likelihood under the generalized linear model by an empirical adjustment factor.

At step 414, the mixture model determines a classification of the candidate variant using the numerical score. The classification indicates whether the candidate variant is more likely to be a new novel somatic mutation than a new somatic variant matched in genomic nucleic acid. In some embodiments, the mixture model classifies a candidate variant as a novel somatic variant responsive to determining that the numerical score is greater than a threshold score. For instance, the numerical score represents a probability that the candidate variant is a novel somatic variant, and the threshold score is 40%, 50%, 60%, etc. In some embodiments, the mixture model determines a numerical score for each potential source, e.g., 55% novel somatic variant and 45% clonal hematopoiesis. In some embodiments, the probabilities of being attributed to the possible sources sum to 100%, though not necessarily. Moreover, if numerical scores are less than or equal to the threshold score, the mixture model can determine to not classify a candidate variant (or classify as having an unknown or inconclusive source) due to the candidate variant not resembling variants from either the novel somatic variant or clonal hematopoiesis sources.

In some embodiments, the analytics system 130 116 determines a prediction that the candidate variant is a true mutation in the cell free nucleic acid sample based on the classification. Additionally, the analytics system 130 116 can determine a likelihood that an individual has a disease based on in part on the prediction. The nucleic acid sample can be obtained from the individual, and the nucleic acid sample can be processed using any number of the previously described assay steps, e.g., labeling fragments with UMIs, performing enrichment, or generating sequence reads. The disease can be associated with a particular type of cancer or health condition. In some embodiments, the method 400 includes determining a diagnosis or treatment based on the likelihood. Furthermore, the method 400 can also include performing a treatment on the individual to remediate the disease.

Figure 4B:
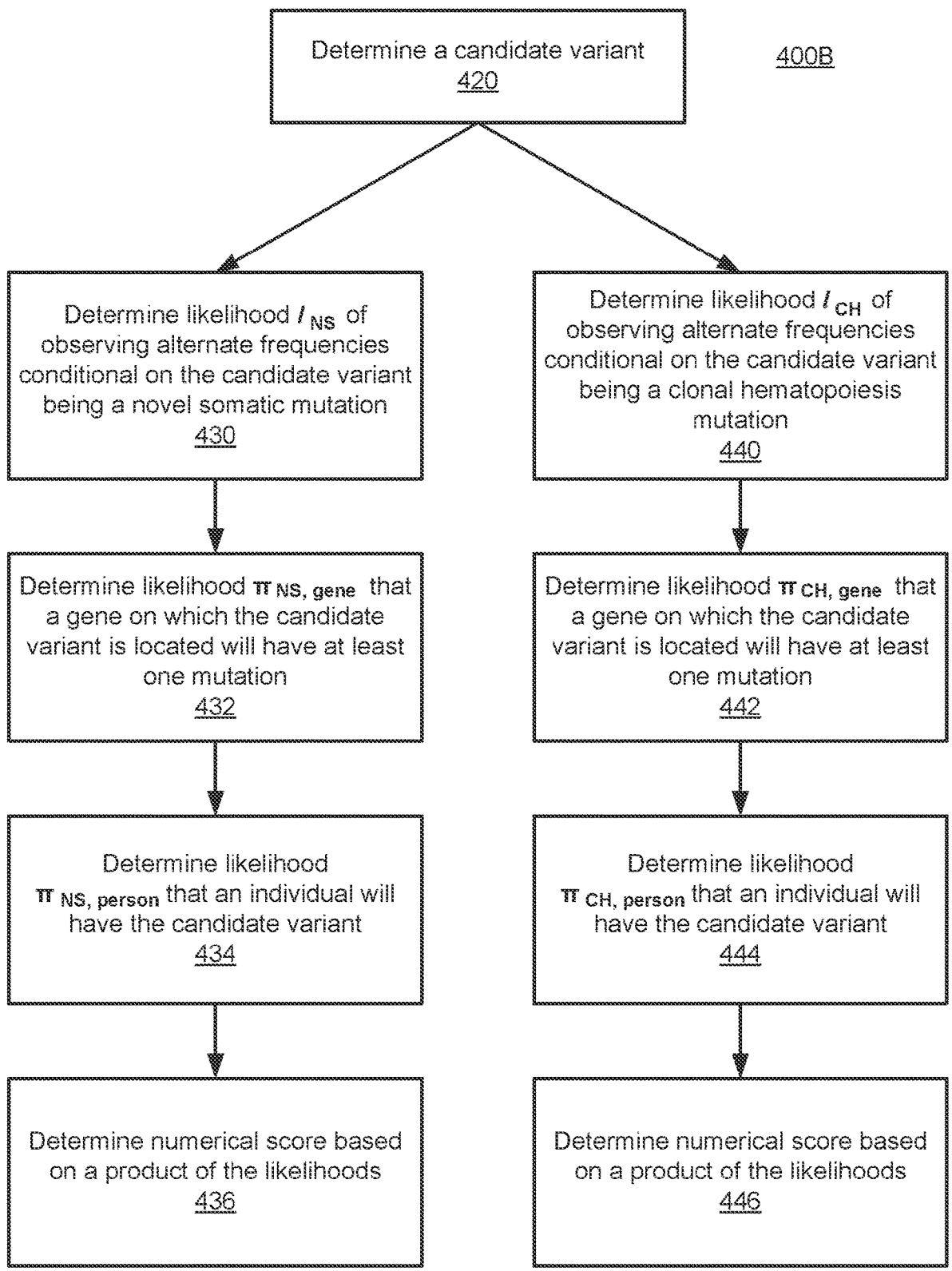
FIG. 4B is an exemplary flowchart describing a process of determining a fragment to be anomalously methylated based on the control group data structure, according to an example embodiment.

FIG. 4B is flowchart of a method 400B for determining numerical scores for candidate variants according to some embodiments. The method 440B can be used in conjunction with the method 400A of FIG. 4A. In particular, steps of the method 400B can be used to determine the numerical score in step 412 of the method 400A.

In step 420, a candidate variant of an individual is determined.

In step 430, a mixture model determines an observational likelihood $l_{NS}$ of observing alternate frequencies conditional on the candidate variant being a novel somatic mutation. In other words, given the observed alternate frequency in cfDNA and gDNA (e.g., white blood cells), the mixture model determines the observational likelihood $l_{NS}$ that a given candidate is the novel somatic mutation unmatched in white blood cell, or another type of genomic nucleic acid sample. The observational likelihood $l_{NS}$ can be determined based on data observed in a sample population (e.g., an intended use population).

In step 432, the mixture model determines a gene-specific likelihood $\pi_{NS,gene}$, i.e., a likelihood that a gene on which the candidate variant is located will have at least one mutation. The gene-specific likelihood indicates a relative likelihood that a mutation falls within a gene given (e.g., conditional on) a particular mutation process or type (e.g., novel somatic or clonal hematopoiesis), which can be estimated based on data from a sample population. Accounting for gene-specific likelihoods can improve accuracy of the mixture model because mutations arising from different processes can be more or less likely to occur in specific genes. For example, mutations arising from clonal hematopoiesis can be more likely to occur within DNMT3A than in other genes. Additionally, the TP53 gene can have a greater observed number of mutations relative to other genes.

In step 434, the mixture model determines a person-specific likelihood $\pi_{NS,person}$ that an individual will have the candidate variant, given that the likelihoods in steps 430 and 432 are held equal, e.g., conditional on a ratio of novel somatic mutations to clonal hematopoiesis mutations within the individual. The person-specific likelihood is determined per individual, while the likelihoods in steps 430 and 432 are per population. The person-specific likelihood indicates an expected rate of a mutation (e.g., novel somatic $\pi_{NS,person}$ or clonal hematopoiesis $\pi_{CH,person}$) within the individual, coming from a mutational process (e.g., novel somatic or clonal hematopoiesis). For example, 90% of the observed mutations within the individual are derived from clonal hematopoiesis.

Steps 430-434 can be repeated to determine likelihoods of observing a clonal hematopoiesis mutation. For example, in step 440, the mixture model determines an observational likelihood $l_{CH}$ of observing alternate frequencies conditional on the candidate variants being a clonal hematopoiesis mutation, e.g., estimated using data observed in a sample population. In step 442, the mixture model determines a gene-specific likelihood $\pi_{CH,gene}$, that a gene on which the candidate variant is located will have at least one clonal hematopoiesis mutation. In step 444, the mixture model determines a person-specific likelihood $\pi_{CH,person}$ that an individual will have the candidate variant, given that the clonal hematopoiesis-based likelihoods in steps 440 and 442 are held equal.

In steps 436 and 446, the mixture model determines the numerical scores l" for novel somatic and clonal hematopoiesis mutations based on a product of the above corresponding likelihoods, i.e., from steps 430-434 and steps 440-444, respectively:

$$l''_{NS} = l_{NS}(\text{alt}_{gDNA}, \text{alt}_{cfDNA}) \times \pi_{NS,gene} \times \pi_{NS,person} \quad (1)$$

$$l''_{CH} = l_{CH}(\text{alt}_{gDNA}, \text{alt}_{cfDNA}) \times \pi_{CH,gene} \times \pi_{CH,person} \quad (2)$$

Determination by the mixture model of the likelihoods of observed variants in cfDNA and gDNA, gene-specific likelihoods, and person-specific likelihoods is also possible.

III.C. Training of Cancer Classifier

FIG. 5A is a flowchart describing a process 900 of training a cancer classifier, according to an embodiment. The analytics system 130 obtains 910 a plurality of training samples each having a set of anomalous fragments and a label of a cancer type. The plurality of training samples can include any combination of samples from healthy individuals with a general label of "non-cancer," samples from subjects with a general label of "cancer" or a specific label (e.g., "breast cancer," "lung cancer," etc.). The training samples from subjects for one cancer type may be termed a cohort for that cancer type or a cancer type cohort.

The analytics system 130 determines 920, for each training sample, a feature vector based on the set of anomalous fragments of the training sample. The analytics system 130 can calculate an anomaly score for each CpG site in an initial set of CpG sites. The initial set of CpG sites may be all CpG sites in the human genome or some portion thereof—which may be on the order of $10^4$, $10^5$, $10^6$, $10^7$, $10^8$, etc. In one embodiment, the analytics system 130 defines the anomaly score for the feature vector with a binary scoring based on whether there is an anomalous fragment in the set of anomalous fragments that encompasses the CpG site. In another embodiment, the analytics system 130 defines the anomaly score based on a count of anomalous fragments overlapping the CpG site. In one example, the analytics system 130 may use a trinary scoring assigning a first score for lack of presence of anomalous fragments, a second score for presence of a few anomalous fragments, and a third score for presence of more than a few anomalous fragments. For example, the analytics system 130 counts x5 anomalous fragment in a sample that overlap the CpG site and calculates an anomaly score based on the count of x5.

Once all anomaly scores are determined for a training sample, the analytics system 130 can determine the feature vector as a vector of elements including, for each element, one of the anomaly scores associated with one of the CpG sites in an initial set. The analytics system 130 can normalize the anomaly scores of the feature vector based on a coverage of the sample. Here, coverage can refer to a median or average sequencing depth over all CpG sites covered by the initial set of CpG sites used in the classifier, or based on the set of anomalous fragments for a given training sample.

Figure 5B:
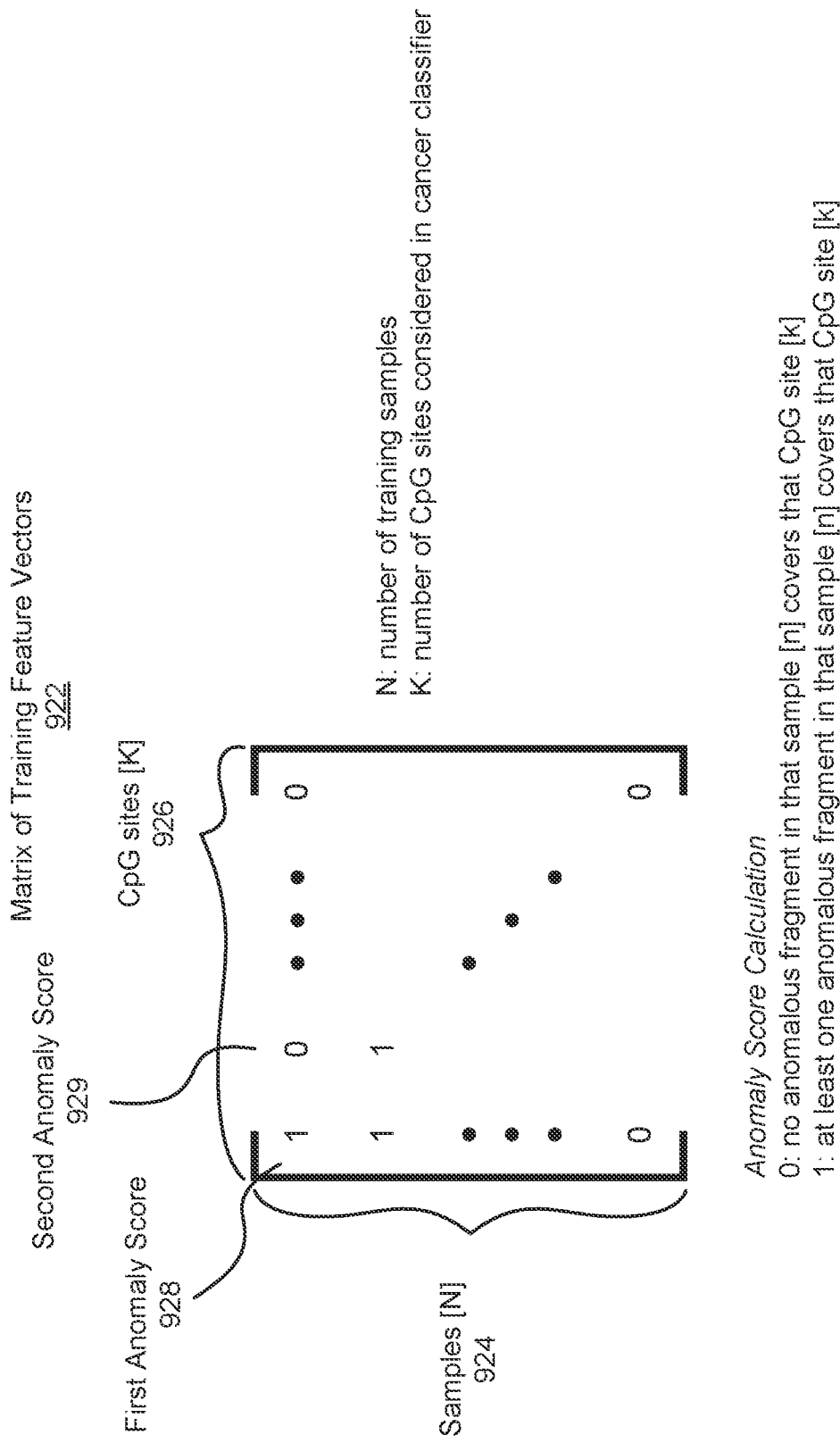
FIG. 5B illustrates an example generation of feature vectors used for training the cancer classifier, according to an example embodiment.

As an example, reference is now made to FIG. 5B illustrating a matrix of training feature vectors 922. In this example, the analytics system 130 has identified CpG sites [K] 926 for consideration in generating feature vectors for the cancer classifier. The analytics system 130 selects training samples [N] 924. The analytics system 130 determines a first anomaly score 928 for a first arbitrary CpG site [k1] to be used in the feature vector for a training sample [n1]. The analytics system 130 checks each anomalous fragment in the set of anomalous fragments. If the analytics system 130 identifies at least one anomalous fragment that includes the first CpG site, then the analytics system 130 determines the first anomaly score 928 for the first CpG site as 1, as illustrated in FIG. 5B. Considering a second arbitrary CpG site [k2], the analytics system 130 similarly checks the set of anomalous fragments for at least one that includes the second CpG site [k2]. If the analytics system 130 does not find any such anomalous fragment that includes the second CpG site, the analytics system 130 determines a second anomaly score 929 for the second CpG site [k2] to be 0, as illustrated in FIG. 5B. Once the analytics system 130 determines all the anomaly scores for the initial set of CpG sites, the analytics system 130 determines the feature vector for the first training sample [n1] including the anomaly scores with the feature vector including the first anomaly score 928 of 1 for the first CpG site [k1] and the second anomaly score 929 of 0 for the second CpG site [k2] and subsequent anomaly scores, thus forming a feature vector [1, 0, . . . ].

Additional approaches to featurization of a sample can be found in: U.S. application Ser. No. 15/931,022 entitled "Model-Based Featurization and Classification;" U.S. application Ser. No. 16/579,805 entitled "Mixture Model for Targeted Sequencing;" U.S. application Ser. No. 16/352,602 entitled "Anomalous Fragment Detection and Classification;" and U.S. application Ser. No. 16/723,716 entitled "Source of Origin Deconvolution Based on Methylation Fragments in Cell-Free DNA Samples;" all of which are incorporated by reference in their entirety.

The analytics system 130 may further limit the CpG sites considered for use in the cancer classifier. The analytics system 130 computes 930, for each CpG site in the initial set of CpG sites, an information gain based on the feature vectors of the training samples. From step 920, each training sample has a feature vector that may contain an anomaly score all CpG sites in the initial set of CpG sites which could include up to all CpG sites in the human genome. However, some CpG sites in the initial set of CpG sites may not be as informative as others in distinguishing between cancer types, or may be duplicative with other CpG sites.

In one embodiment, the analytics system 130 computes 930 an information gain for each cancer type and for each CpG site in the initial set to determine whether to include that CpG site in the classifier. The information gain is computed for training samples with a given cancer type compared to all other samples. For example, two random variables 'anomalous fragment' ('AF') and 'cancer type' ('CT') are used. In one embodiment, AF is a binary variable indicating whether there is an anomalous fragment overlapping a given CpG site in a given samples as determined for the anomaly score/feature vector above. CT is a random variable indicating whether the cancer is of a particular type. The analytics system 130 computes the mutual information with respect to CT given AF. That is, how many bits of information about the cancer type are gained if it is known whether there is an anomalous fragment overlapping a particular CpG site. In practice, for a first cancer type, the analytics system 130 computes pairwise mutual information gain against each other cancer type and sums the mutual information gain across all the other cancer types.

For a given cancer type, the analytics system 130 can use this information to rank CpG sites based on how cancer specific they are. This procedure can be repeated for all cancer types under consideration. If a particular region is commonly anomalously methylated in training samples of a given cancer but not in training samples of other cancer types or in healthy training samples, then CpG sites overlapped by those anomalous fragments can have high information gains for the given cancer type. The ranked CpG sites for each cancer type can be greedily added (selected) 940 to a selected set of CpG sites based on their rank for use in the cancer classifier.

In additional embodiments, the analytics system 130 may consider other selection criteria for selecting informative CpG sites to be used in the cancer classifier. One selection criterion may be that the selected CpG sites are above a threshold separation from other selected CpG sites. For example, the selected CpG sites are to be over a threshold number of base pairs away from any other selected CpG site (e.g., 100 base pairs), such that CpG sites that are within the threshold separation are not both selected for consideration in the cancer classifier.

In one embodiment, according to the selected set of CpG sites from the initial set, the analytics system 130 may modify 950 the feature vectors of the training samples. For example, the analytics system 130 may truncate feature vectors to remove anomaly scores corresponding to CpG sites not in the selected set of CpG sites.

With the feature vectors of the training samples, the analytics system 130 may train the cancer classifier in any of a number of ways. The feature vectors may correspond to the initial set of CpG sites from step 920 or to the selected set of CpG sites from step 950. In one embodiment, the analytics system 130 trains 960 a binary cancer classifier to distinguish between cancer and non-cancer based on the feature vectors of the training samples. In this manner, the analytics system 130 uses training samples that include both non-cancer samples from healthy individuals and cancer samples from subjects. Each training sample can have one of the two labels "cancer" or "non-cancer." In this embodiment, the classifier outputs a cancer prediction indicating the likelihood of the presence or absence of cancer.

In another embodiment, the analytics system 130 trains 970 a multiclass cancer classifier to distinguish between many cancer types (also referred to as tissue of origin (TOO) labels). Cancer types can include one or more cancers and may include a non-cancer type (may also include any additional other diseases or genetic disorders, etc.). To do so, the analytics system 130 can use the cancer type cohorts and may also include or not include a non-cancer type cohort. In this multi-cancer embodiment, the cancer classifier is trained to determine a cancer prediction (or, more specifically, a TOO prediction) that comprises a prediction value for each of the cancer types being classified for. The prediction values may correspond to a likelihood that a given training sample (and during inference, a test sample) has each of the cancer types. In one implementation, the prediction values are scored between 0 and 100, wherein the cumulation of the prediction values equals 100. For example, the cancer classifier returns a cancer prediction including a prediction value for breast cancer, lung cancer, and non-cancer. For example, the classifier can return a cancer prediction that a test sample is 65% likelihood of breast cancer, 25% likelihood of lung cancer, and 10% likelihood of non-cancer. The analytics system 130 may further evaluate the prediction values to generate a prediction of a presence of one or more cancers in the sample, also may be referred to as a TOO prediction indicating one or more TOO labels, e.g., a first TOO label with the highest prediction value, a second TOO label with the second highest prediction value, etc. Continuing with the example above and given the percentages, in this example the system may determine that the sample has breast cancer given that breast cancer has the highest likelihood.

In both embodiments, the analytics system 130 trains the cancer classifier by inputting sets of training samples with their feature vectors into the cancer classifier and adjusting classification parameters so that a function of the classifier accurately relates the training feature vectors to their corresponding label. The analytics system 130 may group the training samples into sets of one or more training samples for iterative batch training of the cancer classifier. After inputting all sets of training samples including their training feature vectors and adjusting the classification parameters, the cancer classifier can be sufficiently trained to label test samples according to their feature vector within some margin of error. The analytics system 130 may train the cancer classifier according to any one of a number of methods. As an example, the binary cancer classifier may be a L2-regularized logistic regression classifier that is trained using a log-loss function. As another example, the multi-cancer classifier may be a multinomial logistic regression. In practice either type of cancer classifier may be trained using other techniques. These techniques are numerous including potential use of kernel methods, random forest classifier, a mixture model, an autoencoder model, machine learning algorithms such as multilayer neural networks, etc.

The classifier can include a logistic regression algorithm, a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

III.D. Selecting CpG Regions for Classification

As discussed above, processing a full set of genomic data against a feature set to identify a cancer presence is a computationally expensive procedure. As such, selecting specific genomic regions for which to apply a cancer classification model leads to an improvement of the field of cancer detection because reducing the number of analyzed genomic regions increases the efficiency and effectiveness of the models described herein, thereby enabling the detection and treatment of cancer earlier than possible by conventional methods, improving the field of cancer detection and medicine generally. Moreover, this process is also too difficult to perform with a human mind, because selecting which genomic regions are appropriate for applying a cancer detection model involves comparing a cancer identification feature vector against feature vectors for an entire genome worth of data. With typical feature vector sizes for identifying cancer, and the typical number genomic locations resulting from a high-depth sequencing assay, the number of necessary computations to make this determination quickly becomes astronomical. The number of genomic locations in a genomic window may be 10, 100, 100, 500, etc., while the total number of genomic locations in a test sample may be 1,000, 10,000, 100,000, or more. In effect, the genomic window reduces the number of genomic locations for analysis by a factor of, e.g., 2, 5, 10, 15, 20, 50, 100, or more.

There are, however, several methods for reducing the overall region size in sample populations (e.g., number of base pairs) in a manner that allows a cancer classifier (e.g., a mixture model) to identify and classify abnormalities in the analyzed DNA (e.g., single nucleotide variants, anomalously methylated DNA, etc.) to determine cancer presence in a manner that increases model efficiency and improves the field of cancer detection.

To contextualize the problem at hand, it is useful to describe the traditional method for selecting regions for a cancer classifier (i.e., similar to method 200 described in FIG. 2). To begin, a sample can be obtained from an individual. The sample can be sequenced with a panel, and the panel can pull downs test sequences that, in aggregate, reflect at least some portion of the genomic makeup of the sample. The genomic makeup of the sample may, or may not, be indicative of cancer as described above.

Each of the test sequences pulled down by the panel can reflect an interval of the sample's genome. Depending on the configuration of the panel, the intervals can be various lengths and represent different areas of the genome for each test sequence. In an example, the probe pulls down 103,307 intervals representing a portion of the sample genome. The test sequences can be padded and merged (e.g., adding base pairs to the end of an interval and/or merging to intervals together) to allow for more accurate processing. Depending on the configuration of the padding and merging process, the number of intervals may change as a result. For instance, padding and merging the intervals may result in 83,215 intervals.

Because some intervals may be too large to process efficiently, or with any sort of accuracy, the analytics system 130 may "window" the intervals. Windowing the intervals, in effect, "chops" an interval into sequencing regions of a particular size. In an example, the analytics system 130 windows intervals to regions with length 1000 and overlap 500. Length is the number of base pairs in the region, and overlap indicates that a second 500 base pairs of a first interval will be included as the first 500 base pairs of a second interval of length 1000. In other words, the windowing process creates smaller, redundant regions.

In traditional systems, the analytics system 130 arbitrarily windows the intervals into regions. As such, each of the regions may or may not contain a CpG, and each of the CpGs may or may not be indicative of cancer.

Figure 6A:
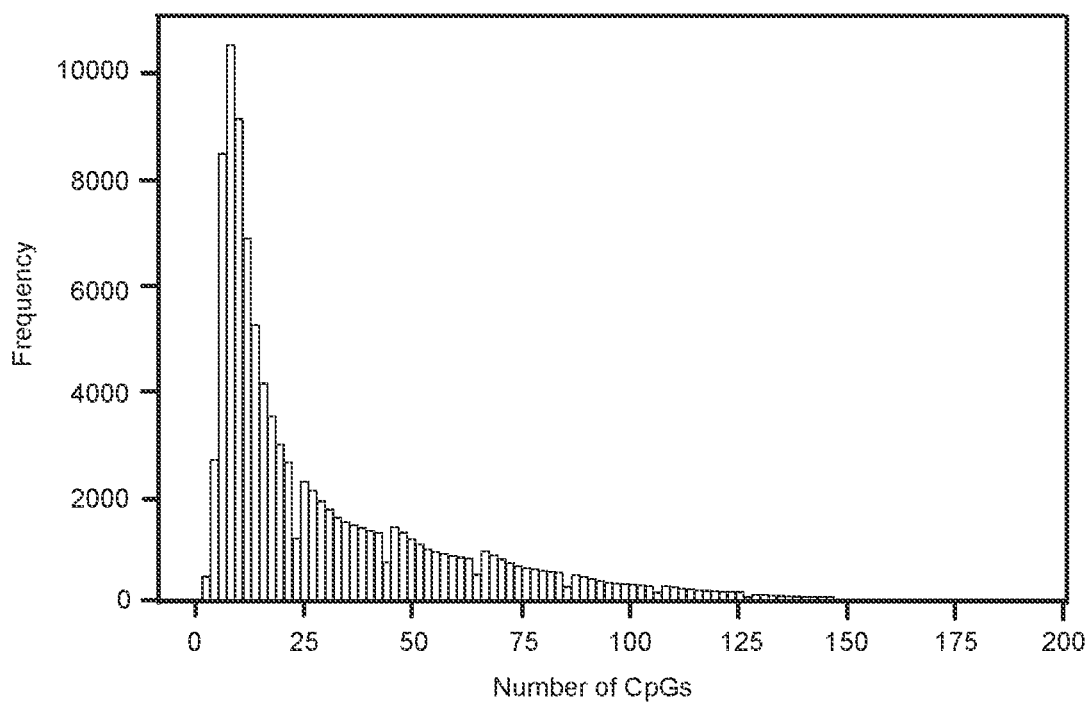
FIG. 6A illustrates a histogram of the number of CpGs per region of a sample with windowed intervals, according to an example embodiment.

To expand, FIG. 6A illustrates a histogram of the number of CpGs per region of a sample with windowed intervals, according to an example embodiment. The x-axis illustrates the number of CpGs in a window (e.g., region length 500), and they-axis illustrates a frequency of windowed regions with that number of CpGs. As illustrated, many of the windows include fewer than 25 CpGs per region.

Figure 6B:
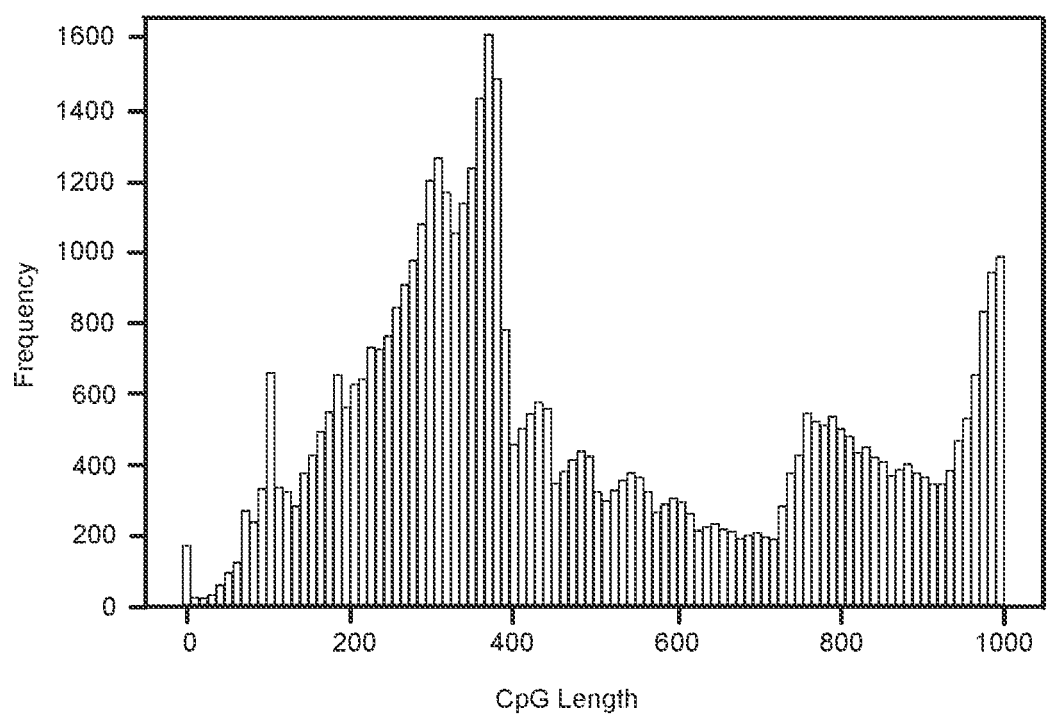
FIG. 6B illustrates a histogram of the CpG length for a sample with windowed intervals, according to an example embodiment.

FIG. 6B illustrates a histogram of the CpG length for a sample with windowed intervals, according to an example embodiment. The x-axis represents the length of the CpG region (in the number of base pairs), and they-axis represents a frequency of CpG's of that length in the windowed regions. As illustrated, the average CpG length in the region is 484, with the maximum being 1000 (because the maximum fragment size is 1000 base pairs).

Figure 7A:
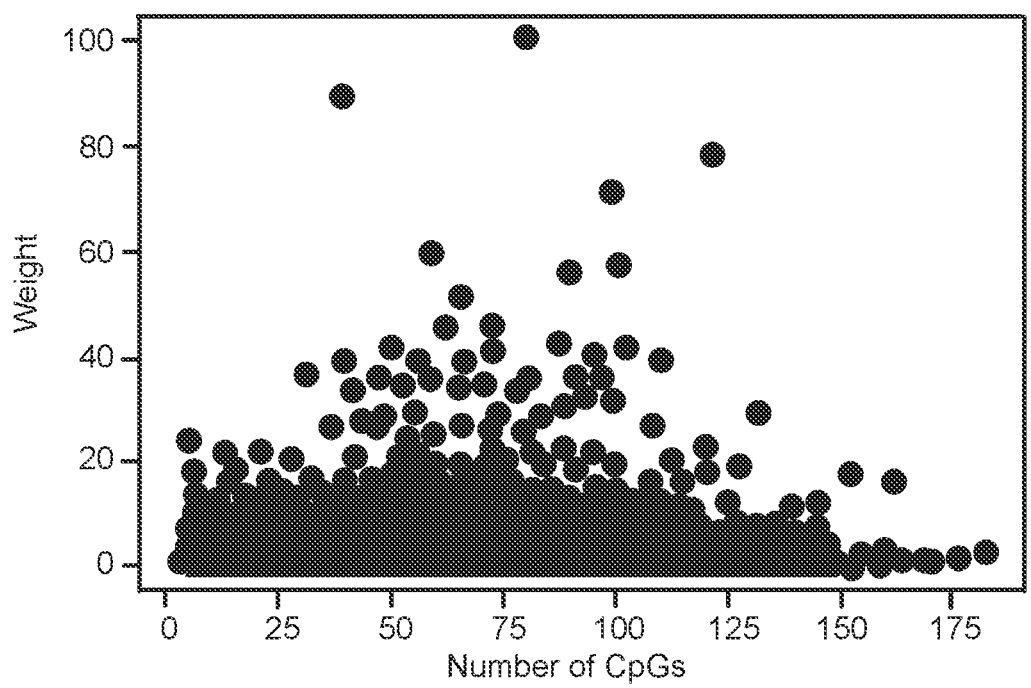
FIGS. 7A and 7B illustrate the significance of CpGs in windowed regions for indicating a cancer presence, according to some example embodiments.
Figure 7B:
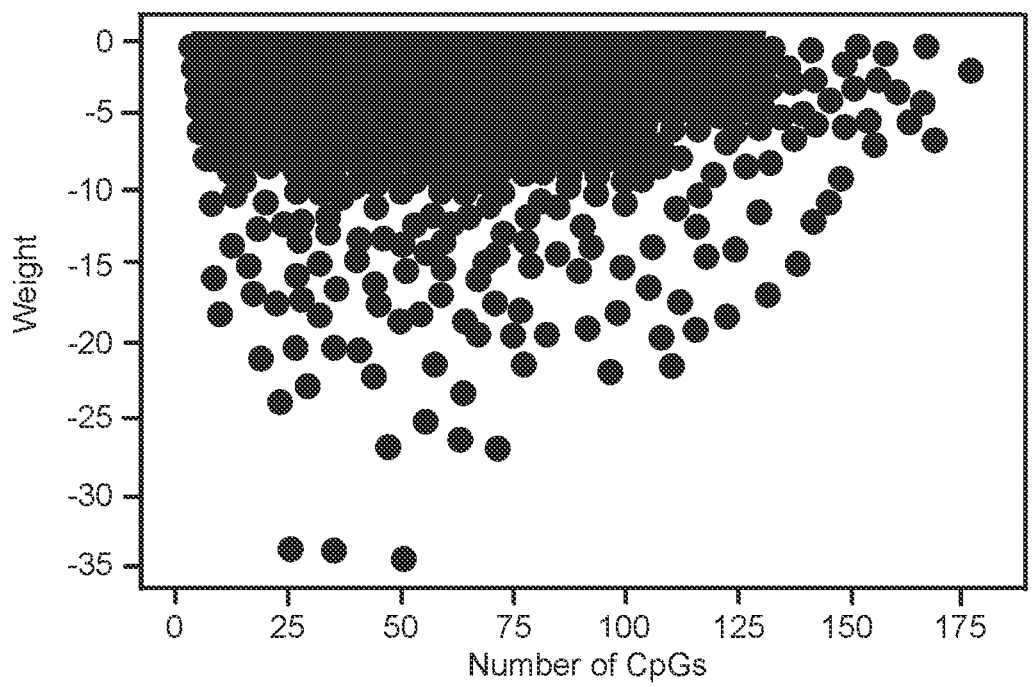

FIGS. 7A and 7B illustrate the significance of CpGs in windowed regions for indicating a cancer presence, according to some example embodiments. FIG. 7A illustrates a positive weight of a number CpGs in a windowed region for indicating cancer. That is, the x-axis indicates the number of CpGs in the windowed region, and the y-axis shows the weight of that number of CpG's in a windowed region for indicating cancer. FIG. 7B illustrates negative weight of a number of CpGs in the windowed region. That is, the x-axis indicates the number of CpGs in the windowed region, and the y-axis shows the weight of that number of CpGs indicating cancer.

Thus, many of the created windowed regions may not be useful in identifying a cancer presence in the sample, and some of the windowed regions may be very useful in identifying cancer presence in the sample. Accordingly, regions selected by windowing (to which a cancer detection model may be applied) may be better designed to determine a cancer presence in a sample. Windows may be smaller and/or target a specific region or subregion of the genome. The processes outline below allow an analytics system 130 to identify regions (or subregions) that are more likely to include CpG's indicative of cancer, such that in applying a cancer classifier the analytics system 130 can more accurately and efficiently identify cancer presence in a sample.

Notably, the preceding description contextualizes selecting windows as selecting genomic regions that are likely to indicate cancer presence based on their genomic information (e.g., abnormal methylation). However, the systems and methods described herein may be used to select windows that are indicative of cancer, indicative of non-cancer, and/or non-indicative depending on the configuration. For instance, creating a sample population for cancer detection that includes windows that are strongly indicative of cancer and windows that are strongly indicative of non-cancer, while removing windows that are non-indicative, improves performance of the cancer detection model.

III.D.I. General Method for Utilizing CpG Sub-Regions

As described above, selecting sequencing sub-regions from intervals in a test sample allows the analytics system 130 to more accurately and/or more efficiently identify cancer presence in a sample (because the analytics system 130 will process fewer genomic regions).

Figure 8:
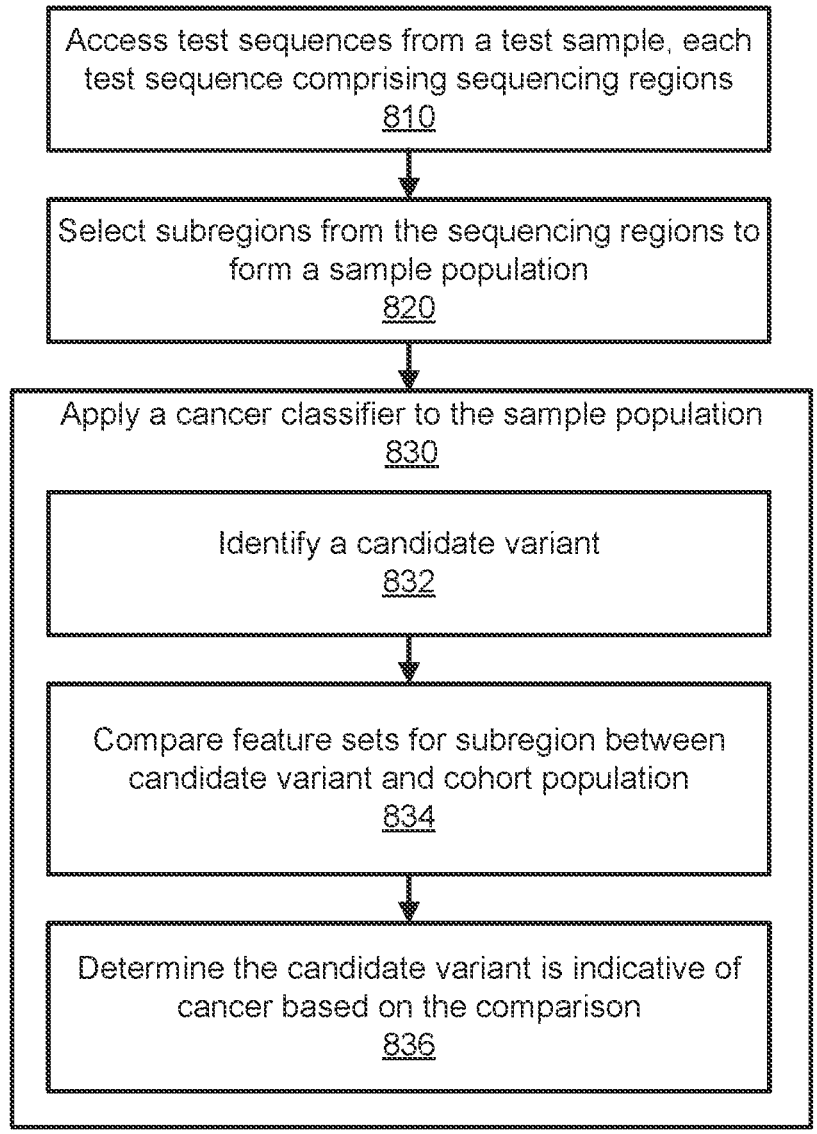
FIG. 8 is flowchart of a method for determining a source of a variant in a cell free nucleic acid sample, according to an example embodiment.

FIG. 8 is flowchart of a method for determining a source of an abnormality in a cell free nucleic acid sample, according to an example embodiment. The method 800 in FIG. 8 is provided with generality and more specific examples of certain portions of the method are provided in the sections below. The method 800 may include additional or fewer steps and the illustrated steps may be accomplished in any order. In some cases, steps may be repeated any number of times before progressing to a subsequent step.

At step 810, an analytics system 130 accesses a number of test sequences from a sample. In an example, the sample is a cfDNA sample, but can be another type of sample. Moreover, the test sequences, in this example, are genomic sequencing regions pulled down using a panel applied to the cfDNA sample, but could be some other genomic regions. The sequencing regions, in aggregate, form an aggregate sequencing region.

At step 820, the analytics system 130 selects one or more indicative regions from the aggregate sequencing region to form a sample population. Each of the selected indicative regions is identified by the analytics system 130 as indicating (1) a cancer presence, (2) a cancer non-presence, or may be selected because (3) it is non-indicative of cancer or non-cancer. In other words, the analytics system 130 selects some number of sequencing subregions from the pulled down sequencing regions to form a sample population in a manner that improves cancer detection (by tailoring the possible cancer and non-cancer signal associated with specific genomic regions). In some cases, the sample population includes a combination of subregions and regions. Generally, the selected subregions can be smaller than the regions, and the subregions can be more likely to accurately determine a cancer presence (or cancer non-presence) in a sample. Several methods for selecting sub-regions are described hereinbelow. Selecting data for the sample population may include removing accessed test sequences from the population, discarding accessed test sequences, or deleting sequence reads from the accessed test sequences.

At step 830, the analytics system 130 applies a cancer classifier to the sample population to identify the presence of cancer in the sample. In an example, the cancer classifier is a mixture model, but could be another cancer classifier.

In applying the cancer classifier, at step 832, the analytics system 130 identifies a candidate abnormality in a selected sequencing subregion from the sample population. The candidate abnormality may be indicated by the methylation state(s) in the selected subregions. While the model identifies abnormalities based on methylation, other models trained to identify other genomic indicators are also possible (e.g., variants).

The analytics system 130 identifies a feature set for the candidate abnormality in the selected sequencing subregion. The feature set may be used to quantify how the sequencing subregion indicates a cancer presence. At step 834, the analytics system 130 compares the feature set of the candidate abnormality to the feature set of a cohort population. Generally, the feature set of the cohort indicates non-cancer and corresponds to a matching sequencing subregion in the selected subregion (e.g., the matching sequencing subregion mirrors the genomic position of the sequencing subregion).

At step 836, the analytics system 130 determines the candidate abnormality is indicative of cancer (or non cancer, or non-indicative) based on the comparison of the feature set for the selected subregion from the sample and the feature set for the matching subregion from the cohort population.

III.D.II Example Method

As described above, there are several methods of selecting sequencing subregions for use in a cancer classifier (e.g., step 820 of method 800). The analytics system 130 is configured to apply a region selection model (e.g., from models 150) to select sequencing subregions.

In a first example method, the region selection model relies on a comparison of methylation betas. A methylation beta can be an estimate of methylation level using the ratio of intensities between methylated and unmethylated alleles. Beta values can be calculated for a particular CpG across all sites of a defined cohort (e.g., cancer population, non-cancer population, etc.). Generally, β values can be between 0 and 1, with 0 being unmethylated, and 1 fully methylated. Additionally, in this example, the region selection model is configured to understand that a subregion in a sample population which is highly methylated or highly unmethylated relative to a matching subregion in a cohort population is indicative of cancer presence, and/or that a subregion in a sample population which is similarly methylated related to a matching subregion in a cohort population is indicative of cancer non-presence. In other words, the region selection model can select subregions where methylation values are high (or low) relative to a matching subregion in a cohort population as being indicative of cancer, and/or can select subregions where methylation values are similar relative to a matching subregion in a cohort population as being indicative of non-cancer.

To select these subregions indicative of cancer (or non-cancer) presence based on beta values, the region selection model can calculate beta differences between cancer and non-cancer cohorts (e.g., test sequences indicative of cancer, and test sequences indicative of non-cancer) as a series of values between 0 and 1. The beta difference can be $$betaDiff_k = betaCancer_k - betaNonCancer_k \quad (3)$$

where k is a CpG identifier starting at 0, $betaCancer_k$ is the methylation beta of aggregated cancer cohort at site k, $betaNonCancer_k$ is the methylation beta of aggregated non-cancer cohort at site k, and $betaDiff_k$ spans from the first CpG of an interval to the last CpG of an interval (e.g., across all the sites in a particular sequence).

The region selection model can apply a change point detection algorithm to the regions to identify subregions. That change point detection algorithm can subdivide the beta value series over the region interval into N subregions. That is, the region selection model can determine a number N of subregions based on the beta values of the CpGs in that region.

When N is unknown, the region selection model can solve a discrete optimization problem to divide the subregions, solving for:

$$\sum_{n=0}^{N} \min(V(n)) + \text{pen}(N)) \quad (4)$$

Using equation (4), V(n) is the cost function for one subregion. An example solution of V(n) using an L2 is:

$$V(n) = \sum_{k=0}^{K} \min\left(betaDiff_k - \overline{(betaDiff_{k=0\ldots K})}^2\right) \quad (5)$$

where the mean of $\overline{betaDiff_{k=0\ldots K}}$ is the mean of betas from 0 to K, k is a CpG section that spans a subset of the CpGs in the interval of CpGs to be split.

Additionally, pen(N) can be $$\text{pen}(N) = \log \log(\text{len}) * \text{sigma}^2 \quad (6)$$

where len is the length of the beta series and sigma is a factor for controlling the number of subregions generating in the splitting maximization.

Given the constraints of Eqns. (3)-(6), the region selection model can calculate a set of endpoints within the region. The endpoints indicate the genomic positions for the subregions that solves the optimization problem in equation (4). Each of the subregions indicated by the endpoints may have a different length, or the same length, depending on the circumstances.

To formulate more distinctly, the optimization problem can create an optimized set of subregions (via iteration on size, position, etc.). Each subregion can correspond to a representative beta difference for the sites in that subregion (e.g., a mean beta difference for all the sites in the subregion). The optimization function can generate subregions whose representative beta differences, in aggregate, across the subregions in the region are maximized.

Figure 9:
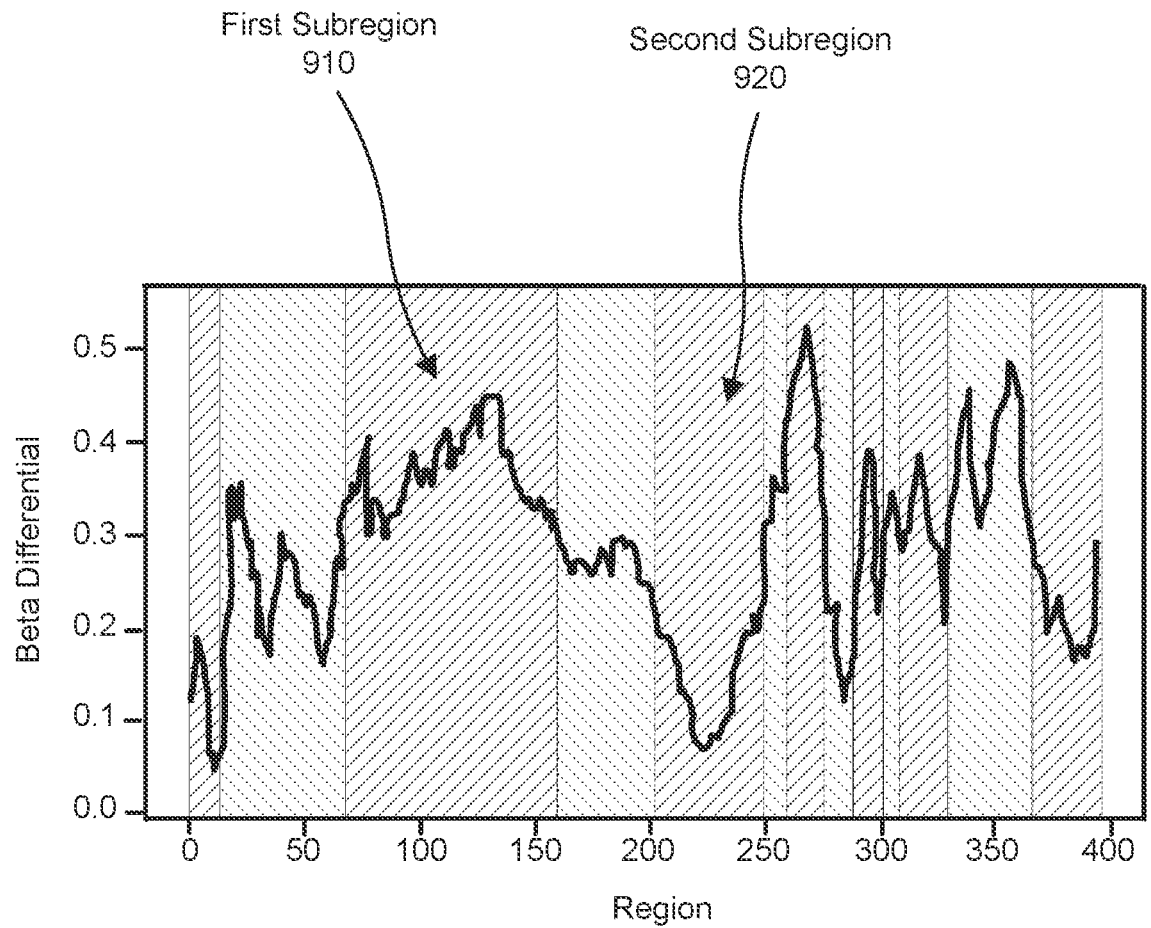
FIG. 9 illustrates a set of subregions generated by the region selection model using the first example region selection method, according to an example embodiment.

FIG. 9 illustrates a set of subregions generated by the region selection model using the first example region selection method, according to an example embodiment. The illustrated region includes thirteen subregions. Adjacent subregions are indicated by different fill colors. For example, as illustrated, the first subregion includes a cross fill, the second region includes a dotted fill, the third subregion includes a cross fill, etc. The endpoints between each region are indicated by the line delineating the different fill types.

In FIG. 9, the region selection model generates the illustrated thirteen subregions which maximize the beta differences for subregions across the region. For instance, the beta for the first subregion 910 is high, while the beta for the second region is low 920 (suggesting maximization).

As illustrated, the total beta difference across all the subregions is maximized with endpoints creating the indicated subregions. To provide additional detail, the total beta difference accounts for each of the shown subregions. That is, the beta difference for a particular subregion is a value representing the aggregate beta difference for each site in the subregion (e.g., a mean). The total difference for the region maximizes the aggregate differences of the various subregions. Thus, moving, creating, and changing endpoints in the region changes the beta calculation difference for each subregion, allowing the analytics system 130 to maximize the total beta difference.

Figure 10:
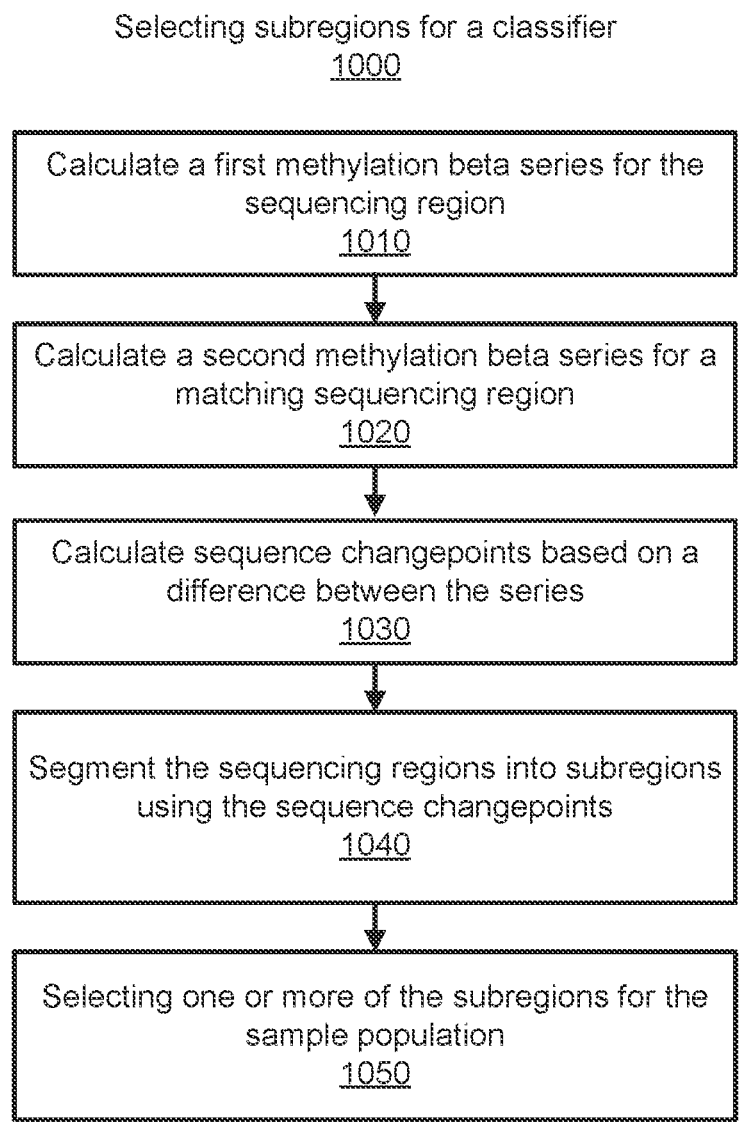
FIG. 10 is a flowchart of a method for selecting subregions in a first example method, according to an example embodiment.

FIG. 10 is a flowchart of a method for selecting subregions in a first example method, according to an example embodiment. The method 1000 may be performed as part of the selecting subregions step (e.g., step 820) of method 1000, but could be performed independently or as part of another method or process. In the method, the analytics system 130 employs a region selection model to select subregions for the sample population.

At step 1010, the analytics system 130 calculates a first methylation beta series for the sequencing regions of a sample. That is, the analytics system 130 calculates a methylation beta series for each sequencing region in the aggregate sequencing region. The first methylation beta series is the set of methylation betas for CpGs in a particular region. For example, the first methylation beta series may be the methylation betas from 0 to k, where k is the number of CpGs in a particular sequencing region. The analytics system 130 may calculate the methylation beta series for each sequencing region.

At step 1020, the analytics system 130 calculates a second methylation beta series for matching sequencing regions from a cohort population. A matching sequencing region is a sequencing region at the same location (e.g., genomic location) as a sequencing region from the plurality of test sequences from the sample. The analytics system 130 calculates a second methylation beta series of a matching sequencing region in a manner similar to the first methylation beta series. The analytics system 130 calculates the second methylation beta series for each sequencing region in the aggregate sequencing region (by using the corresponding matching sequencing regions).

The analytics system 130 performs steps 1030-1050 for the sequencing region(s) of the aggregate sequencing region for which beta series were calculated.

At step 1030, the analytics system 130 calculates a set of sequence changepoints for the sequencing region. Each changepoint indicates a genomic position providing boundaries for adjacent subregions. As described above, the analytics system 130 may generate the sequence changepoints based on a difference between the first methylation beta series for the sequencing region and the second methylation beta series for the matching region. In particular, the analytics system 130 may generate endpoints such that the difference is maximized, in aggregate, across the generated subregions using the approaches described above.

At step 1040, the analytics system 130 segments the sequencing region into the sequencing subregions at the genomic positions indicated by the changepoints.

At step 1050, the analytics system 130 selects one or more of the sequencing subregions for the sample population. The analytics system 130 may select the sequencing subregions based on that subregion's propensity for indicating cancer. For example, the analytics system 130 may select one or more particular subregions whose beta differential indicates cancer presence (or non-presence).

The analytics system 130 may perform steps 1030-1050 for each sequencing region in the aggregate sequencing region.

In an example embodiment, the first example method 1000 results in a sample population including 19,690 regions and/or subregions in the sample population. The sensitivity is 61.3% with a false positive rate of 0.8% for a cancer classifier employing the method 1000. Both of these metrics are better than cancer classifier not employing the subregion selection method 1000 (57.9% sensitivity and 0.8% false positive rate).

III.D.III. Second Example Method

As described above, there are several methods of selecting sequencing subregions for use in a cancer classifier (e.g., step 820 of method 800). The analytics system 130 is configured to apply a region selection model (e.g., from models 150) to select sequencing subregions.

In a second example method of selecting sequencing subregions, the region selection model again relies on a comparison of methylation betas, but in a different manner than the first example method. In this example method, the region selection model is configured to understand that minimizing the average non-cancer betas in subregions across a region will result in subregions that provide better cancer signal for a classification model. In effect, the second approach treats non-cancer samples as "noise" signal and selects subregions from the region to minimize the "noise" signal.

To select these subregions indicative of non-cancer (or cancer) presence based on beta values, the region selection model calculates beta values for a non-cancer cohort as:

$$\text{beta}_k = \beta \text{ of aggregated noncancer cohorts at } k$$

where k is a CpG identifier starting at 0, and $\text{beta}_k$ spans from the first CpG of an interval to the last CpG of an interval (e.g., across all the sites in a particular sequence).

The region selection model applies a change point detection algorithm to the regions to identify subregions. That change point detection algorithms subdivides the beta value series over the region interval into N subregions. That is, the region selection model determines a number of subregions based on the beta values of the CpGs in that region.

When N is unknown, the region selection model solves a discrete optimization problem to divide the subregions, solving for:

$$\sum_{n=0}^{N} \min(V(n)) + \text{pen}(N)) \tag{8}$$

Using equation (4), V(n) is the cost function for one subregion. An example solution of V(n) using an L2 is:

$$V(n) = \sum_{k=0}^{K} \min\left(\text{beta}_k - (\underline{\text{beta}_{k=0 \ldots K}})^2\right) \tag{9}$$

where the mean of $\text{beta}_{k=0}$ K is the mean of betas from 0 to K, k is a CpG section that spans a subset of the CpGs in the interval of CpGs to be split.

Additionaly, pen(N) is defined as $$\text{pen}(N) = \log \log(\text{len}) * \text{sigma}^2 \tag{10}$$

where len is the length of the beta series and sigma is a factor for controlling the number of subregions generating in the splitting maximization.

In other words, given Eqns. (7)-(10), the region selection model generates subregion endpoints that minimize the beta across subregions for a non-cancer cohort. To provide additional detail, in this example, the region selection model looks at the non-cancer cohort in generating endpoints for subregions. Each of the generated subregions corresponds to a beta value representing that entire subregion (e.g., a mean). The region selection model generates subregions whose representative values, in aggregate, are minimized. Thus, moving, creating, and changing endpoints in the region changes the beta calculation for each subregion, allowing the analytics system 130 to minimize the beta for the subregions based on the non-cancer cohort.

Figure 11:
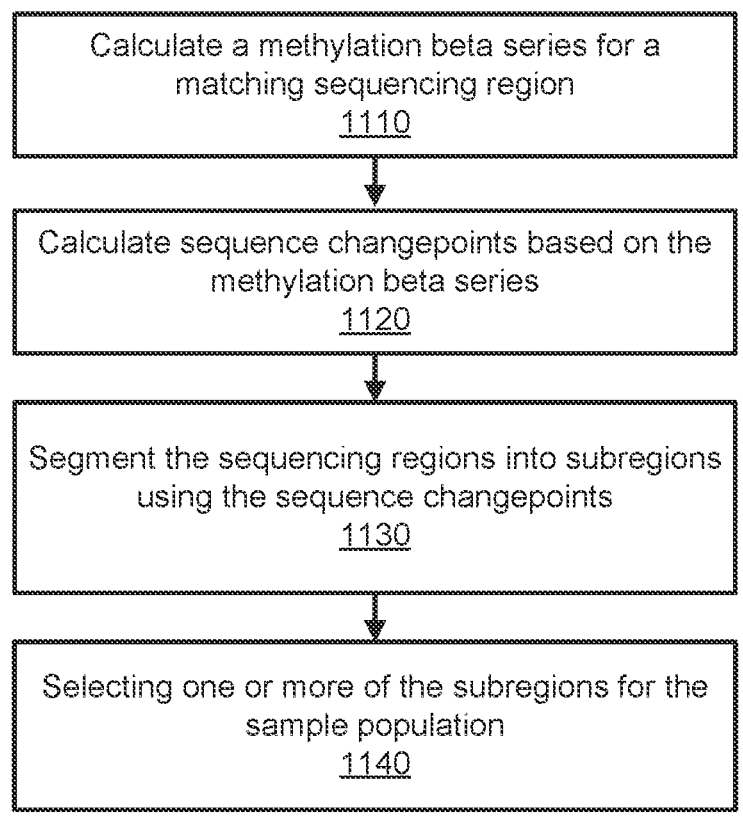
FIG. 11 is a flowchart of a method for selecting subregions in a second example method, according to an example embodiment.

FIG. 11 is a flowchart of a method for selecting subregions in a second example method, according to an example embodiment. The method 1100 may be performed as part of the selecting subregions step (e.g., step 820) of method 800, but could be performed independently or as part of another method or process. In the method 1100, the analytics system 130 employs a region selection model to select subregions for the sample population.

At step 1110, the analytics system 130 calculates a methylation beta series for matching sequencing regions from a cohort population. The matching sequencing regions are sequencing regions at the same location (e.g., genomic location) as the sequencing regions from the of the aggregate sequencing regions.

The analytics system 130 performs steps 1120-1140 for the sequencing region of the plurality of test sequences.

At step 1120, the analytics system 130 calculates a set of sequence changepoints for the sequencing region (by analyzing the matching sequencing region). Each changepoint indicates a genomic position providing boundaries between adjacent subregions. As described above, the analytics system 130 may generate the sequence changepoints based on the methylation beta series for the matching sequencing region. In particular, the analytics system 130 may generate endpoints such that, in aggregate across the generated subregions, the methylation beta series is minimized for the matching sequencing regions. That is, the representative methylation betas for the generated set of subregions for the matching subregions are minimized.

At step 1130, the analytics system 130 segments the sequencing region into the sequencing subregions at the genomic positions indicated by the changepoints generated from analyzing the matching sequencing region.

At step 1140, the analytics system 130 selects one or more of the sequencing subregions for the sample population. The analytics system 130 may select the sequencing subregions based on that subregion's propensity for indicating, or not-indicating, cancer. For example, the analytics system 130 may select particular subregions whose beta values indicates cancer non-presence (or cancer presence).

In an example embodiment, the second example method 1100 results in a sample population including 19,690 regions and/or subregions in the sample population. The sensitivity is 59.5% with a false positive rate of 1.0% for a cancer classifier employing the method 1100. Both of these metrics are better than cancer classifier not employing the subregion selection method 1000 (57.9% sensitivity and 0.8% false positive rate)

III.D.IV. Third Example Method

As described above, there are several methods of selecting sequencing subregions for use in a cancer classifier (e.g., step 820 of method 800). The analytics system 130 is configured to apply a region selection model (e.g., from models 150) to select sequencing subregions.

In a third example method, the region selection model creates subregions based on CpG density within a region. Recall again, referring to FIG. 6, that CpG's are located within a particular interval by chance. That is, because the test sequence intervals are windowed into regions according to genomic length (e.g., every 1000 base pairs), whether a region includes a CpG is largely random.

Thus, in the third example method, the region selection model creates subregions in "CpG space," rather than genomic space, to account for this randomness. There are several examples of subregion creation in CpG space. For instance, in a first example, rather than creating a region/subregion including 1000 base pairs in genomic space, the region selection model may create subregions including, for example, a user defined number of CpGs (e.g., 20, 100, etc.). In this example, the region selection model, in effect, changes the data represented in the histogram of FIG. 6A into a single bar such that all subregions include the same number of CpG's. In a similar example, the region selection model may group CpG's into subregions such that each subregion includes CpGs of similar length (e.g., 5% or less variation, within 10 base pairs in length, etc.). In this example, the region selection model may, in effect, bin the data of FIG. 6B into the regions reflected by the bars of FIG. 6A.

In a second example, the region selection model may create subregions in CpG space by identifying CpG clusters and creating a subregion for that cluster. A CpG cluster is two or more CpGs, each of which are less than a threshold distance away from one another in genomic space. For example, if the threshold distance is 40 base pairs, a CpG cluster may include a first, base pair CpG located 37 base pairs from a second, 53 base pair CpG, but could not include a third, 22 base pair CpG 81 base pairs from the first CpG and 62 base pairs from the second CpG.

Figure 12:
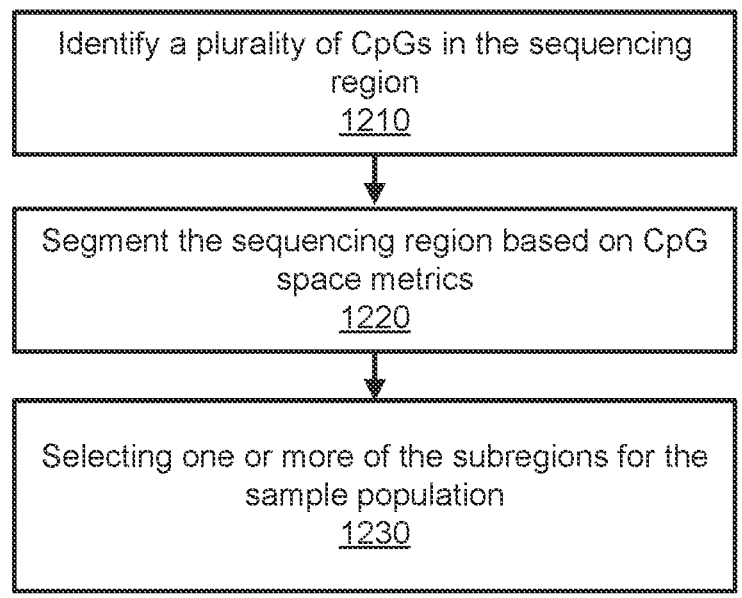
FIG. 12 is a flowchart of a method for selecting subregions in a third example method, according to an example embodiment.

FIG. 12 is a flowchart of a method for selecting subregions in a third example method, according to an example embodiment. The method 1200 may be performed as part of the selecting subregions step (e.g., step 820) of method 800, but could be performed independently or as part of another method or process. In the method 1200, the analytics system 130 employs a region selection model to select subregions for the sample population.

At step 1210, the analytics system 130 identifies a plurality of CpGs in the sequencing region. The analytics system may do so for each sequencing region in the aggregate sequencing region.

At step 1220, the analytics system 130 segments the sequencing region into a plurality of subregions using CpG space metrics. In a first example, the analytics system 130 generates subregions by placing CpGs of similar lengths into the same subregions. In a second example, the analytics system 130 generates subregions by placing approximately the same number of CpGs in each subregion. In a third example, the analytics system 130 generates subregions by identifying CpG clusters and grouping them into the same subregion. The analytics system 130 may perform this process for each sequencing subregion in the aggregate sequencing subregion.

At step 1230, the analytics system 130 selects one or more of the sequencing subregions for the sample population. The analytics system 130 may select the sequencing subregions based on that subregion's propensity for indicating, or not-indicating, cancer. For example, the analytics system 130 may select particular subregions whose CpGs indicate cancer non-presence, and/or may select other particular subregions whose CpGs indicate cancer presence. The analytics system 130 may perform this process for each sequencing subregion in the aggregate sequencing subregion.

In an example embodiment, the second example method 1200 results in a sample population including 19,226 regions and/or subregions in the sample population. The sensitivity is 59.7% with a false positive rate of 0.5% for a cancer classifier employing the method 1200.

III.D.V. Fourth Example Method

As described above, there are several methods of selecting sequencing subregions for use in a cancer classifier (e.g., step 820 of method 800). The analytics system 130 is configured to apply a region selection model (e.g., from models 150) to select sequencing subregions.

In a fourth example method, the region selection model again creates subregions based on CpG density within a region, but only does so for regions that are sufficiently dense. For instance, the analytics system 130 will identify a number of CpGs in each region. For each region including a number of CpGs greater than a threshold number of CpGs, the analytics system 130 segments the region into subregions. The analytics system 130 may segment the regions such that each subregion (1) includes the same number of base pairs in genomic space, (2) includes the same number of CpGs in CpG space, (3) includes one or more CpG clusters, and/or (4) includes CpGs of similar lengths.

The region selection model selects regions and subregions for the sample population for cancer identification. In an example embodiment, the region selection model selects both (1) regions having less than the threshold number of CpGs, and (2) subregions generated from regions having greater than the threshold number of CpGs for the sample population. In other examples, region selection model selects on or more regions having less than the threshold number of CpGs and/or one or more subregions generated from regions having greater than the threshold number of CpGs for the sample population.

Figure 13:
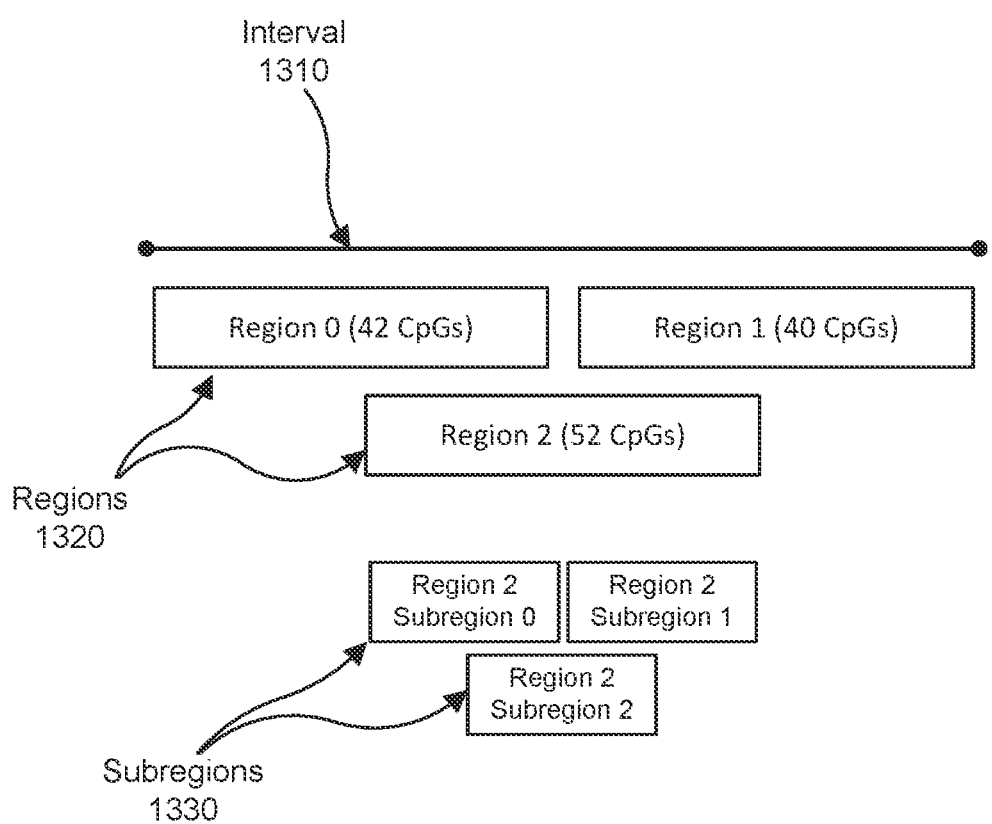
FIG. 13 shows an example of generating subregions from CpG dense regions, according to an example embodiment.

To illustrate, FIG. 13 shows an example of generating subregions from CpG dense regions, according to an example embodiment. FIG. 13 illustrates an interval 1310, or a portion of an interval, from a test sample. The interval is windowed into overlapping sequencing regions 1320. The analytics system 130 determines that Region 0 includes 42 CpGs, Region 1 includes 40 CpGs, and Region 2 includes 52 CpGs. Because Region 2 has a number of CpGs greater than a threshold number of CpGs (e.g., 50 CpGs, but other numbers of CpGs are also possible), the analytics system 130 segments Region 2 into subregions 1330. The analytics system 130 selects Region 0, Region 1, Region 2 Subregion 0, Region 2 Subregion 1, Region 2 Subregion 2 for the sample population.

Figure 14:
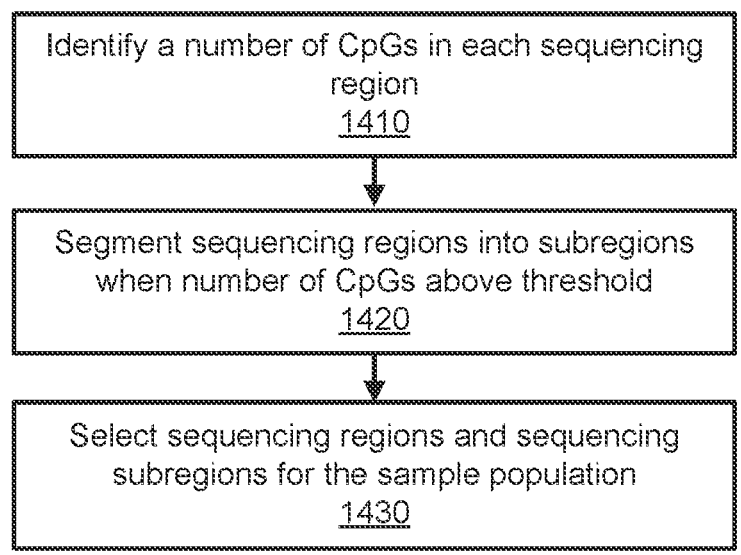
FIG. 14 is a flowchart of a method for selecting subregions in a fourth example method, according to an example embodiment.

FIG. 14 is a flowchart of a method for selecting subregions in a fourth example method, according to an example embodiment. The method 1400 may be performed as part of the selecting subregions step (e.g., step 820) of method 800, but could be performed independently or as part of another method or process. In the method 1400, the analytics system 130 employs a region selection model to select subregions for the sample population.

The analytics system 130 windows an interval into sequencing regions. At step 1410, the analytics system 130 identifies a number of CpGs in each of the sequencing regions.

At step 1420, the analytics system 130 segments the sequencing regions including greater than a threshold number of CpGs into sequencing subregions. For example, the analytics system 130 may segment a sequencing region by creating windowed and overlapping subregions in a manner similar to the creation of regions.

At step 1430, the analytics system 130 selects one or more of the sequencing subregions and one or more of the sequencing regions for the sample population. The analytics system 130 may select the sequencing subregions based on that subregion's propensity for indicating, or not-indicating, cancer. For example, the analytics system 130 may select a particular subregions whose CpGs indicate cancer non-presence and/or select particular subregions whose CpGs indicate cancer presence.

In an example embodiment, the second example method 1400 results in a sample population including 19,803 regions and/or subregions in the sample population. The sensitivity is 60.4% with a false positive rate of 0.7% for a cancer classifier employing the method 1400.

III.D.VI. Fifth Example Method

As described above, there are several methods of selecting sequencing subregions for use in a cancer classifier (e.g., step 820 of method 800). The analytics system 130 is configured to apply a region selection model (e.g., from models 150) to select sequencing subregions.

In a fifth example method, the region selection model may create and select subregions for the sample population based on mutual information scores.

To expand, the analytics system 130 may generate subregions for each region from an interval. Depending on the configuration, the analytics system 130 may generate the subregions based on any of the methods described hereinabove. For example, the analytics system 130 may segment the regions such that each subregion (1) includes the same number of base pairs in genomic space, (2) includes the same number of CpGs in CpG space, (3) includes one or more CpG clusters, and/or (4) includes CpGs of similar lengths, etc. In some embodiments, the analytics system 130 may create sub-subregions from each subregion. That is, the analytics system 130 may further segment each subregion into sub-subregions in a similar manner.

The analytics system 130 identifies a feature set for each region, group of subregions created from a region, and group of sub-subregions created from a subregion. In some cases the analytics system 130 may identify feature sets for each individual region, subregion, and sub-subregion. Using the identified feature sets, the analytics system 130 calculates a mutual information score for each region, group of subregions created from the regions, and group of sub-subregions created from the subregions (or individual regions, subregions, and sub-subregions). The mutual information scores indicate a propensity for the scored region, group of subregions, group of sub-subregions, individual subregions, and/or individual sub-subregions in indicating a cancer presence when applying a cancer classifier to a sample.

In turn, the analytics system 130 selects the regions, group of subregions, group of sub-subregions, individual subregions, and/or individual sub-subregions for the sample population that best indicate cancer (or non cancer). In an embodiment, the analytics system 130 selects one of a region, the group of subregions created from that region, or the group of sub-subregions created from the subregions for a sample population based on the mutual information scores for the same.

Figure 15A:
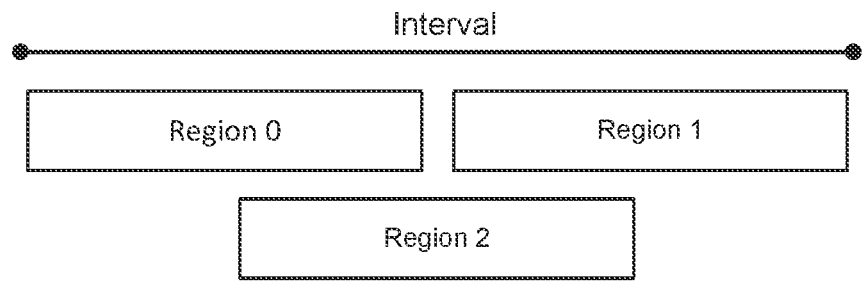
FIG. 15A shows a representation of an interval divided into regions, according to an example embodiment.
Figure 15B:
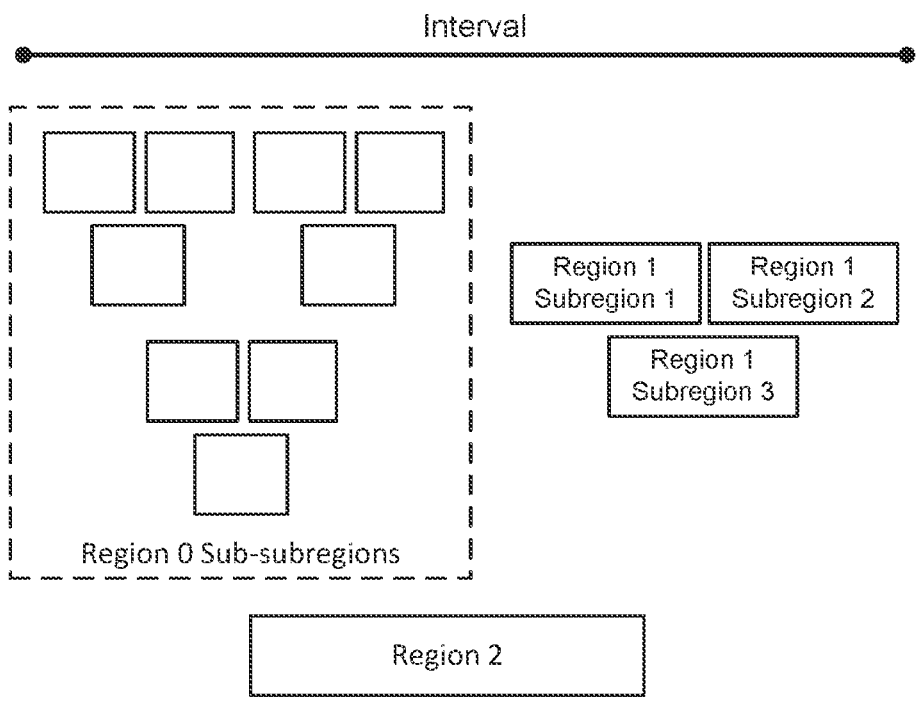
FIG. 15B illustrates regions, groups of sub-subregions, and groups of sub-subregions selected for a sample population, according to an example embodiment.

To illustrate, FIG. 15A shows a representation of an interval divided into regions, according to an example embodiment. The analytics system 130 divides the interval into regions in a manner like those described hereinabove. FIG. 15B illustrates regions, groups of sub-subregions, and groups of subregions selected for a sample population, according to an example embodiment. In FIG. 15B, the analytics system 130 segments each of the regions into a group of subregions (e.g., Region 1 and the Group of Region 1 Subregions) and segments each subregion into a group of sub-subregions (e.g., Region 0 sub-subregions). The analytics system 130 identifies a feature set for each of the regions, groups of subregions, and groups of sub-subregions. The analytics system 130 calculates a mutual information score for each of the regions, groups of subregions, and groups of subregions for the feature set. Based on the mutual information scores, the analytics system 130 selects the Region 0 sub-subregions, the Region 1 subregions, and Region 2 for the sample population.

Figure 16:
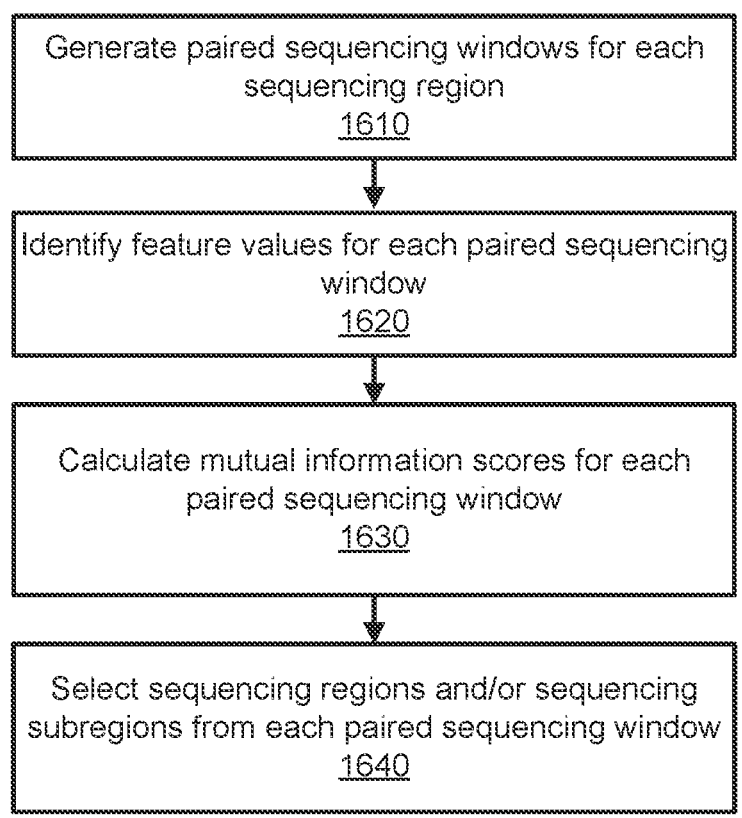
FIG. 16 is a flowchart of a method for selecting subregions in a fifth example method, according to an example embodiment.

FIG. 16 is a flowchart of a method for selecting subregions in a fifth example method, according to an example embodiment. The method 1600 may be performed as part of the selecting subregions step (e.g., step 820) of method 800, but could be performed independently or as part of another method or process. In the method 1600, the analytics system 130 employs a region selection model to select subregions for the sample population.

The analytics system 130 windows an interval into sequencing regions. At step 1610, the analytics system 130 generates a paired sequencing window for each of the sequencing regions. A paired sequencing window includes the as generated sequencing region, and a set of sequencing subregions generated from that sequencing regions. In some examples, the paired sequencing region may include a set sequencing sub-subregions generated from each sequencing subregion in the set of subregions.

Steps 1620-1640 occur for each of the generated paired sequencing windows.

At step 1620, the analytics system 130 identifies feature values for a paired sequencing window. That is, the analytics system 130 identifies feature values for the sequencing region and the set of sequencing subregions (as a group, or individually).

At step 1630, the analytics system 130 calculates mutual information scores for the paired sequencing window. That is, the analytics system 130 calculates a mutual information score for the sequencing region and the set of sequencing subregions (as a group, or individually).

At step 1640, the analytics system 130 selects one or more of the subregion and the set of subregions for the sample population (as a group, or individually) from the paired sequencing window. In an example embodiment, the analytics system 130 will select either the region or the set of subregions for the sample population from the sequencing window.

Because 1620-1640 occur for each paired sequencing window, the sample population includes some combination of regions and subregions.

In examples where the paired sequencing windows include sub-subregions, the analytics system 130 may generate feature sets and mutual inference scores for those sub-subregions such that the sample population may include regions, subregions and sub-subregions.

In an example embodiment, the second example method 1600 results in a sample population including 19,745 regions and/or subregions in the sample population. The sensitivity is 61.8% with a false positive rate of 0.9% for a cancer classifier employing the method 1600.

III.D.VII. Sixth Example Method

As described above, there are several methods of selecting sequencing subregions for use in a cancer classifier (e.g., step 820 of method 800). The analytics system 130 is configured to apply a region selection model (e.g., from models 150) to select sequencing subregions.

In a sixth example method, the region selection model may create feature value ensembles and select a sample population based on mutual information scores and cancer classification results.

The sixth example method is similar to the firth example method in that it includes arrays of regions, subregions, and sub-subregions. That is, the analytics system 130 generates a group of subregions for each region, and a group of sub-subregions for each subregion.

The sixth example method is dissimilar form the fifth example method in that the sixth example method generates a feature set ensemble ("ensemble"). The ensemble includes some number N of feature value sets. Each of the feature value sets in the ensemble may be different from each other feature value set in the ensemble. That is, in an example, at least one feature value is different from feature values in other feature value sets in the ensemble.

The analytics system 130 calculates a mutual information score for each region, group of subregions (individually or as a group), and each group of sub-subregions (individually or as a group) for each set of feature value set in the ensemble. Based on the mutual information score, the analytics system 130 selects regions, subregions, or sub-subregions for the sample population.

In some example embodiments, in lieu of, or in addition to, the analytics system 130 may determine a cancer classification metric for each combination of set of feature values, region, group of subregions (individually or as a group), and group of sub-subregions (individually or as a group). In other words, the analytics system 130 generates a cancer classification matrix whose values represent the ability of each combination of identifying cancer in a sample. In this case, the analytics system 130 may select regions, groups of subregions, and/or groups of subregions for the sample population by the cancer classification metrics in the cancer classification matrix.

Figure 17:
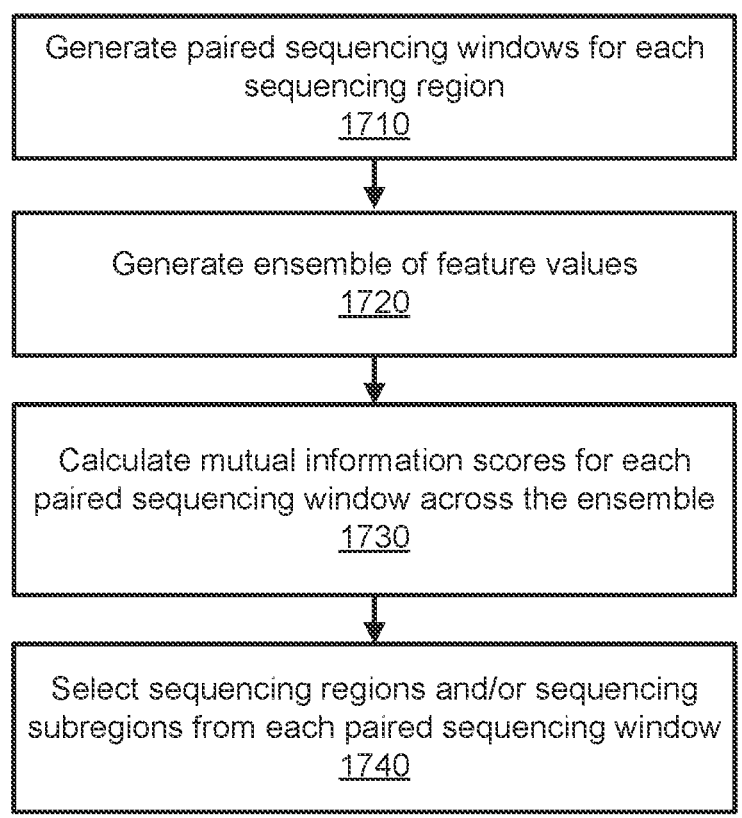
FIG. 17 is a flowchart of a method for selecting subregions in a third example method, according to an example embodiment The figures depict various embodiments for purposes of illustration only. One skilled in the art will readily recognize from the following discussion that alternative embodiments of the structures and methods illustrated herein may be employed without departing from the principles described herein.

FIG. 17 is a flowchart of a method for selecting subregions in a third example method, according to an example embodiment. The method 1700 may be performed as part of the selecting subregions step (e.g., step 820) of method 800, but could be performed independently or as part of another method or process. In the method, the analytics system 130 employs a region selection model to select subregions for the sample population.

The analytics system 130 windows an interval into sequencing regions. At step 1710, the analytics system 130 generates a paired sequencing window for each of the sequencing regions. A paired sequencing window includes the as generated sequencing region, and a set of sequencing subregions generated from that sequencing regions. In some examples, the paired sequencing region may include a set sequencing sub-subregions generated from each sequencing subregion in the set of subregions.

At step 1720, the analytics system generates an ensemble. The ensemble comprises some number of feature value sets. Typically, each feature value set is at least somewhat different than other feature value sets in the ensemble.

Steps 1730-1740 occur for each of the generated paired sequencing windows.

The analytics system calculates a mutual information score for each of the regions and subregions in a paired sequencing window using the ensemble. That is, the analytics system calculates a mutual information score for the regions and groups of subregions for each feature value set in the ensemble.

At step 1740, the analytics system selects regions and subregions for the sample population based on the mutual information scores across all feature value sets in the ensemble.

In some embodiments, the analytics system may additionally, or alternatively, select regions and subregions for the sample population based on cancer classification metrics. That is, the analytics system may determine a quantify (e.g., the cancer classification metric) how well each combination of feature value set, region, and subregion classify cancer in a sample. In effect, the analytics system creates a classification matrix reflecting the various combinations of feature values, regions, and subregions in identifying a cancer presence, and selects regions and subregions for the sample population based on the cancer classification metrics in the matrix.

In an example embodiment, the second example method 1700 results in a sample population including 19,701 regions and/or subregions in the sample population. The sensitivity is 61.9% with a false positive rate of 0.9% for a cancer classifier employing the method 1700.

III.E Deployment of a Cancer Classifier

During use of the cancer classifier, the analytics system 130 can obtain a test sample from a subject of unknown cancer type. The analytics system 130 may process the test sample comprised of DNA molecules with any combination of the processes 300, 400, and 420 to achieve a set of anomalous fragments. The analytics system 130 can determine a test feature vector for use by the cancer classifier according to similar principles discussed in the process 500. The analytics system 130 can calculate an anomaly score for each CpG site in a plurality of CpG sites in use by the cancer classifier. For example, the cancer classifier receives as input feature vectors inclusive of anomaly scores for 1,000 selected CpG sites. The analytics system 130 can thus determine a test feature vector inclusive of anomaly scores for the 1,000 selected CpG sites based on the set of anomalous fragments. The analytics system 130 can calculate the anomaly scores in a same manner as the training samples. In some embodiments, the analytics system 130 defines the anomaly score as a binary score based on whether there is a hypermethylated or hypomethylated fragment in the set of anomalous fragments that encompasses the CpG site.

The analytics system 130 can then input the test feature vector into the cancer classifier. The function of the cancer classifier can then generate a cancer prediction based on the classification parameters trained in the process 500 and the test feature vector. In the first manner, the cancer prediction can be binary and selected from a group consisting of "cancer" or non-cancer;" in the second manner, the cancer prediction is selected from a group of many cancer types and "non-cancer." In additional embodiments, the cancer prediction has predictions values for each of the many cancer types. Moreover, the analytics system 130 may determine that the test sample is most likely to be of one of the cancer types. Following the example above with the cancer prediction for a test sample as 65% likelihood of breast cancer, 25% likelihood of lung cancer, and 10% likelihood of non-cancer, the analytics system 130 may determine that the test sample is most likely to have breast cancer. In another example, where the cancer prediction is binary as 60% likelihood of non-cancer and 40% likelihood of cancer, the analytics system 130 determines that the test sample is most likely not to have cancer. In additional embodiments, the cancer prediction with the highest likelihood may still be compared against a threshold (e.g., 40%, 50%, 60%, 70%) in order to call the test subject as having that cancer type. If the cancer prediction with the highest likelihood does not surpass that threshold, the analytics system 130 may return an inconclusive result.

In additional embodiments, the analytics system 130 chains a cancer classifier trained in step 960 of the process 900 with another cancer classifier trained in step 970 or the process 900. The analytics system 130 can input the test feature vector into the cancer classifier trained as a binary classifier in step 960 of the process 900. The analytics system 130 can receive an output of a cancer prediction. The cancer prediction may be binary as to whether the test subject likely has or likely does not have cancer. In other implementations, the cancer prediction includes prediction values that describe likelihood of cancer and likelihood of non-cancer. For example, the cancer prediction has a cancer prediction value of 85% and the non-cancer prediction value of 15%. The analytics system 130 may determine the test subject to likely have cancer. Once the analytics system 130 determines a test subject is likely to have cancer, the analytics system 130 may input the test feature vector into a multiclass cancer classifier trained to distinguish between different cancer types. The multiclass cancer classifier can receive the test feature vector and returns a cancer prediction of a cancer type of the plurality of cancer types. For example, the multiclass cancer classifier provides a cancer prediction specifying that the test subject is most likely to have ovarian cancer. In another implementation, the multiclass cancer classifier provides a prediction value for each cancer type of the plurality of cancer types. For example, a cancer prediction may include a breast cancer type prediction value of 40%, a colorectal cancer type prediction value of 15%, and a liver cancer prediction value of 45%.

According to generalized embodiment of binary cancer classification, the analytics system 130 can determine a cancer score for a test sample based on the test sample's sequencing data (e.g., methylation sequencing data, SNP sequencing data, other DNA sequencing data, RNA sequencing data, etc.). The analytics system 130 can compare the cancer score for the test sample against a binary threshold cutoff for predicting whether the test sample likely has cancer. The binary threshold cutoff can be tuned using TOO thresholding based on one or more TOO subtype classes. The analytics system 130 may further generate a feature vector for the test sample for use in the multiclass cancer classifier to determine a cancer prediction indicating one or more likely cancer types.

The classifier may be used to determine the disease state of a test subject, e.g., a subject whose disease status is unknown. The method can include obtaining a test genomic data construct (e.g., single time point test data), in electronic form, that includes a value for each genomic characteristic in the plurality of genomic characteristics of a corresponding plurality of nucleic acid fragments in a biological sample obtained from a test subject. The method can then include applying the test genomic data construct to the test classifier to thereby determine the state of the disease condition in the test subject. The test subject may not be previously diagnosed with the disease condition.

The classifier can be a temporal classifier that uses at least (i) a first test genomic data construct generated from a first biological sample acquired from a test subject at a first point in time, and (ii) a second test genomic data construct generated from a second biological sample acquired from a test subject at a second point in time.

The trained classifier can be used to determine the disease state of a test subject, e.g., a subject whose disease status is unknown. In this case, the method can include obtaining a test time-series data set, in electronic form, for a test subject, where the test time-series data set includes, for each respective time point in a plurality of time points, a corresponding test genotypic data construct including values for the plurality of genotypic characteristics of a corresponding plurality of nucleic acid fragments in a corresponding biological sample obtained from the test subject at the respective time point, and for each respective pair of consecutive time points in the plurality of time points, an indication of the length of time between the respective pair of consecutive time points. The method can then include applying the test genotypic data construct to the test classifier to thereby determine the state of the disease condition in the test subject. The test subject may not be previously diagnosed with the disease condition.

IV. Applications

In some embodiments, the methods, analytic systems and/or classifier of the present invention can be used to detect the presence of cancer, monitor cancer progression or recurrence, monitor therapeutic response or effectiveness, determine a presence or monitor minimum residual disease (MRD), or any combination thereof. For example, as described herein, a classifier can be used to generate a probability score (e.g., from 0 to 100) describing a likelihood that a test feature vector is from a subject with cancer. In some embodiments, the probability score is compared to a threshold probability to determine whether or not the subject has cancer. In other embodiments, the likelihood or probability score can be assessed at multiple different time points (e.g., before or after treatment) to monitor disease progression or to monitor treatment effectiveness (e.g., therapeutic efficacy). In still other embodiments, the likelihood or probability score can be used to make or influence a clinical decision (e.g., diagnosis of cancer, treatment selection, assessment of treatment effectiveness, etc.). For example, in one embodiment, if the probability score exceeds a threshold, a physician can prescribe an appropriate treatment.

IV.A. Early Detection of Cancer

In some embodiments, the methods and/or classifier of the present invention are used to detect the presence or absence of cancer in a subject suspected of having cancer. For example, a classifier (e.g., as described above in Section III and exampled in Section V) can be used to determine a cancer prediction describing a likelihood that a test feature vector is from a subject that has cancer.

In one embodiment, a cancer prediction is a likelihood (e.g., scored between 0 and 100) for whether the test sample has cancer (i.e. binary classification). Thus, the analytics system 130 may determine a threshold for determining whether a test subject has cancer. For example, a cancer prediction of greater than or equal to 60 can indicate that the subject has cancer. In still other embodiments, a cancer prediction greater than or equal to 65, greater than or equal to 70, greater than or equal to 75, greater than or equal to 80, greater than or equal to 85, greater than or equal to 90, or greater than or equal to 95 indicates that the subject has cancer. In other embodiments, the cancer prediction can indicate the severity of disease. For example, a cancer prediction of 80 may indicate a more severe form, or later stage, of cancer compared to a cancer prediction below 80 (e.g., a probability score of 70). Similarly, an increase in the cancer prediction over time (e.g., determined by classifying test feature vectors from multiple samples from the same subject taken at two or more time points) can indicate disease progression or a decrease in the cancer prediction over time can indicate successful treatment.

In another embodiment, a cancer prediction comprises many prediction values, wherein each of a plurality of cancer types being classified (i.e. multiclass classification) for has a prediction value (e.g., scored between 0 and 100). The prediction values may correspond to a likelihood that a given training sample (and during inference, training sample) has each of the cancer types. The analytics system 130 may identify the cancer type that has the highest prediction value and indicate that the test subject likely has that cancer type. In other embodiments, the analytics system 130 further compares the highest prediction value to a threshold value (e.g., 50, 55, 60, 65, 70, 75, 80, 85, etc.) to determine that the test subject likely has that cancer type. In other embodiments, a prediction value can also indicate the severity of disease. For example, a prediction value greater than 80 may indicate a more severe form, or later stage, of cancer compared to a prediction value of 60. Similarly, an increase in the prediction value over time (e.g., determined by classifying test feature vectors from multiple samples from the same subject taken at two or more time points) can indicate disease progression or a decrease in the prediction value over time can indicate successful treatment.

According to aspects of the invention, the methods and systems of the present invention can be trained to detect or classify multiple cancer indications. For example, the methods, systems and classifiers of the present invention can be used to detect the presence of one or more, two or more, three or more, five or more, ten or more, fifteen or more, or twenty or more different types of cancer.

Examples of cancers that can be detected using the methods, systems and classifiers of the present invention include carcinoma, lymphoma, blastoma, sarcoma, and leukemia or lymphoid malignancies. More particular examples of such cancers include, but are not limited to, squamous cell cancer (e.g., epithelial squamous cell cancer), skin carcinoma, melanoma, lung cancer, including small-cell lung cancer, non-small cell lung cancer ("NSCLC"), adenocarcinoma of the lung and squamous carcinoma of the lung, cancer of the peritoneum, gastric or stomach cancer including gastrointestinal cancer, pancreatic cancer (e.g., pancreatic ductal adenocarcinoma), cervical cancer, ovarian cancer (e.g., high grade serous ovarian carcinoma), liver cancer (e.g., hepatocellular carcinoma (HCC)), hepatoma, hepatic carcinoma, bladder cancer (e.g., urothelial bladder cancer), testicular (germ cell tumor) cancer, breast cancer (e.g., HER2 positive, HER2 negative, and triple negative breast cancer), brain cancer (e.g., astrocytoma, glioma (e.g., glioblastoma)), colon cancer, rectal cancer, colorectal cancer, endometrial or uterine carcinoma, salivary gland carcinoma, kidney or renal cancer (e.g., renal cell carcinoma, nephroblastoma or Wilms' tumor), prostate cancer, vulval cancer, thyroid cancer, anal carcinoma, penile carcinoma, head and neck cancer, esophageal carcinoma, and nasopharyngeal carcinoma (NPC). Additional examples of cancers include, without limitation, retinoblastoma, thecoma, arrhenoblastoma, hematological malignancies, including but not limited to non-Hodgkin's lymphoma (NHL), multiple myeloma and acute hematological malignancies, endometriosis, fibrosarcoma, choriocarcinoma, laryngeal carcinomas, Kaposi's sarcoma, Schwannoma, oligodendroglioma, neuroblastomas, rhabdomyosarcoma, osteogenic sarcoma, leiomyosarcoma, and urinary tract carcinomas.

In some embodiments, the cancer is one or more of anorectal cancer, bladder cancer, breast cancer, cervical cancer, colorectal cancer, esophageal cancer, gastric cancer, head & neck cancer, hepatobiliary cancer, leukemia, lung cancer, lymphoma, melanoma, multiple myeloma, ovarian cancer, pancreatic cancer, prostate cancer, renal cancer, thyroid cancer, uterine cancer, or any combination thereof.

In some embodiments, the one or more cancer can be a "high-signal" cancer (defined as cancers with greater than 50% 5-year cancer-specific mortality), such as anorectal, colorectal, esophageal, head & neck, hepatobiliary, lung, ovarian, and pancreatic cancers, as well as lymphoma and multiple myeloma. High-signal cancers tend to be more aggressive and typically have an above-average cell-free nucleic acid concentration in test samples obtained from a patient.

IV.B. Cancer and Treatment Monitoring

In some embodiments, the cancer prediction can be assessed at multiple different time points (e.g., or before or after treatment) to monitor disease progression or to monitor treatment effectiveness (e.g., therapeutic efficacy). For example, the present invention include methods that involve obtaining a first sample (e.g., a first plasma cfDNA sample) from a cancer patient at a first time point, determining a first cancer prediction therefrom (as described herein), obtaining a second test sample (e.g., a second plasma cfDNA sample) from the cancer patient at a second time point, and determining a second cancer prediction therefrom (as described herein).

In certain embodiments, the first time point is before a cancer treatment (e.g., before a resection surgery or a therapeutic intervention), and the second time point is after a cancer treatment (e.g., after a resection surgery or therapeutic intervention), and the classifier is utilized to monitor the effectiveness of the treatment. For example, if the second cancer prediction decreases compared to the first cancer prediction, then the treatment is considered to have been successful. However, if the second cancer prediction increases compared to the first cancer prediction, then the treatment is considered to have not been successful. In other embodiments, both the first and second time points are before a cancer treatment (e.g., before a resection surgery or a therapeutic intervention). In still other embodiments, both the first and the second time points are after a cancer treatment (e.g., after a resection surgery or a therapeutic intervention). In still other embodiments, cfDNA samples may be obtained from a cancer patient at a first and second time point and analyzed. e.g., to monitor cancer progression, to determine if a cancer is in remission (e.g., after treatment), to monitor or detect residual disease or recurrence of disease, or to monitor treatment (e.g., therapeutic) efficacy.

The test samples can be obtained from a cancer patient over any set of time points and analyzed in accordance with the methods of the invention to monitor a cancer state in the patient. In some embodiments, the first and second time points are separated by an amount of time that ranges from about 15 minutes up to about 30 years, such as about 30 minutes, such as about 1, 2, 3, 4, 5, 6, 7, 8, 9, 10, 11, 12, 13, 14, 15, 16, 17, 18, 19, 20, 21, 22, 23, or about 24 hours, such as about 1, 2, 3, 4, 5, 10, 15, 20, 25 or about 50 days, or such as about 1, 2, 3, 4, 5, 6, 7, 8, 9, 10, 11, or 12 months, or such as about 1, 1.5, 2, 2.5, 3, 3.5, 4, 4.5, 5, 5.5, 6, 6.5, 7, 7.5, 8, 8.5, 9, 9.5, 10, 11, 11.5, 12, 12.5, 13, 13.5, 14, 14.5, 15, 15.5, 16, 16.5, 17, 17.5, 18, 18.5, 19, 19.5, 20, 21, 21.5, 22, 22.5, 23, 23.5, 24, 24.5, 25, 25.5, 26, 26.5, 27, 27.5, 28, 28.5, 29, 29.5 or about 30 years. In other embodiments, test samples can be obtained from the patient at least once every 5 months, at least once every 6 months, at least once a year, at least once every 2 years, at least once every 3 years, at least once every 4 years, or at least once every 5 years.

IV.C. Treatment

In still another embodiment, the cancer prediction can be used to make or influence a clinical decision (e.g., diagnosis of cancer, treatment selection, assessment of treatment effectiveness, etc.). For example, in one embodiment, if the cancer prediction (e.g., for cancer or for a particular cancer type) exceeds a threshold, a physician can prescribe an appropriate treatment (e.g., a resection surgery, radiation therapy, chemotherapy, and/or immunotherapy).

A classifier (as described herein) can be used to determine a cancer prediction that a sample feature vector is from a subject that has cancer. In one embodiment, an appropriate treatment (e.g., resection surgery or therapeutic) is prescribed when the cancer prediction exceeds a threshold. For example, in one embodiment, if the cancer prediction is greater than or equal to 60 one or more appropriate treatments are prescribed. In another embodiment, if the cancer prediction is greater than or equal to 65, greater than or equal to 70, greater than or equal to 75, greater than or equal to 80, greater than or equal to 85, greater than or equal to 90, or greater than or equal to 95, one or more appropriate treatments are prescribed. In other embodiments, the cancer prediction can indicate the severity of disease. An appropriate treatment matching the severity of the disease may then be prescribed.

In some embodiments, the treatment is one or more cancer therapeutic agents selected from the group consisting of a chemotherapy agent, a targeted cancer therapy agent, a differentiating therapy agent, a hormone therapy agent, and an immunotherapy agent. For example, the treatment can be one or more chemotherapy agents selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, platinum-based agents and any combination thereof. In some embodiments, the treatment is one or more targeted cancer therapy agents selected from the group consisting of signal transduction inhibitors (e.g. tyrosine kinase and growth factor receptor inhibitors), histone deacetylase (HDAC) inhibitors, retinoic receptor agonists, proteosome inhibitors, angiogenesis inhibitors, and monoclonal antibody conjugates. In some embodiments, the treatment is one or more differentiating therapy agents including retinoids, such as tretinoin, alitretinoin and bexarotene. In some embodiments, the treatment is one or more hormone therapy agents selected from the group consisting of anti-estrogens, aromatase inhibitors, progestins, estrogens, anti-androgens, and GnRH agonists or analogs. In one embodiment, the treatment is one or more immunotherapy agents selected from the group comprising monoclonal antibody therapies such as rituximab (RITUXAN) and alemtuzumab (CAMPATH), non-specific immunotherapies and adjuvants, such as BCG, interleukin-2 (IL-2), and interferon-alfa, immunomodulating drugs, for instance, thalidomide and lenalidomide (REVLIMID). It is within the capabilities of a skilled physician or oncologist to select an appropriate cancer therapeutic agent based on characteristics such as the type of tumor, cancer stage, previous exposure to cancer treatment or therapeutic agent, and other characteristics of the cancer.

V. Additional Considerations

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Any of the steps, operations, or processes described herein as being performed by the analytics system 130 may be performed or implemented with one or more hardware or software modules of the apparatus, alone or in combination with other computing devices. In one embodiment, a software module is implemented with a computer program product comprising a computer-readable medium containing computer program code, which can be executed by a computer processor for performing any or all of the steps, operations, or processes described.

What is claimed is:

1. A method for classifying a variant in a cell free nucleic acid sample, the method comprising:

training a machine-learned model as a cancer classifier, the training comprising:

accessing a plurality of cohort test sequences from a cohort population, with each cohort test sequence of the plurality of cohort test sequences comprising one or more cohort sequencing regions of a plurality of cohort sequencing regions, wherein the plurality of cohort sequencing regions, in aggregate, form an aggregated cohort sequencing region;

calculating, for each of the cohort sequencing regions in the aggregated cohort sequencing region, an indicativeness for the cohort sequencing region quantifying a degree to which candidate variants in the cohort sequencing region indicate cancer presence;

selecting one or more cohort sequencing regions from the aggregated cohort sequencing region as one or more indicative regions to generate a training population, the selected indicative regions corresponding to cohort sequencing regions having calculated indicativenesses indicating cancer presence, wherein the training population is smaller than the aggregate cohort sequencing region; and training, using the training population, the machine-learned model to identify test sequences with candidate variants that are indicative of cancer and identify cancer in test samples using the indicative test sequences;

accessing a plurality of test sequences from a test sample with each test sequence of the plurality of test sequences comprising one or more sequencing regions of a plurality of sequencing regions, the plurality of sequencing regions, in aggregate, forming an aggregate sequencing region;

selecting one or more indicative regions from the aggregate sequencing region formed from the plurality of test sequences to generate a sample population, the selected one or more indicative regions corresponding to a cancer presence in the test sample, wherein the sample population is smaller than the aggregate sequencing region; and applying the machine-learned model to the generated sample population to identify the cancer presence in the test sample, the machine-learned model:

identifying a candidate variant in an indicative region of the one or more selected indicative regions for the sample population;

comparing a test feature set of the candidate variant to a cohort feature set of a matching sequencing subregion from the cohort population; and determining the candidate variant is indicative of the cancer in the test sample based on the compared test feature set and cohort feature set.

2. The method of claim 1, selecting the one or more indicative regions from the aggregate sequencing region for the sample population further comprises:

calculating a first methylation beta series for a sequencing region in the aggregate sequencing region;

calculating a second methylation beta series for a matching sequencing region from the cohort population, the matching sequencing region at a same genomic location as the sequencing region in the aggregate sequencing region; and for the sequencing region in the aggregate sequencing region:

calculating a set of sequence changepoints in the sequencing region based on a difference between the first methylation beta series and the second methylation beta series, and wherein the set of sequence changepoints identify positions in the sequencing region for segmenting the sequencing region into a plurality of sequencing subregions, segmenting the sequencing region into the plurality of sequencing subregions at the identified positions of the set of sequence changepoints, and selecting one or more of the sequencing subregions of the plurality of sequencing subregions for the sample population.

3. The method of claim 2, wherein, in aggregate across the plurality of sequencing subregions, the set of sequence changepoints maximizes a difference between the first methylation beta series for the sequencing region and the second methylation beta series for the matching sequencing region.

4. The method of claim 1, wherein selecting the one or more indicative regions from the aggregate sequencing region for the sample population further comprises:

calculating a methylation beta series for a matching sequencing region from the cohort population, wherein:

the methylation beta series quantifies changes in methylation levels within sequencing regions, and the matching sequencing region is at a same location as a sequencing region from the aggregate sequencing region; and for the sequencing region in the aggregate sequencing region:

calculating a set of sequence changepoints in the matching sequencing region based on the methylation beta series, and wherein the set of sequence changepoints identify positions in the matching sequencing region for segmenting the sequencing region into sequencing subregions;

segmenting the sequencing region into a plurality of sequencing subregions at the identified positions of the set of sequence changepoints in the matching sequencing region; and selecting one or more of the sequencing subregions of the plurality of sequencing subregions for the sample population.

5. The method of claim 4, wherein, in aggregate across the sequencing subregions, the set of sequence changepoints minimizes the methylation beta series for the cohort population.

6. The method of claim 1, selecting the one or more indicative regions from the aggregate sequencing region for the sample population further comprises:

identifying a plurality of CpGs in the aggregate sequencing region, each of the CpGs having a genomic length of a plurality of genomic lengths;

segmenting the aggregate sequencing region into a plurality of sequencing subregions, wherein each of the sequencing subregions comprises a subset of CpGs from the plurality of CpGs having substantially similar genomic lengths; and selecting one or more of the plurality of sequencing subregions for the sample population.

7. The method of claim 1, selecting the one or more indicative regions from the aggregate sequencing region for the sample population further comprises:

identifying a plurality of CpGs in the aggregate sequencing region;

segmenting the aggregate sequencing region into a plurality of sequencing subregions, wherein each sequencing subregion of the plurality comprises a number of CpGs less than a threshold number of CpGs; and
selecting one or more of the plurality of sequencing subregions for the sample population.

8. The method of claim 1, selecting the one or more indicative regions from the aggregate sequencing region for the sample population further comprises:
identifying a plurality of CpGs in the aggregate sequencing region;
identifying a plurality of CpG clusters using the identified plurality of CpGs, each CpG cluster comprising two or more CpGs less than a threshold genomic distance away from other CpGs in the cluster;
segmenting the aggregate sequencing region into a plurality of sequencing subregions, wherein each of the sequencing subregion of the plurality comprises a CpG cluster of the plurality of CpG clusters; and
selecting one or more of the plurality of sequencing subregions for the sample population.

9. The method of claim 8, wherein selecting the one or more indicative regions for the sample population comprises identifying CpG clusters having genomic locations overlapping with genomic locations of test sequences generated by a sequencing panel for the sample.

10. The method of claim 1, wherein selecting the one or more indicative regions from the aggregate sequencing region for the sample population further comprises:
calculating a genomic length for each of the plurality of sequencing regions;
for each of the plurality of sequencing regions whose genomic length is greater than a threshold genomic length, segmenting the sequencing region into a plurality of sequencing subregions such that each of the plurality of sequencing subregions has a genomic length less than the threshold genomic length; and
selecting, for the sample population, at least one the plurality of sequencing regions and at least one of the plurality of sequencing subregions.

11. The method of claim 1, wherein selecting the one or more sequencing subregions from the aggregate sequencing region for the sample population further comprises:
identifying a number of CpGs in each sequencing region of the plurality of sequencing regions;
for each of the plurality of sequencing regions having a number of CpGs higher than a threshold number of CpGs, segmenting the sequencing region into a plurality of sequencing subregions such that each of the plurality of sequencing subregions comprises less than the threshold number of CpGs; and
selecting, for the sample population, at least one of the plurality of sequencing regions and at least one of the plurality of sequencing subregions.

12. The method of claim 1, wherein selecting the one or more indicative regions from the aggregate sequencing region for the sample population further comprises:
generating a plurality of paired sequencing windows for the aggregate sequencing region, each paired sequencing window comprising:
a sequencing region of the plurality of sequencing regions; and
a plurality of sequencing subregions generated from the sequencing region;
for each of the paired sequencing windows of the plurality:
identifying feature values for the sequencing region;
identifying feature values for each of the plurality of sequencing subregions; and
calculating, using the identified feature values, mutual information scores for each of the plurality of sequencing subregions and the sequencing region; and
selecting, based on the mutual information scores, at least one of the plurality of sequencing subregions or the sequencing region for the sample population.

13. The method of claim 1, wherein selecting the one or more indicative regions from the aggregate sequencing region for the sample population further comprises:
generating a plurality of paired sequencing windows for the aggregate sequencing region, each paired sequencing window comprising:
a sequencing region of the plurality of sequencing regions; and
a plurality of sequence subregions generated from the sequencing region;
generating an ensemble comprising a plurality of feature value sets, wherein each feature value set in the ensemble comprises at least one feature value different from feature values of other feature value sets in the ensemble;
for each of the paired sequencing windows of the plurality:
calculating, for each feature value set in the ensemble, mutual information scores for the sequencing region and each of the plurality of sequencing subregions; and
selecting, based on the mutual information scores, at least one of the plurality of sequencing subregions or the sequencing region for the sample population.

14. The method of claim 13, wherein selecting sequencing subregions and sequencing regions for the sample population is further based on a cancer classification metric across a classification matrix comprising a plurality of elements, wherein the plurality of elements in the classification matrix represent each possible combination of feature value sets from the ensemble, sequencing regions of the plurality, and sequencing subregions generated from sequencing regions.

15. A non-transitory computer-readable storage medium comprising computer program instructions for classifying a variant in a cell free nucleic acid sample, the computer program instructions, when executed by one or more processors, causing the one or more processors to:
train a machine-learned model as a cancer classifier, the training comprising:
accessing a plurality of cohort test sequences from a cohort population, with each cohort test sequence of the plurality of cohort test sequences comprising one or more cohort sequencing regions of a plurality of cohort sequencing regions, wherein the plurality of cohort sequencing regions, in aggregate, form an aggregated cohort sequencing region;
calculating, for each of the cohort sequencing regions in the aggregated cohort sequencing region, an indicativeness for the cohort sequencing region quantifying a degree to which candidate variants in the cohort sequencing region indicate cancer presence;
selecting one or more cohort sequencing regions from the aggregated cohort sequencing region as one or more indicative regions to generate a training population, the selected indicative regions corresponding to cohort sequencing regions having calculated indicativenesses indicating cancer presence, wherein the training population is smaller than the aggregate cohort sequencing region; and training, using the training population, the machine-learned model to identify test sequences with candidate variants that are indicative of cancer and identify cancer in test samples using the indicative test sequences;

access a plurality of test sequences from a test sample with each test sequence of the plurality of test sequences comprising one or more sequencing regions of a plurality of sequencing regions, the plurality of sequencing regions, in aggregate, forming an aggregate sequencing region;

select one or more indicative regions from the aggregate sequencing region formed from the plurality of test sequences to generate a sample population, the selected one or more indicative regions corresponding to a cancer presence in the test sample, wherein the sample population is smaller than the aggregate sequencing region; and apply the machine-learned model to the generated sample population to identify the cancer presence in the test sample, the machine-learned model:

identifying a candidate variant in an indicative region of the one or more selected indicative regions for the sample population;

comparing a test feature set of the candidate variant to a cohort feature set of a matching sequencing subregion from the cohort population; and determining the candidate variant is indicative of the cancer in the test sample based on the compared test feature set and cohort feature set.

16. The non-transitory computer-readable storage medium of claim 15, wherein the computer program instructions for selecting the one or more indicative regions from the aggregate sequencing region for the sample population, when executed by the one or more processors, cause the one or more processors to:

calculate a first methylation beta series for a sequencing region in the aggregate sequencing region;

calculate a second methylation beta series for a matching sequencing region from the cohort population, the matching sequencing region at a same genomic location as the sequencing region in the aggregate sequencing region; and for the sequencing region in the aggregate sequencing region:

calculate a set of sequence changepoints in the sequencing region based on a difference between the first methylation beta series and the second methylation beta series, and wherein the set of sequence changepoints identify positions in the sequencing region for segmenting the sequencing region into a plurality of sequencing subregions, segment the sequencing region into the plurality of sequencing subregions at the identified positions of the set of sequence changepoints, and select one or more of the sequencing subregions of the plurality of sequencing subregions for the sample population.

17. The non-transitory computer-readable storage medium of claim 16, wherein, in aggregate across the plurality of sequencing subregions, the set of sequence changepoints maximizes a difference between the first methylation beta series for the sequencing region and the second methylation beta series for the matching sequencing region.

18. The non-transitory computer-readable storage medium of claim 15, wherein the computer program instructions for selecting the one or more indicative regions from the aggregate sequencing region for the sample population, when executed by the one or more processors, cause the one or more processors to:

calculate a methylation beta series for a matching sequencing region from the cohort population, wherein:

the methylation beta series quantifies changes in methylation levels within sequencing regions, and the matching sequencing region is at a same location as a sequencing region from the aggregate sequencing region; and for the sequencing region in the aggregate sequencing region:

calculate a set of sequence changepoints in the matching sequencing region based on the methylation beta series, and wherein the set of sequence changepoints identify positions in the matching sequencing region for segmenting the sequencing region into sequencing subregions;

segment the sequencing region into a plurality of sequencing subregions at the identified positions of the set of sequence changepoints in the matching sequencing region; and select one or more of the sequencing subregions of the plurality of sequencing subregions for the sample population.

19. The non-transitory computer-readable storage medium of claim 18, wherein, in aggregate across the sequencing subregions, the set of sequence changepoints minimizes the methylation beta series for the cohort population.

20. The non-transitory computer-readable storage medium of claim 15, wherein the computer program instructions for selecting the one or more indicative regions from the aggregate sequencing region for the sample population, when executed by the one or more processors, cause the one or more processors to:

identify a plurality of CpGs in the aggregate sequencing region, each of the CpGs having a genomic length of a plurality of genomic lengths;

segment the aggregate sequencing region into a plurality of sequencing subregions, wherein each of the sequencing subregions comprises a subset of CpGs from the plurality of CpGs having substantially similar genomic lengths; and select one or more of the plurality of sequencing subregions for the sample population.

21. The non-transitory computer-readable storage medium of claim 15, wherein the computer program instructions for selecting the one or more indicative regions from the aggregate sequencing region for the sample population, when executed by the one or more processors, cause the one or more processors to:

identify a plurality of CpGs in the aggregate sequencing region;

segment the aggregate sequencing region into a plurality of sequencing subregions, wherein each sequencing subregion of the plurality comprises a number of CpGs less than a threshold number of CpGs; and select one or more of the plurality of sequencing subregions for the sample population.

22. The non-transitory computer-readable storage medium of claim 15, wherein the computer program instructions for selecting the one or more indicative regions from the aggregate sequencing region for the sample population, when executed by the one or more processors, cause the one or more processors to:
- identify a plurality of CpGs in the aggregate sequencing region;
- identify a plurality of CpG clusters using the identified plurality of CpGs, each CpG cluster comprising two or more CpGs less than a threshold genomic distance away from other CpGs in the cluster;
- segment the aggregate sequencing region into a plurality of sequencing subregions, wherein each of the sequencing subregion of the plurality comprises a CpG cluster of the plurality of CpG clusters; and
- select one or more of the plurality of sequencing subregions for the sample population.

23. The non-transitory computer-readable storage medium of claim 22, wherein selecting the one or more indicative regions for the sample population comprises identifying CpG clusters having genomic locations overlapping with genomic locations of test sequences generated by a sequencing panel for the sample.

24. The non-transitory computer-readable storage medium of claim 15, wherein the computer program instructions for selecting the one or more indicative regions from the aggregate sequencing region for the sample population, when executed by the one or more processors, cause the one or more processors to:
- calculate a genomic length for each of the plurality of sequencing regions;
- for each of the plurality of sequencing regions whose genomic length is greater than a threshold genomic length, segment the sequencing region into a plurality of sequencing subregions such that each of the plurality of sequencing subregions has a genomic length less than the threshold genomic length; and
- select, for the sample population, at least one the plurality of sequencing regions and at least one of the plurality of sequencing subregions.

25. The non-transitory computer-readable storage medium of claim 15, wherein the computer program instructions for selecting the one or more indicative regions from the aggregate sequencing region for the sample population, when executed by the one or more processors, cause the one or more processors to:
- identify a number of CpGs in each sequencing region of the plurality of sequencing regions;
- for each of the plurality of sequencing regions having a number of CpGs higher than a threshold number of CpGs, segment the sequencing region into a plurality of sequencing subregions such that each of the plurality of sequencing subregions comprises less than the threshold number of CpGs; and
- select, for the sample population, at least one of the plurality of sequencing regions and at least one of the plurality of sequencing subregions.

26. The non-transitory computer-readable storage medium of claim 15, wherein the computer program instructions for selecting the one or more indicative regions from the aggregate sequencing region for the sample population, when executed by the one or more processors, cause the one or more processors to:
- generate a plurality of paired sequencing windows for the aggregate sequencing region, each paired sequencing window comprising:
  - a sequencing region of the plurality of sequencing regions; and
  - a plurality of sequencing subregions generated from the sequencing region;
- for each of the paired sequencing windows of the plurality:
  - identify feature values for the sequencing region;
  - identify feature values for each of the plurality of sequencing subregions; and
  - calculate, using the identified feature values, mutual information scores for each of the plurality of sequencing subregions and the sequencing region; and
- select, based on the mutual information scores, at least one of the plurality of sequencing subregions or the sequencing region for the sample population.

27. The non-transitory computer-readable storage medium of claim 15, wherein the computer program instructions for selecting the one or more indicative regions from the aggregate sequencing region for the sample population, when executed by the one or more processors, cause the one or more processors to:
- generate a plurality of paired sequencing windows for the aggregate sequencing region, each paired sequencing window comprising:
  - a sequencing region of the plurality of sequencing regions; and
  - a plurality of sequence subregions generated from the sequencing region;
- generate an ensemble comprising a plurality of feature value sets, wherein each feature value set in the ensemble comprises at least one feature value different from feature values of other feature value sets in the ensemble;
- for each of the paired sequencing windows of the plurality:
  - calculate, for each feature value set in the ensemble, mutual information scores for the sequencing region and each of the plurality of sequencing subregions; and
- select, based on the mutual information scores, at least one of the plurality of sequencing subregions or the sequencing region for the sample population.

28. The non-transitory computer-readable storage medium of claim 27, wherein selecting sequencing subregions and sequencing regions for the sample population is further based on a cancer classification metric across a classification matrix comprising a plurality of elements, wherein the plurality of elements in the classification matrix represent each possible combination of feature value sets from the ensemble, sequencing regions of the plurality, and sequencing subregions generated from sequencing regions.

29. A system comprising:
- one or more processors; and
- a non-transitory computer-readable storage medium storing computer program instructions for classifying a variant in a cell free nucleic acid sample, the computer program instructions, when executed by one or more processors, causing the one or more processors to:
  - training a machine-learned model as a cancer classifier, the training comprising:
    - accessing a plurality of cohort test sequences from a cohort population, with each cohort test sequence of the plurality of cohort test sequences comprising one or more cohort sequencing regions of a plurality of cohort sequencing regions, wherein the plurality of cohort sequencing regions, in aggregate, form an aggregated cohort sequencing region;

calculating, for each of the cohort sequencing regions in the aggregated cohort sequencing region, an indicativeness for the cohort sequencing region quantifying a degree to which candidate variants in the cohort sequencing region indicate cancer presence;

selecting one or more cohort sequencing regions from the aggregated cohort sequencing region as one or more indicative regions to generate a training population, the selected indicative regions corresponding to cohort sequencing regions having calculated indicativenesses indicating cancer presence, wherein the training population is smaller than the aggregate cohort sequencing region; and training, using the training population, the machine-learned model to identify test sequences with candidate variants that are indicative of cancer and identify cancer in test samples using the indicative test sequences;

access a plurality of test sequences from a test sample with each test sequence of the plurality of test sequences comprising one or more sequencing regions of a plurality of sequencing regions, the plurality of sequencing regions, in aggregate, forming an aggregate sequencing region, select one or more indicative regions from the aggregate sequencing region formed from the plurality of test sequences to generate a sample population, the selected one or more indicative regions corresponding to a cancer presence in the test sample, wherein the sample population is smaller than the aggregate sequencing region, and apply the machine-learned model to the generated sample population to identify the cancer presence in the test sample, the machine-learned model:
identifying a candidate variant in an indicative region of the one or more selected indicative regions for the sample population;
comparing a test feature set of the candidate variant to a cohort feature set of a matching sequencing subregion from the cohort population; and
determining the candidate variant is indicative of the cancer in the test sample based on the compared test feature set and cohort feature set.

30. The system of claim 29, wherein the computer program instructions for selecting the one or more indicative regions from the aggregate sequencing region for the sample population, when executed by the one or more processors, cause the one or more processors to:
calculate a first methylation beta series for a sequencing region in the aggregate sequencing region;
calculate a second methylation beta series for a matching sequencing region from the cohort population, the matching sequencing region at a same genomic location as the sequencing region in the aggregate sequencing region; and
for the sequencing region in the aggregate sequencing region:
calculate a set of sequence changepoints in the sequencing region based on a difference between the first methylation beta series and the second methylation beta series, and wherein the set of sequence changepoints identify positions in the sequencing region for segmenting the sequencing region into a plurality of sequencing subregions,
segment the sequencing region into the plurality of sequencing subregions at the identified positions of the set of sequence changepoints, and
select one or more of the sequencing subregions of the plurality of sequencing subregions for the sample population.

31. The system of claim 30, wherein, in aggregate across the plurality of sequencing subregions, the set of sequence changepoints maximizes a difference between the first methylation beta series for the sequencing region and the second methylation beta series for the matching sequencing region.

32. The system of claim 29, wherein the computer program instructions for selecting the one or more indicative regions from the aggregate sequencing region for the sample population, when executed by the one or more processors, cause the one or more processors to:
calculate a methylation beta series for a matching sequencing region from the cohort population, wherein:
the methylation beta series quantifies changes in methylation levels within sequencing regions, and
the matching sequencing region is at a same location as a sequencing region from the aggregate sequencing region; and
for the sequencing region in the aggregate sequencing region:
calculate a set of sequence changepoints in the matching sequencing region based on the methylation beta series, and wherein the set of sequence changepoints identify positions in the matching sequencing region for segmenting the sequencing region into sequencing subregions;
segment the sequencing region into a plurality of sequencing subregions at the identified positions of the set of sequence changepoints in the matching sequencing region; and
select one or more of the sequencing subregions of the plurality of sequencing subregions for the sample population.

33. The system of claim 32, wherein, in aggregate across the sequencing subregions, the set of sequence changepoints minimizes the methylation beta series for the cohort population.

34. The system of claim 29, wherein the computer program instructions for selecting the one or more indicative regions from the aggregate sequencing region for the sample population, when executed by the one or more processors, cause the one or more processors to:
identify a plurality of CpGs in the aggregate sequencing region, each of the CpGs having a genomic length of a plurality of genomic lengths;
segment the aggregate sequencing region into a plurality of sequencing subregions, wherein each of the sequencing subregions comprises a subset of CpGs from the plurality of CpGs having substantially similar genomic lengths; and
select one or more of the plurality of sequencing subregions for the sample population.

35. The system of claim 29, wherein the computer program instructions for selecting the one or more indicative regions from the aggregate sequencing region for the sample population, when executed by the one or more processors, cause the one or more processors to:
identify a plurality of CpGs in the aggregate sequencing region;
segment the aggregate sequencing region into a plurality of sequencing subregions, wherein each sequencing subregion of the plurality comprises a number of CpGs less than a threshold number of CpGs; and select one or more of the plurality of sequencing subregions for the sample population.

36. The system of claim 29, wherein the computer program instructions for selecting the one or more indicative regions from the aggregate sequencing region for the sample population, when executed by the one or more processors, cause the one or more processors to:

identify a plurality of CpGs in the aggregate sequencing region;

identify a plurality of CpG clusters using the identified plurality of CpGs, each CpG cluster comprising two or more CpGs less than a threshold genomic distance away from other CpGs in the cluster;

segment the aggregate sequencing region into a plurality of sequencing subregions, wherein each of the sequencing subregion of the plurality comprises a CpG cluster of the plurality of CpG clusters; and select one or more of the plurality of sequencing subregions for the sample population.

37. The system of claim 36, wherein selecting the one or more indicative regions for the sample population comprises identifying CpG clusters having genomic locations overlapping with genomic locations of test sequences generated by a sequencing panel for the sample.

38. The system of claim 29, wherein the computer program instructions for selecting the one or more indicative regions from the aggregate sequencing region for the sample population, when executed by the one or more processors, cause the one or more processors to:

calculate a genomic length for each of the plurality of sequencing regions;

for each of the plurality of sequencing regions whose genomic length is greater than a threshold genomic length, segment the sequencing region into a plurality of sequencing subregions such that each of the plurality of sequencing subregions has a genomic length less than the threshold genomic length; and select, for the sample population, at least one the plurality of sequencing regions and at least one of the plurality of sequencing subregions.

39. The system of claim 29, wherein the computer program instructions for selecting the one or more indicative regions from the aggregate sequencing region for the sample population, when executed by the one or more processors, cause the one or more processors to:

identify a number of CpGs in each sequencing region of the plurality of sequencing regions;

for each of the plurality of sequencing regions having a number of CpGs higher than a threshold number of CpGs, segment the sequencing region into a plurality of sequencing subregions such that each of the plurality of sequencing subregions comprises less than the threshold number of CpGs; and select, for the sample population, at least one of the plurality of sequencing regions and at least one of the plurality of sequencing subregions.

40. The system of claim 29, wherein the computer program instructions for selecting the one or more indicative regions from the aggregate sequencing region for the sample population, when executed by the one or more processors, cause the one or more processors to:

generate a plurality of paired sequencing windows for the aggregate sequencing region, each paired sequencing window comprising:

a sequencing region of the plurality of sequencing regions; and a plurality of sequencing subregions generated from the sequencing region;

for each of the paired sequencing windows of the plurality:

identify feature values for the sequencing region;

identify feature values for each of the plurality of sequencing subregions; and calculate, using the identified feature values, mutual information scores for each of the plurality of sequencing subregions and the sequencing region; and select, based on the mutual information scores, at least one of the plurality of sequencing subregions or the sequencing region for the sample population.

41. The system of claim 29, wherein the computer program instructions for selecting the one or more indicative regions from the aggregate sequencing region for the sample population, when executed by the one or more processors, cause the one or more processors to:

generate a plurality of paired sequencing windows for the aggregate sequencing region, each paired sequencing window comprising:

a sequencing region of the plurality of sequencing regions; and a plurality of sequence subregions generated from the sequencing region;

generate an ensemble comprising a plurality of feature value sets, wherein each feature value set in the ensemble comprises at least one feature value different from feature values of other feature value sets in the ensemble;

for each of the paired sequencing windows of the plurality:

calculate, for each feature value set in the ensemble, mutual information scores for the sequencing region and each of the plurality of sequencing subregions; and select, based on the mutual information scores, at least one of the plurality of sequencing subregions or the sequencing region for the sample population.

42. The system of claim 41, wherein selecting sequencing subregions and sequencing regions for the sample population is further based on a cancer classification metric across a classification matrix comprising a plurality of elements, wherein the plurality of elements in the classification matrix represent each possible combination of feature value sets from the ensemble, sequencing regions of the plurality, and sequencing subregions generated from sequencing regions.

* * * * *